United States Patent

Huisman et al.

(10) Patent No.: US 8,993,757 B2
(45) Date of Patent: Mar. 31, 2015

(54) N-PIPERIDIN-4-YL DERIVATIVES

(75) Inventors: Ines Huisman, Oss (NL); Marcelis Van Der Stelt, Oss (NL); Wouter Wiedenhof, Oss (NL); Charles Anthony Graham Baker-Glenn, Saffron Walden (GB); Wesley Peter Blackaby, Saffron Walden (GB); Naimisha Trivedi, Saffron Walden (GB)

(73) Assignee: Merck Sharp & Dohme B.V., BN Haarlem (NL)

( * ) Notice: Subject to any disclaimer, the term of this patent is extended or adjusted under 35 U.S.C. 154(b) by 0 days.

(21) Appl. No.: 14/346,241

(22) PCT Filed: Sep. 14, 2012

(86) PCT No.: PCT/EP2012/068070
§ 371 (c)(1),
(2), (4) Date: May 19, 2014

(87) PCT Pub. No.: WO2013/041457
PCT Pub. Date: Mar. 28, 2013

(65) Prior Publication Data

US 2014/0329822 A1    Nov. 6, 2014

Related U.S. Application Data

(60) Provisional application No. 61/537,689, filed on Sep. 22, 2011.

(30) Foreign Application Priority Data

Sep. 22, 2011 (EP) .................................. 11182282

(51) Int. Cl.
| | |
|---|---|
| *C07D 401/04* | (2006.01) |
| *C07D 401/14* | (2006.01) |
| *A61K 31/444* | (2006.01) |
| *C07D 417/14* | (2006.01) |
| *C07D 405/14* | (2006.01) |
| *C07D 413/14* | (2006.01) |

(52) U.S. Cl.
CPC ............ *C07D 417/14* (2013.01); *C07D 401/14* (2013.01); *C07D 405/14* (2013.01); *C07D 413/14* (2013.01); *C07D 401/04* (2013.01)
USPC ........... 544/326; 544/328; 544/212; 514/256; 514/245

(58) Field of Classification Search
USPC .................. 544/326, 328, 212; 514/256, 245
See application file for complete search history.

(56) References Cited

U.S. PATENT DOCUMENTS 8,445,480 B2 * 5/2013 Hunt et al. ............... 514/211.15

FOREIGN PATENT DOCUMENTS

WO    WO2008117175 A2    10/2008

OTHER PUBLICATIONS

Landomiel et al., Molecular and Cellular Endocrinology 382 (2014) 452-459.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition, vol. 1, 1004-101 O, 1996.*
International Search Report for PCT/EP2012/068070 (Sep. 14, 2012), mailed on Oct. 23, 2012; 2 pages.

* cited by examiner

*Primary Examiner* — Venkataraman Balasubramanian
(74) *Attorney, Agent, or Firm* — Kenrick L. Vidale; Catherine D. Fitch

(57) ABSTRACT

The invention relates to a N-piperidin-4-yl derivative having the general Formula I or a pharmaceutically acceptable salt thereof, to pharmaceutical compositions comprising the same and to the use of said N-piperidin-4-yl derivatives for the treatment and prevention of endometriosis, for the treatment and prevention of pre-menopausal and peri-menopausal hormone-dependent breast cancer, for contraception, or for the treatment of uterine fibroids or other menstrual-related disorders.

Formula I

8 Claims, 1 Drawing Sheet

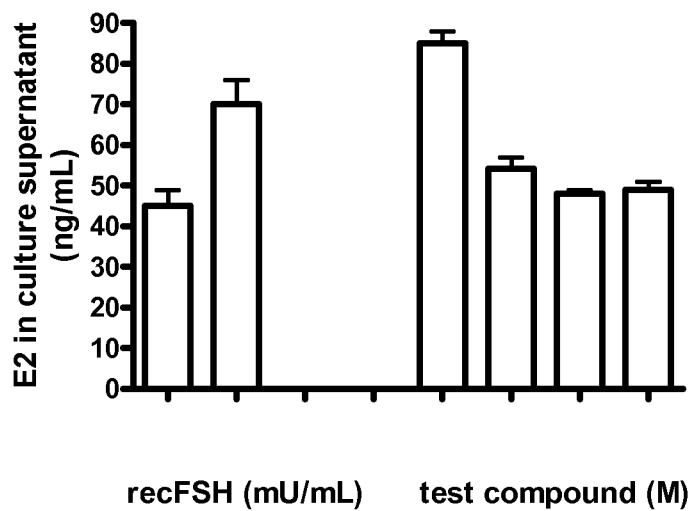
Estradiol (E2) concentration (in ng/mL) in culture supernatant of human granulosa cells, after 48 h incubation with recFSH or with the test compound (disclosed in Example 51 ) in combination with 250 mU/ml recFSH in culture medium with IBMX, followed by 2 h incubation with 10 µM testosterone in culture medium without IBMX (n = 3; mean ± s.e.m.).

N-PIPERIDIN-4-YL DERIVATIVES

The invention relates to N-piperidin-4-yl derivatives having FSH receptor modulatory activity, to a pharmaceutical composition containing the same, as well as the use of said N-piperidin-4-yl derivatives in the treatment FSH receptor mediated diseases.

Gonadotropins are important in a variety of bodily functions including metabolism, temperature regulation and the reproductive process. Gonadotropins act on specific gonadal cell types to initiate ovarian and testicular differentiation and steroidogenesis. The hypophyseal gonadotropin to FSH (follicle stimulating hormone) for example is released from the anterior pituitary under the influence of gonadotropin-releasing hormone and estrogens and plays a pivotal role in the stimulation of follicle development and maturation. FSH is the major hormone regulating secretion of follicular estrogens, whereas LH (luteinizing hormone) stimulates the production of follicular testosterone and induces ovulation (Sharp, R. M. Clin Endocrinol. 33:787-807, 1990; Dorrington and Armstrong, Recent Prog. Horm. Res. 35:301-342, 1979).

The actions of the FSH hormone are mediated by a specific plasma membrane receptor that is a member of the large family of G-protein coupled receptors. These receptors consist of a single polypeptide with seven transmembrane domains and are able to interact with the Gs protein, leading e.g. to the activation of adenylate cyclase.

The FSH receptor (FSHR) is a highly specific target in the ovarian follicle growth process and is exclusively expressed in the ovary. Blocking this receptor or inhibiting the signaling which is normally induced after FSH-mediated receptor activation will disturb follicle development and thus production of estrogens, ovulation and fertility. Low molecular weight FSH receptor antagonists, henceforth termed FSHR antagonists, could therefore form the basis for medical therapies that are in need of diminished production of estrogens and/or induction of anovulation.

Low molecular weight FSH receptor antagonists have been disclosed in International Applications WO 2008071455, WO 200807145 and WO 2008117175 and in van Straten, N. C. R. and Timmers, C. M. Annual Reports in Medicinal Chemistry 44:171-188, 2009 and van Straten, N. C. R. et al J. Med. Chem. 48:1697-1700, 2005.

Preventing or reversing endometriosis is an important goal in the field of women's health care. Endometriosis is a painful gynaecological condition that is characterized by the presence of endometrial tissue in sites outside of the uterine cavity. The prevalence rate is approximately 10% but this may be an underestimate because of the need to perform a laparoscopic procedure to determine the presence of disease. The disease affects women of reproductive age, the most common symptoms being painful menstruation (dysmenorrhoea), pain during intercourse (dyspareunia), painful bowel movement (dyschezia), chronic pelvic pain, heavy periods (menorrhagia), and infertility. If left untreated or inadequately treated endometriosis can either progress or spontaneously regress. In a significant number of women endometriosis is a chronic progressive disease manifesting itself as intractable pain, worsening quality of life, and infertility.

The etiology is unclear which also hampers an understanding of the symptomatic implications of the disease. Endometriosis produces an array of symptoms of varying severity with lack of correlation between stage of disease, disease load and degree of pain thereby causing confusion with clinical classification and delay in diagnosis. Known treatment options are drug therapy and conservative surgery.

Drug therapy may comprise the use of analgesics, hormonal contraceptives which contain both estrogen and progestagen (Combined Oral Contraceptive (COC)) or progestagen only (Progestagen-Only Contraceptive (POC)), gonadotropin releasing hormone (GnRH) agonists, or other hormones e.g. danazol. Oral contraceptive regimens with combined use of an estrogen and a progestagen (COC) are widely used as first-line therapy in suspected or diagnosed endometriosis, owing to their property to provide cycle control, reduce menstrual flow and eradicate dysmenorrhoea, the most common symptom especially in early-stage disease. However, no single product offers sufficient efficacy in combination with a tolerable level of side effects. COCs may treat some of the symptoms well, but do not effectively suppress the progress of endometriosis and do not effectively treat chronic pelvic pain.

COCs produce initial decidualization of the endometrium by creating a state of pseudocyesis and later atrophy and thinning of the endometrium, thereby providing cycle control, reduction in menstrual flow and reduction of dysmenorrhoea. COCs may treat therefore menstruation-related symptoms but they do not completely suppress the growth of endometriotic lesions and associated chronic pelvic pain.

The mechanism of action of progestagens is initial decidualization of endometrium, followed by atrophy as a result of a direct suppressive effect on estrogen receptors in the endometrium. There is evidence that progestagens suppress matrix metalloproteinases at the molecular level thereby inhibiting the growth of ectopic endometrium. Medroxyprogesterone acetate is the most widely used progestagen for the treatment of endometriosis. Although available for oral administration, medroxyprogesterone acetate is usually administered as a depot formulation every 3 months. The side effects of POCs are multiple, the most common being breakthrough bleeding, nausea, fluid retention and breast tenderness.

GnRH agonists and GnRH antagonists down-regulate the Hypothalamus-Pituitary-Ovary axis by downregulation of the GnRH receptor and GnRH receptor-mediated signalling, resulting in a hypo-estrogenic menopausal state, endometrial atrophy, and amenorrhoea. Although very effective in reducing circulating levels of estrogens, multiple side effects related to menopausal symptoms as well as osteoporosis limit duration of treatment with GnRH agonists to 6 months.

Known drug treatments and/or conservative surgery offer temporary relief only and relapse rates can be as high as 50% with a major impact on fertility and quality of life. Moreover, a significant number of women aged 40-44 years require hysterectomy and bilateral salpingo-oophorectomy.

There is thus a strong need for early therapeutic intervention that improves on the above-mentioned shortcomings of available treatment options. The need is in particular for early therapeutic intervention that suppresses progression of disease and/or improves the side-effect profile (i.e. unscheduled bleeding, bone loss and menopausal symptoms) and improves fertility outcomes.

To this aim the present invention provides N-piperidin-4-yl derivatives having the general Formula I

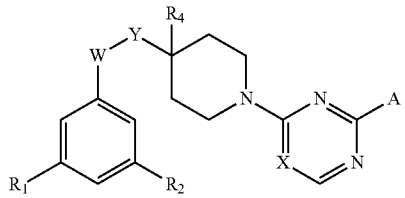

Formula I wherein
W is C(O)NH or NH(CO);
Y is CHR$_3$ or a bond;
X is N, CH, CF or C(COOR$_8$);
A is a (hetero)aromatic group selected from

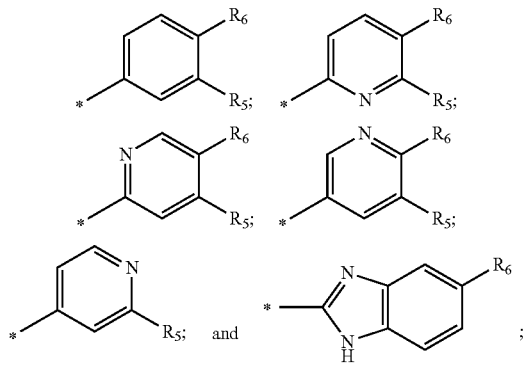

R$_1$ is H, halogen, (C$_{1-4}$)alkyl, halo(C$_{1-4}$ alkyl, (C$_{1-4}$)alkyloxy or halo(C$_{1-4}$ alkyloxy;
R$_2$ is H, halogen, di(C$_{1-4}$ alkylamino, (C$_{1-4}$)alkyl, (C$_{2-4}$)alkenyl, (C$_{2-4}$)alkynyl, halo(C$_{1-4}$)alkyl or (C$_{1-6}$)alkyloxy, optionally substituted with one or more halogens, hydroxy or (C$_{1-4}$)alkyloxy; or
R$_2$ is OCH$_2$R$_7$;
R$_3$ is H, (C$_{1-3}$)alkyl or COOR$_8$;
R$_4$ is H, halogen or (C$_{1-3}$)alkyl; or
R$_4$ forms together with R$_3$ and the carbon atoms to which they are bonded a (C$_{3-5}$)cycloalkyl group;
R$_5$ is, halogen, (C$_{1-4}$)alkyl, halo(C$_{1-4}$)alkyl, hydroxy(C$_{1-4}$ alkyl, CN, COOH, CONR$_9$, R$_{10}$, pyridyl or a 5-membered heteroaryl group comprising 1, 2 or 3 nitrogen atoms and optionally an oxygen or a sulfur atom;
R$_6$ is H, hydroxy or halogen; or
R$_6$ forms together with R$_5$ and the carbon atoms to which they are bonded a fused 5-membered heteroaryl group comprising 1 or 2 nitrogen atoms and optionally an oxygen or a sulfur atom;
R$_7$ is vinyl, ethynyl, cyano, (C$_{3-6}$)cycloalkyl, CONR$_{11}$, R$_{12}$, CH$_2$NR$_{13}$R$_{14}$, phenyl or a 5 or 6-membered heteroaryl group comprising 1-3 heteroatom selected from O, N and S; each R$_8$ is independently (C$_{1-3}$)alkyl;
R$_9$ is H or (C$_{1-6}$)alkyl, optionally substituted with 1-3 halogens, hydroxyl or COOR$_8$;
R$_{10}$ is H, (C$_{1-3}$)alkyl or a 5-membered heteroaryl group comprising 1-3 heteroatoms selected from N, S and O; or R$_9$ and R$_{10}$ form together with the nitrogen atom to which they are bonded a saturated 5-7 membered ring;
R$_{11}$, R$_{12}$, R$_{13}$ and R$_{14}$ are independently selected from H or (C$_{1-3}$)alkyl; or a pharmaceutically acceptable salt thereof.

The N-piperidin-4-yl derivatives of the invention are antagonists of the FSH receptor and can be used for the treatment and prevention of endometriosis, for the treatment and prevention of pre-menopausal and peri-menopausal hormone-dependent breast cancer, for contraception, and for the treatment of uterine fibroids and other menstrual-related disorders, such as dysfunctional uterine bleeding.

The compounds according to the present invention have FSHR modulatory activity and dose titration with such FSHR antagonists give rise to diminished follicle development (no ovulation) and reduction of circulating levels of estrogens with still sufficient estrogen production left to avoid adverse effects on e.g. bone mass.

Without intending to be bound by theory, the compounds according to the present invention are able to provide optimal control over circulating levels of estrogens by the fact that the compounds are allosteric FSHR antagonists and will therefore be less sensitive to an increase in circulating levels of FSH due to a loss of feedback inhibition by decreased levels of circulating estrogens. Moreover, dose titration of the FSHR antagonist would allow for a second level of control over FSHR signalling and thus over the balance between efficacy (decrease in estrogens) and side effects (minimal level of residual estrogens).

In contrast to GnRHR (ant)agonist treatment regimens, the higher tolerability of FSHR antagonists enables treatment for periods exceeding 6 months.

The term (C$_{1-3}$)alkyl as used here above means a branched or unbranched alkyl group having 1-3 carbon atoms, being methyl, ethyl, propyl and isopropyl.

The term (C$_{1-4}$)alkyl means a branched or unbranched alkyl group having 1-4 carbon atoms, being methyl, ethyl, propyl, isopropyl, butyl, isobutyl, sec-butyl and tert-butyl.

The term (C$_{1-6}$)alkyl means a branched or unbranched alkyl group having 1-6 carbon atoms, for example methyl, ethyl, propyl, isopropyl, butyl, tert-butyl, n-pentyl and n-hexyl.

The term (C$_{2-4}$)alkenyl means a branched or unbranched alkenyl group having 2-4 carbon atoms, such as such as vinyl, allyl and butenyl.

The term (C$_{2-4}$)alkynyl means a branched or unbranched alkenyl group having 2-4 carbon atoms, such as ethynyl, propynyl and butynyl.

The term (C$_{3-5}$)cycloalkyl means a cycloalkyl group having 3-5 carbon atoms, such as cyclopentyl, cyclobutyl and cyclopropyl.

The term (C$_{3-6}$)cycloalkyl likewise means a cycloalkyl group having 3-6 carbon atoms, such as cyclopentyl, cyclobutyl and cyclopropyl.

The term halo(C$_{1-6}$)alkyl means a (C$_{1-6}$)alkyl group, as previously defined, substituted by one or more halogens, preferably one or more fluoro. A preferred halo(C$_{1-4}$)alkyl group is trifluoromethyl.

The term hydroxy(C$_{1-4}$ alkyl means an (C$_{1-4}$)alkyl group, as previously defined, substituted with 1 to 3 hydroxy groups.

The term (C$_{1-4}$)alkoxy means an alkoxy group having 1-4 carbon atoms, the alkyl moiety having the same meaning as previously defined. (C$_{1-3}$)alkoxy groups are preferred.

The term (C$_{1-6}$)alkoxy means an alkoxy group having 1-6 carbon atoms, the alkyl moiety having the same meaning as previously defined.

The terms halo(C$_{1-4}$)alkoxy means an (C$_{1-4}$)alkoxy group, as previously defined, substituted with 1 or more halogens, the preferred halogen being fluoride. A preferred halo($C_{1-4}$) alkoxy group is trifluoromethoxy.

The term halogen means fluorine, chlorine, bromine or iodine.

In the definition of Formula I substituent $R_5$ can represent a 5-membered heteroaryl group comprising 1, 2 or 3 nitrogen atoms and optionally an oxygen or a sulfur atom. These heteroaryl rings may be substituted with ($C_{1-3}$)alkyl, ($C_{1-3}$) alkoxy or halogen. Examples of such heteroaryl groups, which can be attached through a carbon atom or through a nitrogen atom, are imidazolyl, pyrazolyl, thiazolyl, isothiazolyl, oxazolyl, isoxazolyl, thienyl, oxadiazolyl and the like.

Preferred are 1H-pyrazol-1-yl, 1H-pyrazol-3-yl, 1-methyl-1H-pyrazol-3-yl, 1H-imidazol-2-yl, 2H-1,2,3-triazol-2-yl, 1,3-thiazol-2-yl or 1,3-oxazol-2-yl.

In the definition of Formula I substituent $R_7$ can represent a 5 or 6-membered heteroaryl group comprising 1-3 heteroatom selected from O, N and S. Examples of such heteroaryl groups are pyridyl, pyrimidyl, furyl, thienyl, oxazolyl, isoxazolyl, thiazolyl and the like. Preferred are furan-3-yl, 1,2-oxazol-3-yl and 5-methyl-1,2-oxazol-3-yl.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit-risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Preferred in the invention are N-piperidin-4-yl derivatives according to Formula I wherein W is C(O)NH. Further preferred are compounds of Formula I wherein $R_4$ is H. Also preferred are compounds of the invention wherein A is

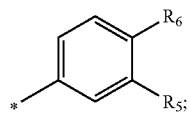

$R_5$ is CN or a 5-membered heteroaryl group comprising 2 nitrogen atoms; and $R_6$ is H. Further preferred are the N-piperidin-4-yl derivatives of the invention according to Formula I wherein $R_5$ is 1H-pyrazol-1-yl, 1H-pyrazol-5-yl or 1H-imidazol-2-yl, as well as the N-piperidin-4-yl derivatives wherein $R_1$ is ($C_{1-4}$)alkyl-oxy and $R_2$ is OCH$_2$R$_7$, $R_7$ being ($C_{3-6}$)cycloalkyl.

Specifically preferred N-piperidin-4-yl derivatives of the invention are:
1-(2-(3-(1H-pyrazol-1-yl)phenyl)pyrimidin-4-yl)-N-(3-methoxy-5-((5-methylisoxazol-3-yl)methoxy)phenyl)piperidine-4-carboxamide;
N-((1-(2-(3-(1H-pyrazol-1-yl)phenyl)pyrimidin-4-yl)piperidin-4-yl)methyl)-3-(cyclopropylmethoxy)-5-methoxybenzamide;
N-((1-(2-(3-(1H-pyrazol-1-yl)phenyl)pyrimidin-4-yl)piperidin-4-yl)methyl)-3-methoxy-5-((5-methylisoxazol-3-yl)methoxy)benzamide;
N-((1-(4-(1H-pyrazol-1-yl)phenyl)-1,3,5-triazin-2-yl)piperidin-4-yl)methyl)-3-(cyclopropylmethoxy)-5-methoxybenzamide;
N-((1-(4-(3-cyanophenyl)-1,3,5-triazin-2-yl)piperidin-4-yl) methyl)-3-methoxy-5-(2,2,2-trifluoroethoxy)benzamide;
N-((1-(2-(3-(1H-pyrazol-5-yl)phenyl)-5-fluoropyrimidin-4-yl)piperidin-4-yl)methyl)-3-(cyclopropylmethoxy)-5-methoxybenzamide;
3-(cyclopropylmethoxy)-5-methoxy-N-((1-(2-(3-(1-methyl-1H-pyrazol-3-ylcarbamoyl)phenyl)pyrimidin-4-yl)piperidin-4-yl)methyl)benzamide;
3-(cyclopropylmethoxy)-5-methoxy-N-((1-(2-(3-(4-methyl-1H-pyrazol-1-yl)phenyl)pyrimidin-4-yl)piperidin-4-yl) methyl)benzamide;
N-(1-(1-(4-(3-(1H-pyrazol-3-yl)phenyl)-1,3,5-triazin-2-yl) piperidin-4-yl)ethyl)-3-(cyclopropylmethoxy)-5-methoxybenzamide;
N-(1-(1-(2-(3-cyanophenyl)pyrimidin-4-yl)piperidin-4-yl) ethyl)-3-(cyclopropylmethoxy)-5-methoxybenzamide;
N-(1-(1-(2-(3-(1H-pyrazol-1-yl)phenyl)pyrimidin-4-yl)piperidin-4-yl)ethyl)-3-(cyclopropylmethoxy)-5-methoxybenzamide;
N-((1-(4-(3-(1H-imidazol-2-yl)phenyl)-1,3,5-triazin-2-yl) piperidin-4-yl)methyl)-3-(cyclopropylmethoxy)-5-methoxybenzamide 2,2,2-trifluoroacetate;
1-(2-(3-(1H-pyrazol-1-yl)phenyl)pyrimidin-4-yl)-N-(3,5-dimethoxyphenyl) piperidine-4-carboxamide; and
N-((1-(2-(3-(1H-imidazol-2-yl)phenyl)-5-fluoropyrimidin-4-yl)piperidin-4-yl)-methyl)-3-(cyclopropylmethoxy)-5-methoxybenzamide 2,2,2-trifluoroacetate; or a pharmaceutically acceptable salt thereof.

In vitro assays to determine receptor binding or the biological activity of gonadotropin receptor agonists and antagonists are well-known. In general, cells expressing the receptor are incubated with the compound to be tested and the binding or stimulation or inhibition of a functional response is determined. To measure a functional response, isolated DNA encoding the FSH receptor gene, preferably the human receptor, is expressed in a suitable host cell-line. Such a host cell-line might be the Chinese Hamster Ovary cell-line, but other cell-lines can also be used. Preferably, the host cells are of mammalian origin (Jia et al (1991) Mol Endocrinol 5, 759-776).

Methods to construct FSH receptor-expressing cell lines are well-known in the art (e.g., Sambrook et al., Molecular Cloning: A Laboratory Manual, Cold Spring Harbor Laboratory Press, latest edition). Heterogolous expression of the receptor is obtained by transfection and expression of the DNA encoding the desired protein. Techniques for site-directed mutagenesis, ligation of additional sequences, PCR, and construction of suitable expression systems are also well-known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well-known, expression systems are available, which are compatible with a wide variety of hosts, including prokaryotic hosts such as bacteria and eukaryotic hosts such as yeast, plant cells, insect cells, avian cells, mammalian cells, and the like.

Cells expressing the receptor are then incubated with the test compound to determine binding, or stimulation or inhibition of a functional response. Alternatively, isolated cell membranes containing the expressed receptor may be used to measure binding of compound.

For measurement of binding, radioactively- or fluorescently-labeled compounds may be used. Alternatively, competition binding assays may be performed. FSH receptor antagonistic compounds can also be identified in screening assays that involve the determination of receptor-mediated cAMP accumulation. Such methods involve the expression of the FSH receptor in a host cell-line and incubation of the cells with a concentration range of the test compound in the presence of a fixed, submaximally effective, FSH concentration (i.e., a FSH concentration that induces approximately 80% of the maximal cAMP accumulation by FSH in the absence of test compound). The amount of cAMP is then measured. From the concentration-effect curves, the IC50 value and the percentage of inhibition of FSH-induced cAMP accumulation can be determined for each of the compounds. As agonist, human recombinant FSH can be used.

The N-piperidin-4-yl derivatives of the invention were found to have antagonistic activity at the human FSH receptor as was determined in Chinese Hamster Ovary (CHO) cells stably transfected with the human FSH receptor (see Example 51). The FSHR antagonists of the invention have pIC50 values higher than 6 in said assay. The preferred compounds of the invention have pIC50 values higher than 8.

In addition to the direct measurement of cAMP levels in the FSH receptor-expressing cell-line, cell-lines may be transfected with a second cDNA that encodes a reporter gene, of which the expression is dependent on the intracellular concentration of cAMP. Such reporter genes might be cAMP-inducible or be constructed in such a way that they are connected to novel cAMP responsive elements. In general, reporter gene expression might be controlled by any response element reacting to changing levels of intracellular cAMP. Suitable reporter genes are e.g. the genes encoding beta-galactosidase, alkaline phosphatase, firefly luciferase and green fluorescence protein. The principles of such transactivation assays are well-known in the art and are described for example in Stratowa et al (1995) Curr Opin Biotechnol 6, 574. Changes in intracellular cAMP levels may also be determined in live-cell cAMP biosensor assays, like the GloSensor™ cAMP assay, which uses a genetically encoded biosensor with a cAMP binding domain fused to a mutant form of luciferase, or the ACT One™ cAMP assay, which utilizes a cAMP-gated ion channel as a biosensor. Antagonistic compounds may also be identified in assays that are based on receptor-induced recruitment of beta-arrestin to the agonist-occupied receptor (e.g., Transfluor® assay, PathHunter® and Tango™ beta-arrestin assays) or receptor internalization assays (e.g., Path Hunter® endocytosis assays). Label-free assays may also be applicable to screen for FSH receptor antagonists. These assays are based on receptor-induced dynamic mass redistribution of intracellular content or receptor-induced changes in cell morphology or adhesion (Van Koppen (2010) Drug Discovery tb 7, 69).

The compounds of Formula I can form salts which are also within the scope of this invention. Reference to a compound of Formula I herein is understood to include reference to salts thereof, unless otherwise indicated.

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press and Jana S. et al, Current Med. Chem. 17, 3874-3908, 2010. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The present disclosure describes the preparation of low molecular weight compounds that show selective modulatory activity on the FSH receptor. The compounds of the invention can be used as (partial) antagonists of the FSH receptor.

The present invention therefore relates to FSHR antagonists as a means for the treatment and/or prevention of endometriosis, for the treatment and/or prevention of pre-menopausal and peri-menopausal hormone-dependent breast cancer, for contraception, and for the treatment of uterine fibroids and other menstrual-related disorders, such as dysfunctional uterine bleeding.

Thus, the compounds according to the invention can be used in therapy.

A further aspect of the invention resides in the use of compounds according to the invention or a pharmaceutically acceptable salt thereof for the treatment of FSH receptor-mediated diseases.

Another aspect of the invention resides in the use of compounds or a pharmaceutically acceptable salt thereof having the general formula I for the treatment of diseases wherein FSHR mediated signaling plays a role, in particular those diseases wherein signaling can be inhibited by antagonizing the FSHR. These include, but are not limited to, the treatment and prevention of endometriosis, for the treatment and prevention of pre-menopausal and peri-menopausal hormone-dependent breast cancer, for contraception, and for the treatment of uterine fibroids and other menstrual-related disorders, such as dysfunctional uterine bleeding.

In a further embodiment of the invention, a compound according to the invention is used to treat endometriosis by providing improved control over circulating levels of estrogens by dose titration thereby allowing optimal control over the balance between efficacy and side effects. Moreover, the selective on-target interaction with the FSHR will not impede LHR mediated signalling and associated production of testosterone. With the improvement in tolerability, a compound according to the present invention can also provide a simple effective treatment, preferably by the oral route of administration, in an early stage of the disease in a patient population familiar with contraceptive methods. Oral treatment is available by administration of a compound according to the invention in a pharmaceutical formulation. During treatment with a compound according to the invention, regular bleeding can be partially or completely avoided (inducing amenorrhoea). This is particularly useful in the treatment of endometriosis since it diminishes or prevents retrograde menstruation and thereby minimizes recurrence of disease.

A compound according to the invention can also be used for contraception. A compound according to the invention has therapeutic and contraceptive effect while inducing a mostly atrophic or inactive endometrium. This treatment thereby avoids endometrial proliferation or hyperplasia. Compounds according to the invention are also useful for treatment of other menstrual-related conditions such as fibroids and dysfunctional uterine bleeding. Furthermore, in view of the property of the compounds, according to the invention, to diminish circulating levels of estrogens, a compound according to the invention is also very useful for treatment of estrogen receptor positive breast cancer, either alone or in combination with an estrogen receptor antagonists such as tamoxifen or a selective estrogen receptor downregulator such as fulvestrant, in pre-menopausal and perimenopausal women.

The N-piperidin-4-yl derivatives according to Formula I may be prepared by the general methods depicted in Schemes 1-12.

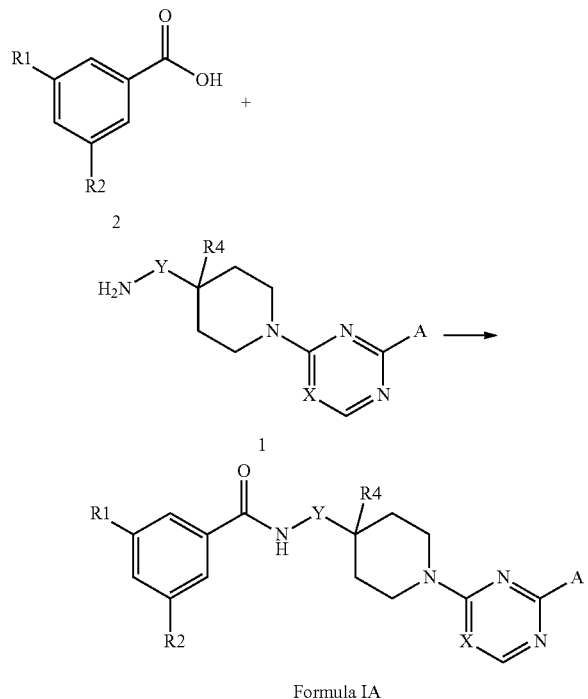

The N-piperidin-4-yl derivatives of Formula I, wherein $R_1$, $R_2$, $R_4$, A, X, Y and W are as previously defined, can be prepared by methods known in the art of organic chemistry.

Compounds of Formula IA, wherein W is C(O)NH (Scheme 1), can for instance, be obtained from the condensation of an amine derivative of formula 1 with an appropriate benzoic acid of formula 2 using an amide bond forming reagent, such as HATU or TBTU or the like, in the presence of an organic base such as DIPEA, and in a suitable solvent such as DMF or $CH_2Cl_2$. The benzoic acids can be obtained from commercial sources or can easily be prepared by using standard organic synthesis techniques such as depicted in Scheme 2.

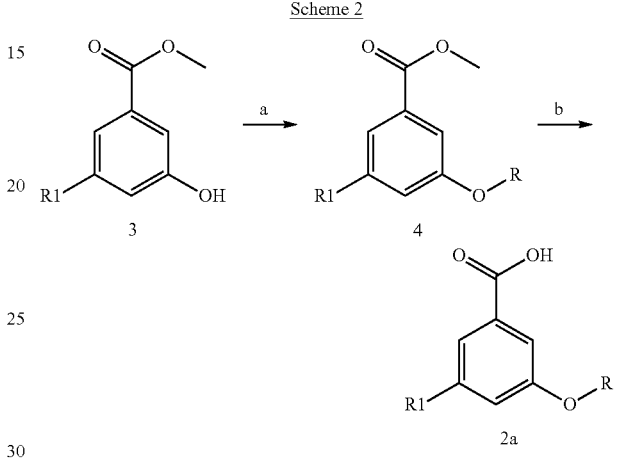

Compounds of formula 2a, wherein $R_1$ is $OCH_3$ and $R_2$ is OR, wherein R is $(C_{1-6})$alkyl, optionally substituted with one or more halogens, hydroxy or $(C_{1-4}$-alkyloxy; or R is $CH_2R_7$, wherein $R_7$ has the meaning as previously defined, can for instance be prepared as depicted in scheme 2 by functionalization of methyl 3-hydroxy-5-methoxybenzoate 3 using known methods e.g. alkylation with alkyl halides or similar reagents, followed by a straight forward hydrolysis of the methyl ester 4 under basic or acidic conditions. Introduction of other substituents $R_2$ in this stage may be accomplished by triflation of compounds 3 using triflic anhydride in the presence of a suitable base, leading to derivatives 4 ($R=SO_2CF_3$). In turn, triflates 4 can be converted via well known organometallic reactions like Ullmann-, Suzuki-, Stille-, Sonogashira-, Heck- and Buchwald-protocols to substituents containing carbon-carbon single, double and triple bonds, carbon nitrogen bonds (anilines and amides) as well as nitriles.

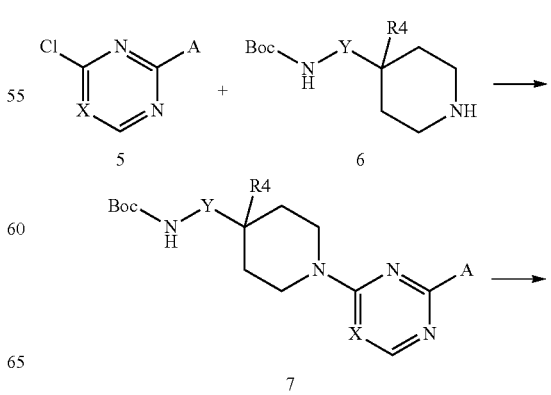

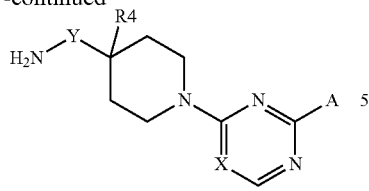

Compounds of formula 1, can be obtained by coupling of compounds 5 (X=CR or N) and piperidines 6, wherein R₄ and Y are as previously defined, in the present of a tertiary amine base (e.g. triethyl amine) in a suitable solvent such as ethanol to give 7 from which the Boc group is removed by treatment with acid (e.g. HCl) in an organic solvent such as dioxane or ethyl acetate.

Scheme 4

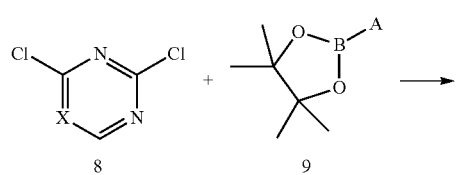

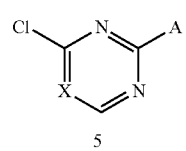

Compounds of formula 5 wherein X and A are as previously defined, can be obtained by a Suzuki-Miyaura arylation of compounds 8 using the appropriate aryl boronic esters 9 (corresponding boronic acids may also be used). In a typical procedure, a mixture of compound 8, a palladium catalyst (e.g. Pd(PPh₃)₄ or Pd(dppf)₂Cl₂), base (e.g. aqueous K₂CO₃, NaOH or the like) and a aryl boronic ester 9 in a suitable solvent such as dioxane or toluene/EtOH, is heated under a nitrogen atmosphere under microwave irradiation or using conventional heating. It will be appreciated by those of skill in the art that functionalization of dichlorides 8 with boronic esters 9 may lead to the formation of mixtures of products in which either chloride atom or both chlorides are substituted. In general, purification of such mixtures using standard techniques such as column chromatography, HPLC or UPLC gives access to the desired derivatives of general formula 5.

The boronic esters 9 can be obtained from commercial sources or can easily be prepared from the corresponding arylbromides or aryliodides using known methods.

Scheme 5

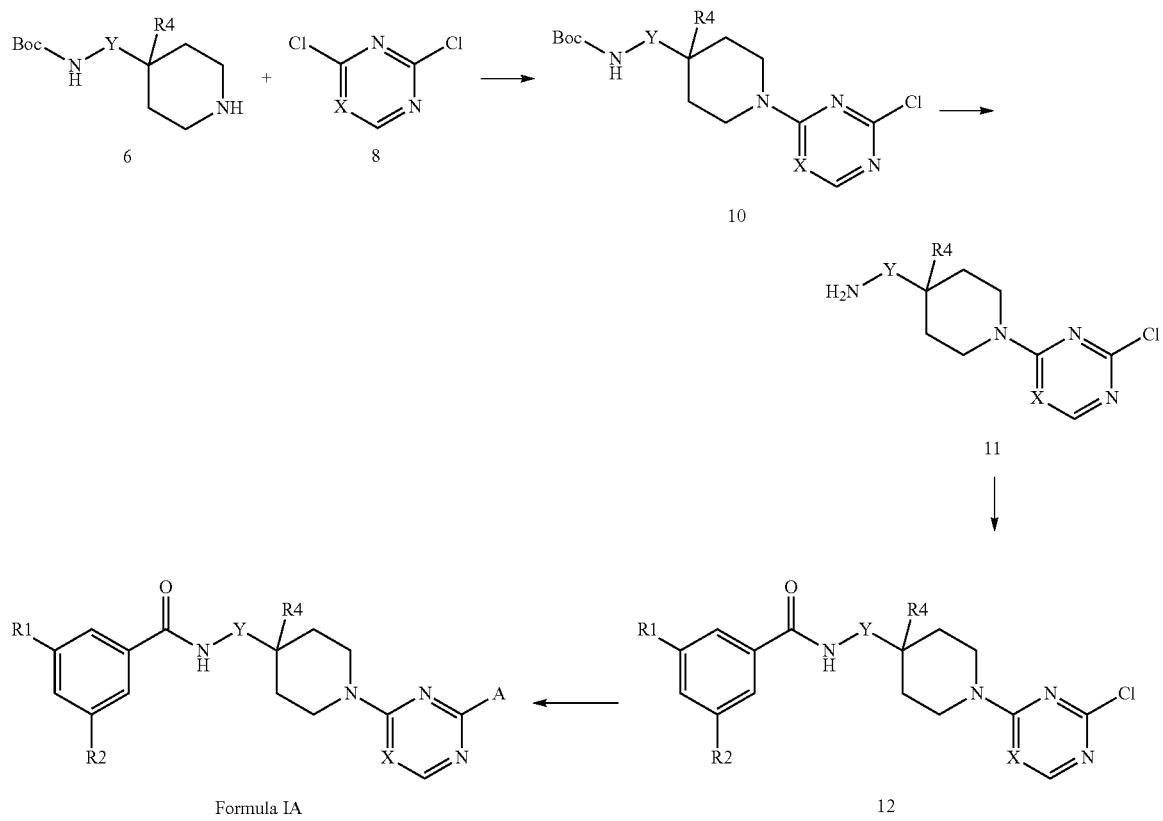

An alternative synthetic route for the preparation of compounds of Formula IA of the invention is depicted in scheme 5. In this route the final step is the Suzuki-Miyaura arylation of compounds 12 with appropriate boronic esters 6, using a typical procedure as described in scheme 4. Compounds 12 can be obtained starting from compounds 6 and 8 as depicted in scheme 3 to give compounds 10. The Boc group is removed by treatment with acid (e.g. HCl in dioxane) to give compounds 11.

Condensation of compounds 11 with an appropriate benzoic acid of formula 2 using an amide bond forming reagent, such as HATU or TBTU or the like in the presence of an appropriate base and in a suitable solvent such as DMF or $CH_2Cl_2$ afford compounds 12.

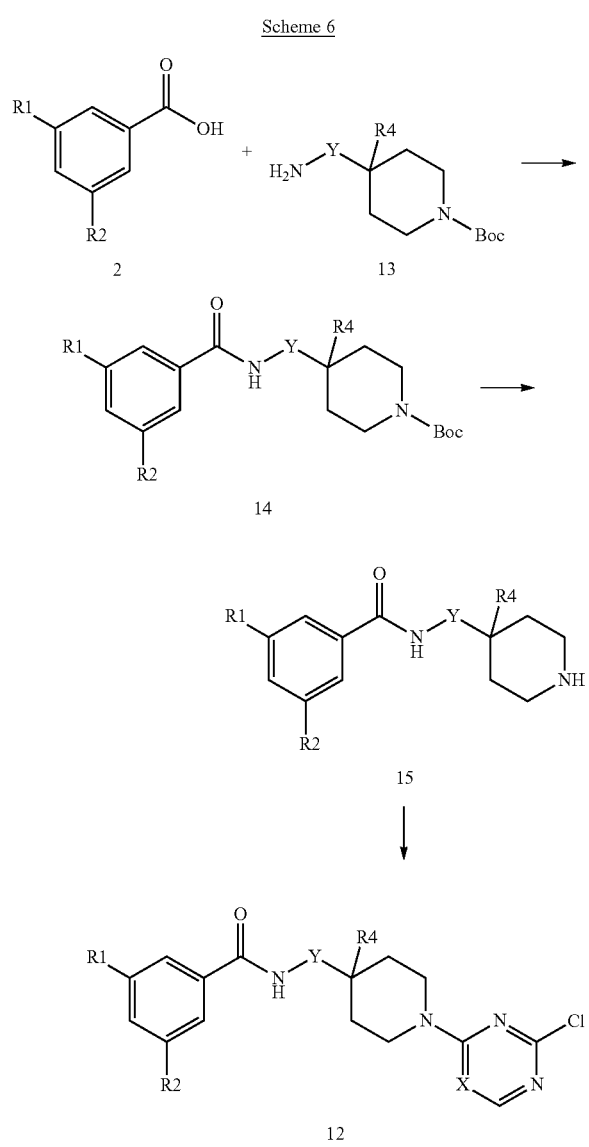

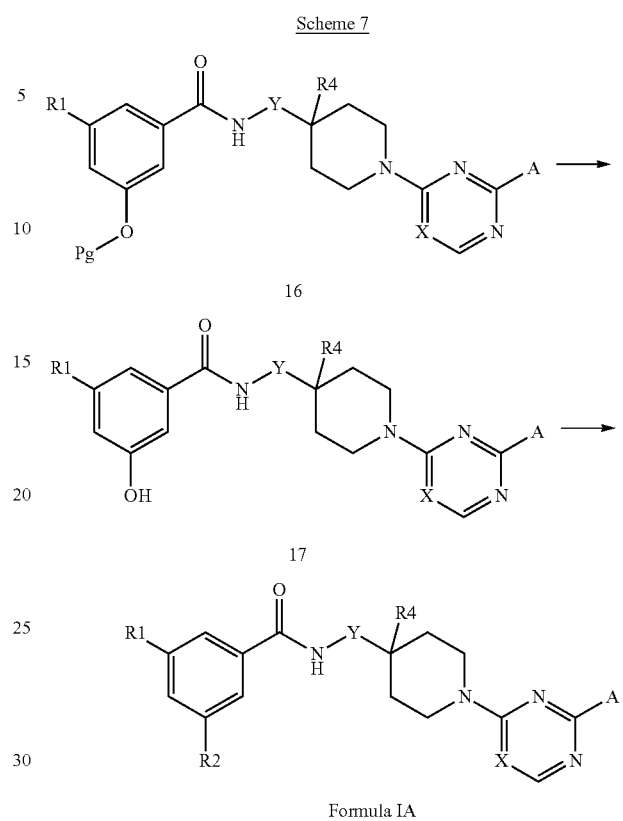

In addition, condensation of compounds 2 and 13 as previously described give compounds 14. Removal of the Boc group using an acid (e.g. trifluoroacetic acid) yields compounds 15. Coupling of compounds 15 and 8, using conditions described in scheme 3, affords compounds 12.

Compounds of Formula IA in which $R_1$ and $R_2$ are as defined in 2a ($R_1$=$OCH_3$ and $R_2$=OR), can also be obtained from compounds 17 by functionalization of the meta hydroxyl moiety, using known methods e.g. alkylation with alkyl halides or similar reagents. Introduction of other substituents $R_2$ in this stage may be accomplished by triflation of compounds 17 using triflic anhydride in the presence of a suitable base, leading to derivatives of formula 1A ($R_2$=$OSO_2CF_3$). In turn, these triflates 1A ($R_2$=$OSO_2CF_3$) can be converted via well known organometallic reactions like Ullmann-, Suzuki-, Stille-, Sonogashira-, Heck- and Buchwald-protocols to substituents containing carbon-carbon single, double and triple bonds, carbon nitrogen bonds (anilines and amides) as well as nitriles.

Compounds 17 can be obtained from compounds 16, which can be prepared as described in scheme 1 and scheme 2 and wherein $R_1$, $R_4$, A, X and Y are as previously defined and Pg is a protecting group e.g. benzyl or TMS or the like, by removal of the protecting group, using methods known to those skilled in the art.

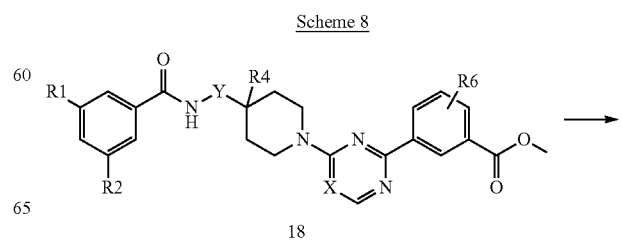

Scheme 9

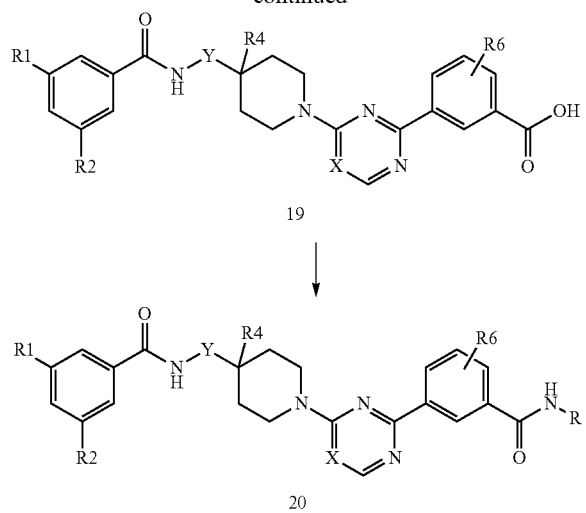

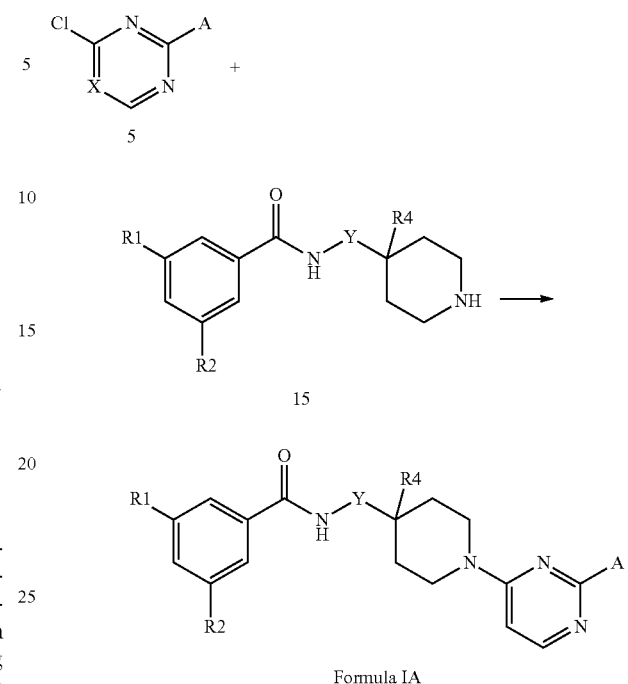

Compounds of Formula IA, wherein A is an amide containing aryl group and $R_1$, $R_2$, $R_4$, $R_6$, X and Y are as previously defined (compounds 20) can be obtained by condensation of an amine (e.g. alkyl amine, aryl amine or the like) with the benzoic acid derivatives 19 using an amide bond forming reagent, such as HATU or TBTU or the like in a suitable solvent such as DMF or $CH_2Cl_2$. Compounds 19 can easily be prepared by hydrolysis of the methyl ester of compounds 18 by treatment with base (e.g. aqueous NaOH or the like) in a suitable solvent such as methanol:water. Compounds 18 can be prepared as described in scheme 5.

Alternatively, compounds of Formula IA can also be obtained by the coupling of compounds 5 and 15 in the present of a tertiary amine base (e.g. triethyl amine) in a suitable solvent such as ethanol.

Scheme 10

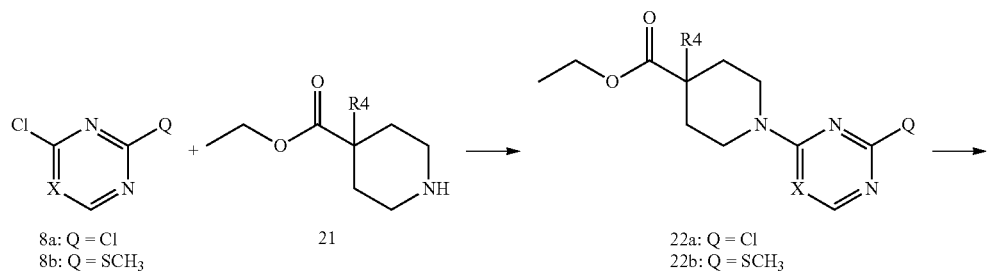

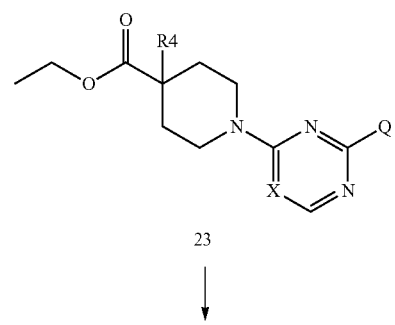

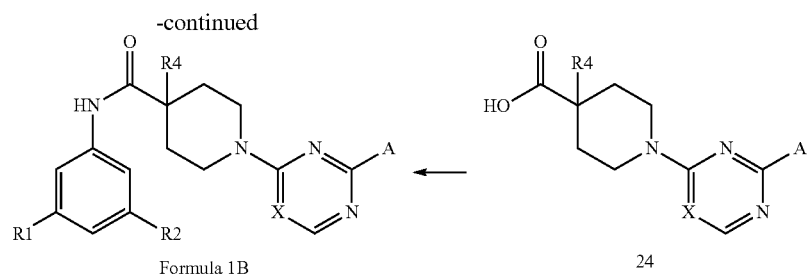

Formula 1B

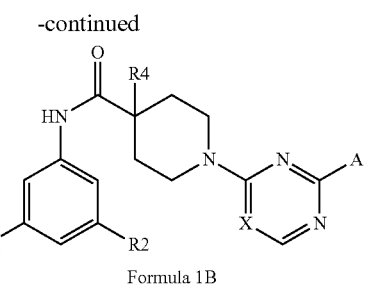

24

Compounds of Formula IB, wherein W is NHC(O) and Y=absent, can be obtained by condensation of compounds 24 with an appropriate aniline using an amide forming bond reagent, such as HATU or TBTU or the like in a suitable solvent such as DMF or $CH_2Cl_2$ (scheme 10). Compounds 24 can easily be prepared by hydrolysis of the ethyl ester of compounds 23, which is synthesized via a Suzuki-Miyaura arylation of compounds 22a (Q=Cl) with the appropriate boronic esters 9. Compounds 23 can also be derived from the thioethers 22b via a Liebeskind-Srogl reaction. A non-basic, Cu(I) mediated (e.g. Cu(I)-thiophene-2-carboxylate), palladium catalyzed (e.g. Pd(Ph₃)₄) arylation with the appropriate boronic esters 9 in a suitable solvent such as THF. Related conversions have been described in: Villalobos, J. M.; Srogl, J.; Liebeskind, L. S., *J. Am. Chem. Soc.* 129 (51): 15734-15735 (2007). Compounds 22 can be obtained from the coupling of compounds 8 and 21 as described previously.

-continued

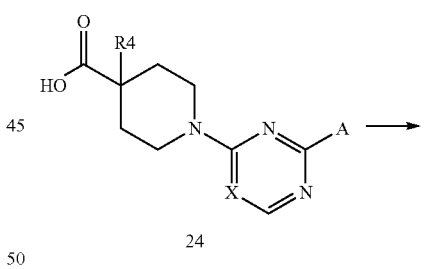

Formula 1B

Alternatively, compounds of Formula IB can also be prepared as reported in scheme 11. The final step is the arylation of compounds 26 with appropriate boronic esters under either Suzuki-Miyaura conditions for compounds 26a or Liebeskind-Srogl conditions in case of compounds 26b as described above. Compounds 26 can be obtained by condensation of compounds 25 with appropriate anilines using conditions as shown previously. Compounds 25 can be obtained by straight forward hydrolysis of the ethyl ester 22.

Scheme 11

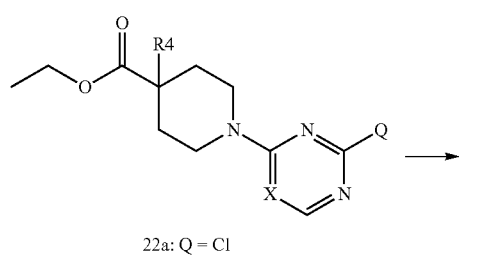

22a: Q = Cl
22b: Q = SCH₃

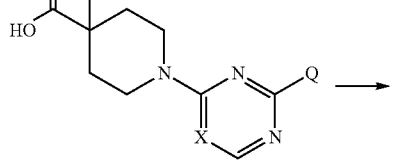

25a: Q = Cl
25b: Q = SCH₃

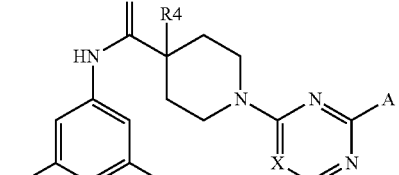

26a: Q = Cl
26b: Q = SCH₃

Scheme 12

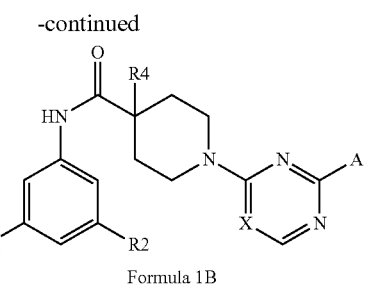

24

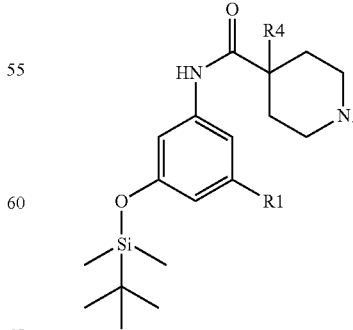

27

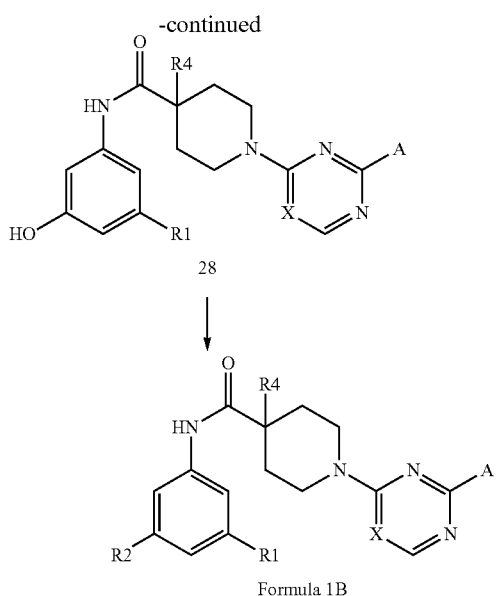

28

↓

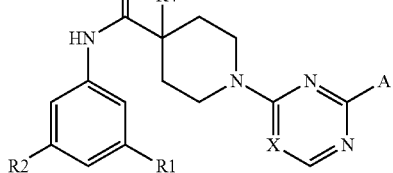

Formula 1B

Finally, compounds of Formula IB can be prepared as shown in scheme 12. The final step is the functionalization of the hydroxyl group of compounds 28, using standard methods e.g. alkylation with alkyl halides or similar reagents. Introduction of other substituents $R_2$ in this stage may be accomplished by triflation of compounds 28 using triflic anhydride in the presence of a suitable base, leading to derivatives of formula 1B ($R_2$=$OSO_2CF_3$). In turn, these triflates 1B ($R_2$=$OSO_2CF_3$) can be converted via well known organometallic reactions like Ullmann-, Suzuki-, Stille-, Sonogashira-, Heck- and Buchwald-protocols to substituents containing carbon-carbon single, double and triple bonds, carbon nitrogen bonds (anilines and amides) as well as nitriles. Compounds 28 can be obtained by removal of the TBDMS protecting group of compounds 27 by treatment with acid (e.g. HCl) in a suitable solvent such as dioxane or $CH_2Cl_2$. Compounds 27 can be prepared by a condensation of the appropriate aniline with compounds 24 as previously described.

The invention is illustrated by the following examples.

EXAMPLES

The following abbreviations have been used: Boc: tert-butoxycarbonyl; CDCl3: chloroform-d; DiPEA: N,N-diisopropylethyl amine; DMF: N,N-dimethylformamide; $Et_3N$ or TEA: triethyl amine; HPLC: high performance liquid chromatography; TFA: trifluoro acetic acid; MS: mass spectrum; $(PPh_3)_4Pd$: tetrakis(triphenylphosphine)palladium(0); THF: tetrahydrofuran; TLC: thin layer chromatography; $SiO_2$: silicagel; N: Normal; t-BuOK; potassium tert-butoxide; TBDMS: tert-butyldimethylsilyl; TMS: trimethylsilyl; HATU: (2-(7-Aza-1H-benzotriazole-1-yl)-1,1,3,3-tetramethyluronium hexafluorophosphate); TBTU: (2-(1H-Benzotriazole-1-yl)-1,1,3,3-tetramethyluronium tetrafluoroborate); APCl-MS: atmospheric pressure chemical ionization mass spectrometry; ESI-MS; electrospray ionization-mass spectroscopy.

General $^1$H NMR spectra were recorded on a Bruker spectrometer (400 MHz) with deuterochloroform as the solvent unless stated otherwise. Chemical shifts are reported as δ values (parts per million) relative to tetramethylsilane as an internal standard.

MS: Electro Spray spectra were recorded on the Applied Biosystems API-165 single quad MS in alternating positive and negative ion mode using Flow Injection. The mass range was 120-2000 Da and scanned with a step rate of 0.2 Da. and the capillary voltage was set to 5000 V. N2-gas was used for nebulasation.

LC-MS spectrometer (Waters) Detector: PDA (200-320 nm), Mass detector: ZQ

All target compounds were characterized and determined to be at least >95% pure by $^1$H NMR, MS and analytical HPLC.

Example 1

Intermediate Compound 3-(cyclopropylmethoxy)-5-methoxybenzoic acid i) To a stirred solution of methyl 3,5-dihydroxybenzoate (80 g, 0.52 mol) in $CH_3OH$ (600 ml), was added concentrated $H_2SO_4$ (40 ml) in portions at room temperature. The reaction mixture was heated to reflux temperature for 4 hours. After cooling to room temperature, the reaction mixture was concentrated under reduced pressure and the residue was dissolved in ethyl acetate. This solution was washed with a saturated aqueous $Na_2CO_3$ solution, brine, dried over $Na_2SO_4$ and concentrated under reduced pressure to give methyl 3-hydroxy-5-methoxybenzoate (73 g) as a white solid. The crude product was used in the next step without further purification.

ii) To a stirred solution of the product obtained in the previous step (10.0 g) in $CH_3CN$ (140 ml) were added at room temperature, $K_2CO_3$ (15.2 g, 110 mmol) and bromomethylcyclopropane (10.5 ml, 77 mmol). The reaction mixture was heated to 70-80° C. for 5 hours. After completion, the mixture was filtered and the filtrate was concentrated under reduced pressure to give methyl 3-(cyclopropylmethoxy)-5-methoxybenzoate (8.5 g). The crude product was used in the next step without further purification.

iii) To a stirred solution of the product obtained in the previous step (8.5 g, 35.7 mmol) in $CH_3OH$ (50 ml) and $H_2O$ (50 ml), was added $LiOH.H_2O$ (4.5 g, 107 mmol) in one portion. The reaction mixture was stirred at room temperature for 3 hours. The organic solvent was removed under reduced pressure and the pH was adjusted to pH=3 with concentrated hydrochloric acid. The aqueous layer was extracted with ethyl acetate, washed with brine, dried over $Na_2SO_4$. The organic layer was concentrated under reduced pressure to give the title compound 3-(cyclopropylmethoxy)-5-methoxybenzoic acid (7.8 g) as a white solid. The crude product was used in the next step without further purification.

$^1$H NMR (DMSO): δ 13.00 (s, 1H), 7.03 (t, 2H, J=2.26 Hz), 6.73 (t, 1H, J=2.04 Hz), 3.84 (d, 2H, J=6.56 Hz), 3.77 (s, 3H), 1.22-1.19 (m, 1H), 0.59-0.54 (m, 2H), 0.34-0.31 (m, 2H).

Example 2

Intermediate Compound

Following a procedure analogous to that described in Example 1, the following compound was prepared.

3-methoxy-5-((5-methylisoxazol-3-yl)methoxy)benzoic acid $^1$H NMR (CDCl$_3$): δ 7.33 (s, 1H), 7.29 (s, 1H), 6.77 (t, 1H, J=2.30 Hz), 6.12 (s, 1H), 5.15 (s, 2H), 3.84 (s, 3H), 2.44 (s, 3H).

Example 3

Intermediate Compound 3-methoxy-5-(2-methoxyethoxy)benzoic acid i) To a solution of methyl 3-hydroxy-5-methoxybenzoate (Example 1, step i, 0.5 g, 2.7 mmol) in DMF (10 ml) was added NaH (0.2 g, 5.4 mmol) at 0 under a nitrogen atmosphere. After stirring for minutes, 1-bromo-2-methoxyethane (0.75 g, 5.4 mmol) was added and the reaction mixture was stirred at 50 for 1 hour. The solution was poured into 100 ml ice water and extracted with ethyl acetate. The organic layer was washed with brine, dried over $Na_2SO_4$ and concentrated under reduced pressure to give methyl 3-methoxy-5-(2-methoxyethoxy)benzoate (0.5 g). The crude product was used in the next step without further purification.

ii) Following a procedure analogous to that described in Example 1, step iii, the title compound 3-methoxy-5-(2-methoxyethoxy)benzoic acid was prepared; MS (ESI) mz: 227 $(M+H)^+$.

Example 4

Intermediate Compound (R)-3-(2-hydroxypropoxy)-5-methoxybenzoic acid

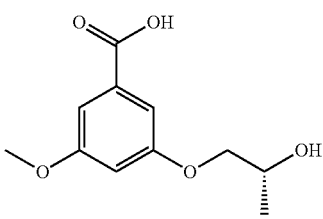 [SMILES: COc1cc(OC[C@@H](C)O)cc(C(=O)O)c1]

i) To a solution of compound methyl 3-hydroxy-5-methoxybenzoate (Example 1, step i, 90 mg, 0.5 mmol) and propylene oxide (120 mg, 2 mmol) in DMF (2 ml) was added $K_2CO_3$ (280 mg, 2 mmol). The reaction mixture was stirred at 100° C. overnight. After cooling to ambient temperature, the mixture was filtered and the filtrate was concentrated under reduced pressure. The obtained residue was purified using normal phase chromatography, eluting with petroleum ether containing 50% ethyl acetate to give (R)-methyl 3-(2-hydroxypropoxy)-5-methoxybenzoate (100 mg).

ii) To a solution of the product obtained in the previous step (100 mg, 0.42 mmol) in $CH_3OH$ (2 ml) was added a 2N aqueous solution of NaOH (1 mL). The reaction was heated to 60° C. for 2 hours. After cooling to ambient temperature the mixture was poured into water (10 ml) and the pH was adjusted to pH=4 by adding an aqueous solution of HCl. The product was extracted into ethyl acetate. The organic layer was washed with water, brine, dried over $Na_2SO_4$ and concentrated under reduced pressure to give the title compound 3-(2-hydroxypropoxy)-5-methoxybenzoic acid (60 mg) as an oil. MS (ESI) me: 227 $(M+H)^+$.

Example 5

Intermediate Compound

Following a procedure analogous to that described in Example 4, the following compound was prepared.

methyl 3-(2-hydroxy-2-methylpropoxy)-5-methoxybenzoate

MS (ESI) me: 241 $(M+H)^+$.

Example 6

Intermediate Compounds

Following a procedure analogous to that described in Example 4, using the appropriate alkylhalide, the following compounds were prepared.

6A: 3-methoxy-5-(3-methoxypropoxy)benzoic acid

MS (ESI) me: 241.2 $(M+H)^+$.

6B: 3-methoxy-5-propoxybenzoic acid

MS (ESI) me: 211.2 $(M+H)^+$.

6C: 3-methoxy-5-(prop-2-ynoxy)benzoic acid

MS (ESI) me: 207.2 $(M+H)^+$.

6D: 3-(2-aminoethoxy)-5-methoxybenzoic acid

MS (ESI) me: 212.2 $(M+H)^+$.

6E: 3-(2-amino-2-oxoethoxy)-5-methoxybenzoic acid

MS (ESI) me: 226.2 $(M+H)^+$.

6F: 3-isobutoxy-5-methoxybenzoic acid

MS (ESI) me: 224.2 $(M+H)^+$.

6G: 3-sec-butoxy-5-methoxybenzoic acid

MS (ESI) me: 224.2 $(M+H)^+$.

6H: 3-(2-hydroxyethoxy)-5-methoxybenzoic acid

MS (ESI) me: 213.2 $(M+H)^+$.

6I: 3-methoxy-5-(2,2,2-trifluoroethoxy)benzoic acid

MS (ESI) me: 251.1 $(M+H)^+$

6J: 3-(benzoxy)-5-methoxybenzoic acid; MS (ESI) me: 259.2 $(M+H)^+$

Example 7

Intermediate compound

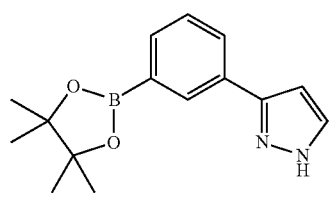 [SMILES: CC1(C)OB(c2cccc(-c3cc[nH]n3)c2)OC1(C)C]

3-(3-(4,4,5,5-tetramethyl-1,3,2-dioxaborolan-2-yl)phenyl)-1H-pyrazole i) To a stirred solution of 1-(3-bromophenyl)ethanone (4 g, 20 mmol) in EtOH (60 ml), was added at room temperature N,N-Dimethylformamide diethylacetal (7.15 g, 60 mmol) and the mixture was stirred at reflux temperature for 2 hours. After cooling to ambient temperature, the mixture was concentrated under reduced pressure. The residue was purified using normal phase chromatography, eluting with petroleum ether containing 50% ethyl acetate to give (Z)-1-(3-bromophenyl)-3-(dimethylamino)prop-2-en-1-one (3.0 g) as an oil.

ii) To a solution of the product obtained in the previous step (3 g, 11.8 mmol) in EtOH (50 ml) was added hydrazinehydrate (2.2 g, 35.4 mmol, 85%) at room temperature. The reaction mixture was stirred at reflux temperature for 1 hour. After cooling to ambient temperature, the mixture was concentrated and the residue was dissolved in $CH_2Cl_2$ (50 ml). The solution was washed with brine, dried over $Na_2SO_4$ and concentrated under reduced pressure to give 3-(3-bromophenyl)-1H-pyrazole (2.5 g) as yellow solid.

iii) A mixture of $Pd_2(dba)_3$ (183 mg, 0.20 mmol), $PCy_3$ (132 mg, 0.47 mmol) in dioxane was stirred for 30 mins at room temperature under a nitrogen atmosphere. Before the product obrained in the previous step (1.5 g, 6.73 mmol), bis(pinacolato)diboron (2.56 g, 10.1 mmol) and potassium acetate (1.32 g, 13.5 mmol) were added. The reaction mixture was stirred at reflux temperature 4 hours. After cooling to room temperature, the mixture was filtered and concentrated under reduced pressure. The residue was purified using normal phase chromatography, eluting with petroleum ether containing 10% ethyl acetate to give the title compound 3-(3-(4,4,5,5-tetramethyl-1,3,2-dioxaborolan-2-yl)phenyl)-1H-pyrazole (1.8 g).

MS (ESI) mz: 271.0 (M+H$^+$).

Example 8

Intermediate Compound 1-(3-(4,4,5,5-tetramethyl-1,3,2-dioxaborolan-2-yl)phenyl)-1H-pyrazole i) To a suspension of sodium hydride (3.52 g, 88 mmol) in DMF (40 ml), was added pyrazole (3.0 g, 44 mmol) in portions. After stirring at room temperature for 30 minutes, 1-bromo-3-fluorobenzene (9.3 g, 53 mmol) in DMF (20 ml) was added dropwise and the resulting mixture was stirred for 2 hours at 130° C. The mixture was cooled and quenched by the addition of a saturated aqueous $NH_4Cl$ solution and extracted with ethyl acetate. The organic layer was washed with brine, dried over $Na_2SO_4$ and concentrated under reduced pressure. The residue was purified using normal phase chromatography, eluting with petroleum ether containing 10% ethyl acetate to give 1-(3-bromophenyl)-1H-pyrazole (4.7 g) as yellow solid.

ii) Following a procedure analogous to that described in Example 7, step iii, the title compound 1-(3-(4,4,5,5-tetramethyl-1,3,2-dioxaborolan-2-yl)phenyl)-1H-pyrazole was prepared (5.4 g); $^1$H NMR (CDCl$_3$): δ 8.06 (d, 1H, J=1.32 Hz), 7.99 (d, 1H, J=2.36 Hz), 7.82-7.84 (m, 1H), 7.72 (d, 2H, J=2.56 Hz), 7.47 (t, 1H, J=8.02 Hz), 6.46 (t, 1H, J=2.24 Hz), 1.47 (s, 12H).

Example 9

Intermediate Compound

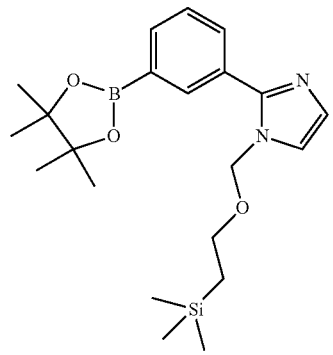 [SMILES: CC1(C)OB(c2cccc(-c3nccn3COCC[Si](C)(C)C)c2)OC1(C)C]

2-(3-(4,4,5,5-tetramethyl-1,3,2-dioxaborolan-2-yl)phenyl)-1-((2-(trimethylsilyl)ethoxy)methyl)-1H-imidazole i) To a suspension solution of sodium hydride (8.8 g, 221 mmol, 60% in mineral oil) in THF (100 ml), was added slowly imidazole (10 g, 147 mmol) in portions. After stirring the mixture for 30 minutes at room temperature, 2-(trimethysilyl)-ethoxymethyl chloride (29.3 g, 176 mmol) was added dropwise over 15 minutes. The reaction mixture was stirred at room temperature for 1 hour and quenched by the addition of water (50 ml). The product was extracted into ethyl acetate and the washed with brine, dried over $Na_2SO_4$ and concentrated under reduced pressure to 1((2-(trimethylsilyl)ethoxy)methyl)-1H-imidazole (34 g) as an oil. The crude product was used in the next step without further purification.

ii) To a stirred solution of the product obtained in the previous step (34 g, crude) in $CH_3CN$ (400 ml) was added cyanic bromide (40 g, 377 mmol) in portions. After stirring for 3 hours at room temperature, the mixture was diluted by the addition of water and the product was extracted into ethyl acetate. The combined organic layers were washed with brine, dried over $Na_2SO_4$, and concentrated under reduced pressure. The crude product was purified using normal phase chromatography, eluting with petroleum ether containing 10% ethyl acetate to give to give 2-bromo-1-((2-(trimethylsilyl)ethoxy)methyl)-1H-imidazole (10.5 g).

iii) To a stirred solution of the product obtained in the previous step (28 g, 101 mmol) in dioxane/water (450 ml, 3/1), were added under a nitrogen atmosphere, 3-bromophenylboronic acid (24.3 g, 121 mmol), $K_2CO_3$ (27.9 g, 202 mmol) and Pd(PPh$_3$)$_4$ (5.8 g, 5 mmol). The resulting mixture was stirred at reflux temperature for 4 hours. After cooling to ambient temperature, the mixture was filtered and the organic layer was separated and concentrated under reduced pressure. The crude product was purified using normal phase chromatography, eluting with petroleum ether containing 15% ethyl acetate, to give 2-(3-bromophenyl)-1((2-(trimethylsilyl)ethoxy)methyl)-1H-imidazole (15 g) as a colorless oil.

iv) Following a procedure analogous to that described in Example 7, step iii, the title compound 2-(3-(4,4,5,5-tetramethyl-1,3,2-dioxaborolan-2-yl)phenyl)-1-((2-(trimethylsilyl)ethoxy)methyl)-1H-imidazole was prepared (2.2 g). $^1$H NMR (CDCl$_3$): δ 8.15 (s, 1H), 7.85-7.80 (m, 2H), 7.64-7.64 (m, 1H), 7.45 (t, 1H, J=8.0 Hz), 7.14 (s, 1H), 7.12 (s, 1H), 5.27 (s, 2H), 3.50 (t, 2H, J=8.4 Hz), 1.23 (s, 12H), 0.90 (t, 2H, J=8.0 Hz), 0.00 (s, 9H)

Example 10

Intermediate Compound 3-(tert-butyldimethylsiloxy)-5-methoxyaniline i) To a solution of 3,5-dimethoxyaniline (2.53 g, 16.5 mmol) in N-methylpyrrolidinone (10 ml) was added sodium thiomethoxide (2.32 g, 33.1 mmol). The reaction mixture was heated to 140° C. for 2.5 hours and then stirred at ambient temperature for a further 18 hours. The mixture was poured into a saturated solution of NaH$_2$PO$_4$ (50 ml) and then extracted with ethyl acetate. The combined organic layers were filtered through a hydrophobic frit and the solvent was removed under reduced pressure to give a dark red oil. The crude residue was purified by normal phase chromatography, eluting with iso-hexane and increasing amounts of ethyl acetate to give 3-amino-5-methoxyphenol, as a pale yellow solid (1.53 g).

ii) To a solution of the product obtained in the previous step (950 mg, 6.83 mmol) in CH$_2$Cl$_2$ (50 ml) was added imidazole (2.32 g, 34.2 mmol) and t-butyldimethylsilyl chloride (3.1 g, 20.5 mmol). The resulting yellow suspension was stirred at ambient temperature for 16 hours. After completion, the solvent was removed under reduced pressure and the residue was partitioned between ethyl acetate and water. The organic phase was washed with a 1 N aqueous NaOH solution, water and brine. The organic phase was filtered through a hydrophobic frit and the solvent was removed under reduced pressure. The crude residue obtained was purified by normal phase chromatography, eluting with iso-hexane and increasing amounts of ethyl acetate to give 3-(tert-butyldimethylsiloxy)-5-methoxyaniline, as an off white oil (1.72 g). $^1$H NMR (CDCl$_3$): δ 5.70-5.62 (3H, m), 3.53 (3H, s), 3.41 (2H, s), 0.78 (8H, s), 0.09 (6H, s).

Example 11

N-((1-(2-(3-(1H-pyrazol-1-yl)phenyl)pyrimidin-4-yl)piperidin-4-yl)methyl)-3-(benzoxy)-5-methoxybenzamide

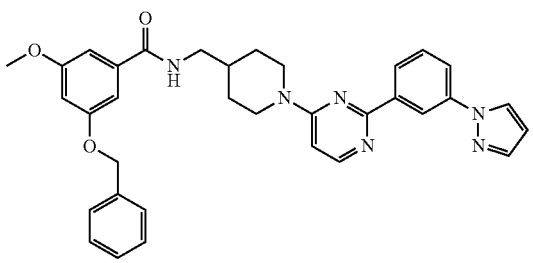 [SMILES: COc1cc(OCc2ccccc2)cc(C(=O)NCC2CCN(c3ccnc(-c4cccc(-n5cccn5)c4)n3)CC2)c1]

i) A solution of 4-N-Boc-aminomethylpiperidine (4.95 g, 23.1 mmol), 2,4-dichloropyrimidine (3.28 g, 22.0 mmol) and triethyl amine (7.84 g, 77.5 mmol) in ethanol (90 ml) was stirred at 85° C. for 45 minutes. The reaction mixture was concentrated under reduced pressure and the residue obtained was dissolved in CH$_2$Cl$_2$ and filtered. The solvent was removed under reduced pressure to give a crude residue that was purified using normal phase chromatography, eluting with iso-hexane and increasing amounts of ethyl acetate to give tert-butyl (1-(2-chloropyrimidin-4-yl)piperidin-4-yl)methylcarbamate as an off white solid (6.0 g).

ii) The product obtained in the previous step (5.92 g, 18.1 mmol), 3-pyrazolephenylboronic acid (3.41 g, 18.1 mmol), potassium carbonate (7.51 g, 54.3 mmol) and Pd(dppf)$_2$Cl$_2$ were dissolved in dioxane:water (150 ml, 9:1). After purging with N$_2$ for 15 minutes, the reaction mixture was heated to 85° C. for 2 hours and then cooled to ambient temperature. The solvents were removed under reduced pressure. The residue was partitioned between ethyl acetate and water. The organic phase was separated and concentrated under reduced pressure giving a dark solid (9.59 g). The crude solid was purified using normal phase chromatography eluting with iso-hexane and increasing amounts of ethyl acetate to give tert-butyl (1-(2-(3-(1H-pyrazol-1-yl)phenyl)pyrimidin-4-yl)piperidin-4-yl)methylcarbamate as a pink solid (6.05 g).

iii) A 4N solution of HCl in 1,4-dioxane (25 ml, 100 mmol) was added to a slurry of the product obtained in the previous step (4.60 g, 10.6 mmol) in CH$_2$Cl$_2$ (40 ml) and stirred for 48 hours at room temperature. The solvents were removed under vacuum to give an orange solid. The crude solid was triturated with 1:1 CH$_2$Cl$_2$:iso-hexane (40 ml) and dried under vacuum at 40° C. to give (1-(2-(3-(1H-pyrazol-1-yl)phenyl)pyrimidin-4-yl)piperidin-4-yl)methanamine hydrochloride as a pale orange solid (4.26 g).

iv) The product obtained in the previous step (0.80 g, 2.17 mmol) was added to a solution of 3-(benzoxy)-5-methoxybenzoic acid (0.56 g, 2.17 mmol), diisopropylethyl amine (0.69 g; 5.4 mmol) and HATU (0.98 g, 2.6 mmol) in DMF (15 ml) and stirred for 18 hours at room temperature. The reaction mixture was partitioned between ethyl acetate and water and the aqueous phase was extracted with ethyl acetate. The combined organics were washed with water, dried over Na$_2$SO$_4$ and then concentrated under reduced pressure to give a pale yellow oil (1.45 g). An aliquot (50 mg) was purified by reverse phase preparative HPLC to give the title compound N-((1-(2-(3-(1H-pyrazol-1-yl)phenyl)pyrimidin-4-yl)piperidin-4-yl)methyl)-3-(benzoxy)-5-methoxybenzamide as an off white solid. $^1$H NMR (CDCl$_3$): δ 8.80 (1H, s), 8.32-8.27 (3H, m), 7.98 (1H, d, J=7.91 Hz), 7.74 (1H, d, J=1.72 Hz), 7.57 (1H, t, J=7.95 Hz), 7.45-7.30 (5H, m), 6.98 (1H, t, J=1.71 Hz), 6.92 (1H, t, J=1.71 Hz), 6.66 (1H, t, J=2.24 Hz), 6.54-6.47 (2H, m), 6.29 (1H, s), 5.08 (2H, s), 4.62 (2H, s), 3.82 (3H, s), 3.40 (2H, t, J=6.43 Hz), 3.05 (2H, t, J=12.68 Hz), 2.08-1.88 (3H, m), 1.36 (2H, qd, J=12.35, 4.12 Hz).

Example 12

Following a procedure analogous to that described in Example 11, using the appropriate starting materials, the following compounds were prepared.

12A: 3-(benzoxy)-N-((1-(2-(3-chlorophenyl)pyrimidin-4-yl)piperidin-4-yl)methyl)-5-methoxybenzamide MS (ESI) me: 543.07 (M+H)+.

12B: 3-(benzoxy)-5-methoxy-N-((1-(4-(3-(pyridin-2-yl)phenyl)-1,3,5-triazin-2-yl)piperidin-4-yl)methyl)benzamide MS (ESI) me: 587.7 (M+H)+.

Example 13

N-((1-(2-(3-(1H-pyrazol-1-yl)phenyl)pyrimidin-4-yl)piperidin-4-yl)methyl)-3-hydroxy-5-methoxybenzamide i) A solution of N-((1-(2-(3-(1H-pyrazol-1-yl)phenyl)pyrimidin-4-yl)piperidin-4-yl)methyl)-3-(benzoxy)-5-methoxybenzamide (Example 11, step iv, 1.45 g, 2.5 mmol), ammonium formate (0.70 g, 11.1 mmol) and 10% palladium on carbon (0.15 g) in methanol (30 ml) was heated to reflux temperature for 18 hours. The reaction mixture was cooled to ambient temperature and filtered through celite. The filtrate was concentrated under reduced pressure and the residue obtained was partitioned between $CH_2Cl_2$ and water. The organic phase was passed through a hydrophobic frit and concentrated under reduced pressure to give N-((1-(2-(3-(1H-pyrazol-1-yl)phenyl)pyrimidin-4-yl)piperidin-4-yl)methyl)-3-hydroxy-5-methoxybenzamide as a pale yellow foam (1.16 g). MS (ESI) me: 485.6 (M+H)+.

Example 14

N-((1-(2-(3-(1H-pyrazol-1-yl)phenyl)pyrimidin-4-yl)piperidin-4-yl)methyl)-3-(4-fluorobenzoxy)-5-methoxybenzamide

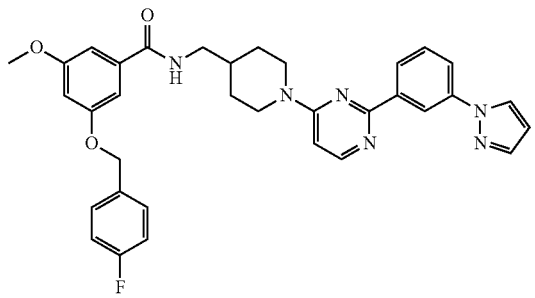 [SMILES: COc1cc(OCc2ccc(F)cc2)cc(C(=O)NCC2CCN(c3ccnc(-c4cccc(-n5cccn5)c4)n3)CC2)c1]

i) 4-Fluorobenzyl chloride (15 μl, 0.12 mmol) was added to a solution of N-((1-(2-(3-(1H-pyrazol-1-yl)phenyl)pyrimidin-4-yl)piperidin-4-yl)methyl)-3-hydroxy-5-methoxybenzamide (Example 13, 55 mg, 0.11 mmol) and cesium carbonate (80 mg, 0.24 mmol) in DMF (1 ml). The reaction mixture was heated to 40° C. for 5 hours. The solvent was removed under reduced pressure and the residue was partitioned between ethyl acetate and water. The aqueous phase was extracted with ethyl acetate and the combined organics were filtered through a hydrophobic frit and concentrated under reduced pressure. The crude residue was purified by normal phase chromatography, eluting with iso-hexane and increasing amounts of ethyl acetate to give the title compound N-((1-(2-(3-(1H-pyrazol-1-yl)phenyl)pyrimidin-4-yl)piperidin-4-yl)methyl)-3-(4-fluorobenzoxy)-5-methoxybenzamide as a white solid (42.5 mg). $^1$H NMR (CDCl$_3$): δ 8.64 (1H, t, J=1.88 Hz), 8.34-8.29 (2H, m), 8.06 (1H, d, J=2.48 Hz), 7.86 (1H, ddd, J=8.02, 2.33, 1.07 Hz), 7.74 (1H, d, J=1.74 Hz), 7.54 (1H, t, J=7.90 Hz), 7.43-7.37 (2H, m), 7.11-7.05 (2H, m), 6.96 (1H, t, J=1.75 Hz), 6.91 (1H, t, J=1.74 Hz), 6.65 (1H, t, J=2.25 Hz), 6.49-6.44 (2H, m), 6.21 (1H, t, J=6.08 Hz), 5.04 (2H, s), 4.60 (2H, s), 3.82 (3H, s), 3.39 (2H, t, J=6.43 Hz), 3.01-2.92 (2H, m), 2.04-1.88 (3H, m), 1.33 (2H, qd, J=12.28, 4.12 Hz).

Example 15

Following a procedure analogous to that described in Example 14, the following compounds were prepared.

15A: N-((1-(2-(3-(1H-pyrazol-1-yl)phenyl)pyrimidin-4-yl)piperidin-4-yl)methyl)-3-(cyclopropylmethoxy)-5-methoxybenzamide

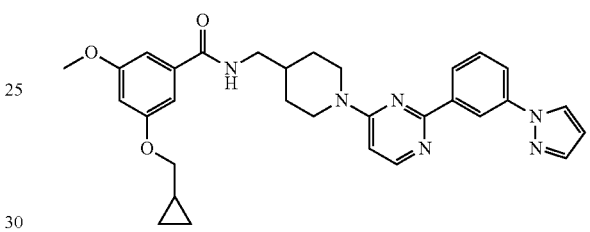

$^1$H NMR (CDCl$_3$): δ 8.64 (1H, t, J=1.88 Hz), 8.34-8.30 (2H, m), 8.06 (1H, d, J=2.48 Hz), 7.86 (1H, ddd, J=8.03, 2.33, 1.08 Hz), 7.74 (1H, d, J=1.74 Hz), 7.53 (1H, t, J=7.90 Hz), 6.89-6.86 (2H, m), 6.59 (1H, t, J=2.25 Hz), 6.49-6.44 (2H, m), 6.19 (1H, t, J=6.10 Hz), 4.59 (2H, s), 3.85-3.80 (5H, m), 3.39 (2H, t, J=6.42 Hz), 3.00-2.91 (2H, m), 2.04-1.88 (3H, m), 1.38-1.24 (3H, m), 0.68-0.62 (2H, m), 0.37-0.32 (2H, m).

15B: N-((1-(2-(3-(1H-pyrazol-1-yl)phenyl)pyrimidin-4-yl)piperidin-4-yl)methyl)-3-methoxy-5-((5-methylisoxazol-3-yl)methoxy)benzamide

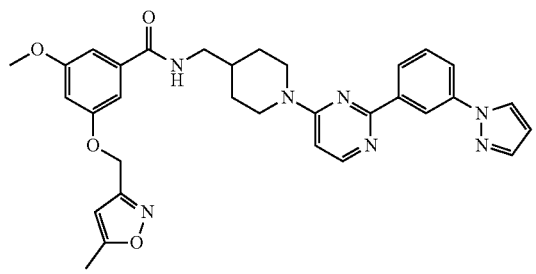 [SMILES: COc1cc(OCc2cc(C)on2)cc(C(=O)NCC2CCN(c3ccnc(-c4cccc(-n5cccn5)c4)n3)CC2)c1]

$^1$H NMR (CDCl$_3$): δ 8.63 (1H, t, J=1.84 Hz), 8.33-8.28 (2H, m), 8.06 (1H, d, J=2.48 Hz), 7.87-7.84 (1H, m), 7.74 (1H, d, J=1.73 Hz), 7.54 (1H, t, J=7.92 Hz), 7.01-6.95 (2H, m), 6.67 (1H, dt, J=9.64, 2.26 Hz), 6.50-6.45 (2H, m), 6.27 (1H, t, J=6.09 Hz), 6.09 (1H, s), 5.12 (2H, s), 4.60 (2H, s), 3.82 (3H, s), 3.39 (2H, t, J=6.41 Hz), 3.01-2.91 (2H, m), 2.43 (3H, s), 2.06-1.88 (3H, m), 1.39-1.24 (2H, m).

15C: N-((1-(2-(3-(1H-pyrazol-1-yl)phenyl)pyrimidin-4-yl)piperidin-4-yl)methyl)-3-(3-hydroxypropoxy)-5-methoxybenzamide

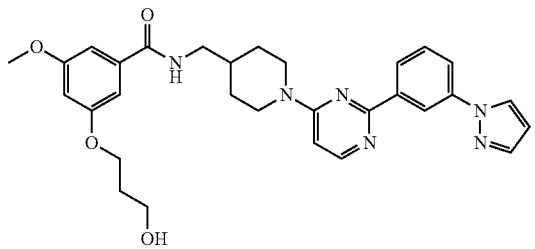 [SMILES: COc1cc(OCCCO)cc(C(=O)NCC2CCN(c3ccnc(-c4cccc(-n5cccn5)c4)n3)CC2)c1]

¹H NMR (DMSO): δ 8.89 (1H, s), 8.81 (1H, d, J=2.51 Hz), 8.68 (1H, t, J=5.77 Hz), 8.50 (1H, d, J=7.22 Hz), 8.32 (2H, dd, J=22.81, 7.97 Hz), 7.99 (1H, d, J=1.68 Hz), 7.89 (1H, t, J=7.99 Hz), 7.32 (1H, d, J=7.19 Hz), 7.17 (2H, d, J=7.69 Hz), 6.78 (2H, dt, J=4.14, 2.13 Hz), 4.6 (1H, broad peak), 4.22 (2H, t, J=6.38 Hz), 3.93 (3H, s), 3.72 (2H, t, J=6.41 Hz), 3.4 (4H, m), 2.16 (1H, m), 2.08-1.98 (4H, m), 1.48-1.38 (2H, m).

15D: N-((1-(2-(3-(1H-pyrazol-1-yl)phenyl)pyrimidin-4-yl)piperidin-4-yl)methyl)-3-methoxy-5-(2-methoxyethoxy)benzamide

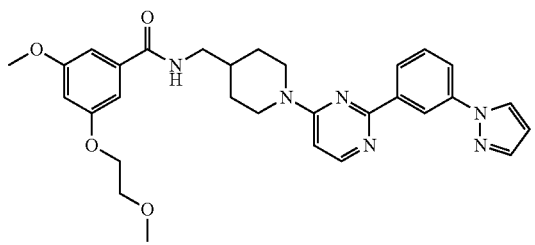 [SMILES: COCCOc1cc(OC)cc(C(=O)NCC2CCN(c3ccnc(-c4cccc(-n5cccn5)c4)n3)CC2)c1]

¹H NMR (CDl₃): δ 8.64 (1H, s), 8.34-8.29 (2H, m), 8.07 (1H, d, J=2.43 Hz), 7.87 (1H, dd, J=8.03, 2.14 Hz), 7.74 (1H, d, J=1.69 Hz), 7.54 (1H, t, J=7.91 Hz), 6.91 (2H, s), 6.62 (1H, t, J=2.22 Hz), 6.50-6.45 (2H, m), 6.20 (1H, t, J=6.07 Hz), 4.59 (2H, s), 4.14 (2H, t, J=4.53 Hz), 3.82 (3H, s), 3.75 (2H, t, J=4.52 Hz), 3.45 (3H, s), 3.39 (2H, t, J=6.40 Hz), 2.97 (2H, t, J=12.69 Hz), 1.91 (3H, d, J=13.73 Hz), 1.33 (2H, qd, J=12.20, 4.08 Hz).

Example 16

Following a procedure analogous to that described in Example 11, step iv, using the appropriate benzoic acid, the following compounds were prepared.

16A: N-((1-(2-(3-(1H-pyrazol-1-yl)phenyl)pyrimidin-4-yl)piperidin-4-yl)methyl)-3-methoxybenzamide MS (ESI) me: 469.56 (M+H)+.

16B: N-((1-(2-(3-(1H-pyrazol-1-yl)phenyl)pyrimidin-4-yl)piperidin-4-yl)methyl)-3,5-dichlorobenzamide MS (ESI) me: 507.4, 509.4 (M+H)+.

16C: N-((1-(2-(3-(1H-pyrazol-1-yl)phenyl)pyrimidin-4-yl)piperidin-4-yl)methyl)-3,5-dimethylbenzamide MS (ESI) me: 467.5 (M+H)+.

16D: N-((1-(2-(3-(1H-pyrazol-1-yl)phenyl)pyrimidin-4-yl)piperidin-4-yl)methyl)-3-methyl-5-(trifluoromethyl)benzamide MS (ESI) me: 521.5 (M+H)+.

Example 17

Following a procedure analogous to that described in Example 14, starting from 2,4-dichloro-1,3,5-triazine, the following compounds were prepared.

17A: N-((1-(4-(3-(1H-pyrazol-1-yl)phenyl)-1,3,5-triazin-2-yl)piperidin-4-yl)methyl)-3-(cyclopropylmethoxy)-5-methoxybenzamide

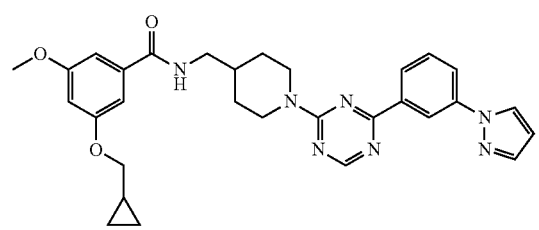 [SMILES: COc1cc(OCC2CC2)cc(C(=O)NCC2CCN(c3ncnc(-c4cccc(-n5cccn5)c4)n3)CC2)c1]

¹H NMR CDCl₃): δ 8.70-8.64 (2H, m), 8.34 (1H, d, J=7.83 Hz), 8.07 (1H, d, J=2.48 Hz), 7.94 (1H, dd, J=8.03, 2.21 Hz), 7.76 (1H, d, J=1.73 Hz), 7.57 (1H, t, J=7.94 Hz), 6.88 (2H, t, J=2.55 Hz), 6.59 (1H, t, J=2.25 Hz), 6.50 (1H, t, J=2.12 Hz), 6.20 (1H, t, J=6.02 Hz), 5.09 (1H, d, J=13.31 Hz), 4.91 (1H, d, J=13.18 Hz), 3.83 (5H, t, J=2.90 Hz), 3.39 (2H, d, J=6.09 Hz), 2.98 (2H, s), 1.93 (3H, s), 1.35-1.22 (3H, m), 0.69-0.63 (2H, m), 0.37-0.32 (2H, m).

17B: N-((1-(4-(3-(1H-pyrazol-1-yl)phenyl)-1,3,5-triazin-2-yl)piperidin-4-yl)methyl)-3-methoxy-5-((tetrahydro-2H-pyran-4-yl)methoxy)benzamide

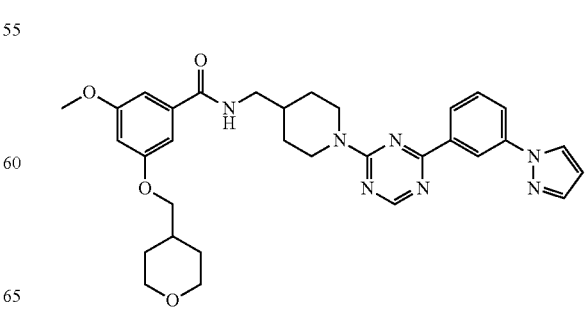

¹H NMR (CDCl₃): δ 8.69-8.65 (2H, m), 8.36-8.32 (1H, m), 8.06 (1H, d, J=2.46 Hz), 7.95-7.92 (1H, m), 7.76 (1H, d, J=1.73 Hz), 7.57 (1H, t, J=7.94 Hz), 6.88 (2H, d, J=2.21 Hz), 6.57 (1H, t, J=2.22 Hz), 6.50 (1H, t, J=2.10 Hz), 6.21 (1H, t, J=6.07 Hz), 5.01 (2H, dd, J=72.55, 13.02 Hz), 4.02 (2H, dd, J=11.45, 4.20 Hz), 3.86-3.81 (5H, m), 3.49-3.38 (4H, m), 2.98 (3H, s), 2.04 (2H, s), 1.93 (2H, s), 1.75 (2H, d, J=13.30 Hz), 1.32 (4H, s).

17C: N-((1-(4-(3-(1H-pyrazol-1-yl)phenyl)-1,3,5-triazin-2-yl)piperidin-4-yl)methyl)-3-(furan-3-yl)methoxy)-5-methoxybenzamide

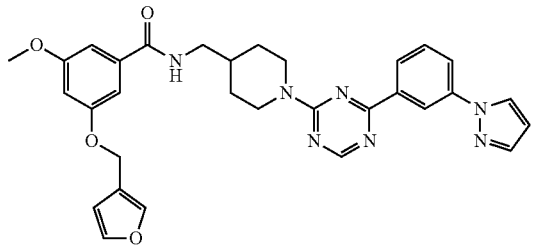 [SMILES: COc1cc(OCc2ccoc2)cc(C(=O)NCC2CCN(c3ncnc(-c4cccc(-n5cccn5)c4)n3)CC2)c1]

MS (ESI) me: 566.1 (M+H)+.

17D: N-((1-(4-(3-(1H-pyrazol-1-yl)phenyl)-1,3,5-triazin-2-yl)piperidin-4-yl)methyl)-3-methoxy-5-(2-(methylamino)-2-oxoethoxy)benzamide

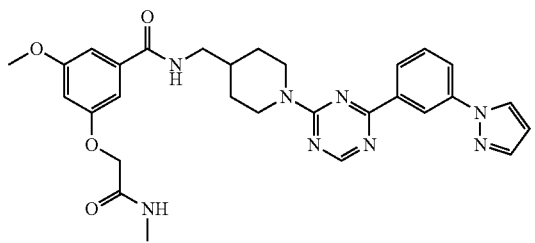 [SMILES: CNC(=O)COc1cc(OC)cc(C(=O)NCC2CCN(c3ncnc(-c4cccc(-n5cccn5)c4)n3)CC2)c1]

MS (ESI) me: 557.63 (M+H)+.

17E: N-((1-(4-(3-(1H-pyrazol-1-yl)phenyl)-1,3,5-triazin-2-yl)piperidin-4-yl)methyl)-3-(benzoxy)-5-(trifluoromethyl)benzamide

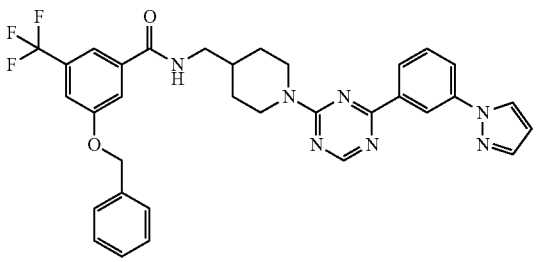 [SMILES: O=C(NCC1CCN(c2ncnc(-c3cccc(-n4cccn4)c3)n2)CC1)c1cc(OCc2ccccc2)cc(C(F)(F)F)c1]

MS (ESI) me: 614.63 (M+H)+.

Example 18

N-((1-(2-(3-(1H-pyrazol-5-yl)phenyl)pyrimidin-4-yl)piperidin-4-yl)methyl)-3,5-dimethoxybenzamide

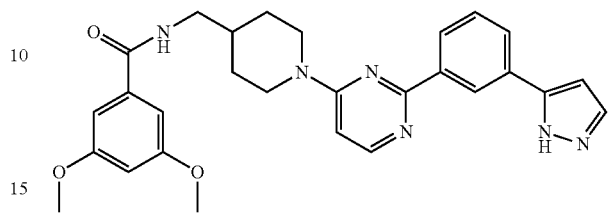

i) To a solution of (1-(2-chloropyrimidin-4-yl)piperidin-4-yl)methylcarbamate (Example 11, step i, 2.32 g, 6.73 mmol) in CH₂Cl₂ (30 ml) was added trifluoroacetic acid (6.0 ml, 81 mmol). After stirring for 3 h at room temperature the solvents were removed under reduced pressure to give (1-(2-chloropyrimidin-4-yl)piperidin-4-yl)methanamine 2,2,2-trifluoroacetate as a white solid (1.71 g). The crude product was used in the next step without further purification.

ii) A suspension of the product obtained in the previous step (2.360 g, 10.41 mmol), 3,5-dimethoxybenzoic acid (1.58 g, 8.67 mmol) and N,N-diisopropylethyl amine (3.51 ml, 21.25 mmol) were suspended in CH₂Cl₂ (70 ml). After stirring for 15 minutes at room temperature, HATU (3.96 g, 10.41 mmol) was added and the reaction mixture was stirred for a further 4 h. The reaction mixture was quenched by the addition of a saturated aqueous solution of NaHCO3 and the product was extracted with CH₂Cl₂:CH₃OH (9:1). The organic layer was dried over Na₂SO₄ and concentrated under reduced pressure.

The crude residue was purified by normal phase chromatography, eluting with heptane and increasing amounts of ethyl acetate to afford N-((1-(2-chloropyrimidin-4-yl)piperidin-4-yl)methyl)-3,5-dimethoxybenzamide as a white solid (3.6 g).

iii) A solution of the product obtained in the previous step (100 mg, 0.256 mmol), 3-(1H-pyrazol-5-yl)phenylboronic acid (96 mg, 0.512 mmol) and a 2N aqueous solution of potassium carbonate (384 μl, 0.768 mmol) in dioxane (3 ml) was purged with N₂ for 10 minutes. Tetrakis(triphenylphosphine)palladium(0) (14.78 mg, 0.013 mmol) was added and the reaction mixture was stirred at 150° C. in a microwave reactor for 10 minutes. The reaction mixture was diluted with CH₂Cl₂ and washed with brine. The organic layer was dried over Na₂SO₄, filtered and concentrated under reduced pressure. The crude residue was purified by normal phase chromatography, eluting with CH₂Cl₂ and increasing amounts of CH₃OH to afford the title compound N-((1-(2-(3-(1H-pyrazol-5-yl)phenyl)pyrimidin-4-yl)piperidin-4-yl)methyl)-3,5-dimethoxybenzamide (58 mg) as a white solid. MS (ESI) me: 499.2 (M+H)+.

Example 19

Following a procedure analogous to that described in Example 18, using the appropriate starting materials, the following compounds were prepared.

19A: N-((1-(2-(3-(1H-pyrazol-5-yl)phenyl)pyrimidin-4-yl)piperidin-4-yl)methyl)-3-(cyclopropylmethoxy)-5-methoxybenzamide

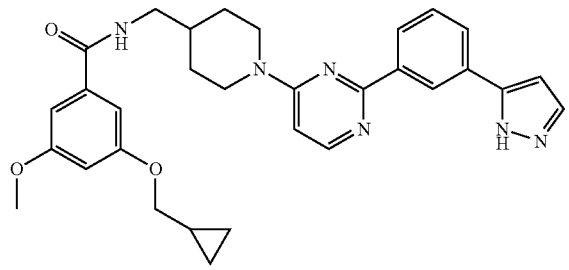 [SMILES: COc1cc(OCC2CC2)cc(C(=O)NCC2CCN(c3ccnc(-c4cccc(-c5ccn[nH]5)c4)n3)CC2)c1]

$^1$H NMR (CDCl$_3$): δ 8.72 (t, 1H), 8.35 (d, 1H), 8.29 (d, 1H), 7.83 (d, 1H), 7.65 (d, 1H), 7.50 (t, 1H), 6.89 (t, 2H), 6.61 (d, 1H), 6.59 (t, 1H), 6.44 (d, 1H), 6.30 (t, 1H), 4.58 (m, 2H), 3.82 (s, 3H), 3.82 (d, 2H), 3.37 (t, 2H), 2.94 (t, 2H), 1.97 (m, 1H), 1.89 (d, 2H), 1.28 (m, 2H), 0.88 (m, 1H), 0.65 (m, 2H), 0.35 (m, 2H)

19B: N-((1-(2-(3-cyanophenyl)-5-fluoropyrimidin-4-yl)piperidin-4-yl)methyl)-3-(cyclopropylmethoxy)-5-methoxybenzamide

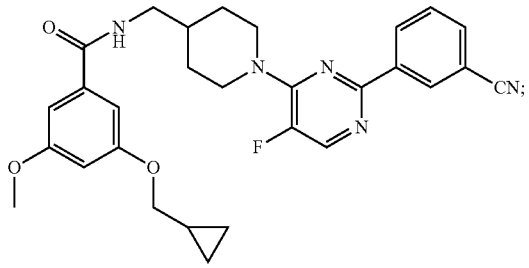 [SMILES: COc1cc(OCC2CC2)cc(C(=O)NCC2CCN(c3nc(-c4cccc(C#N)c4)ncc3F)CC2)c1]

MS (ESI) me: 516.0 (M+H)+.

19C: N-((1-(2-(3-(1H-pyrazol-5-yl)phenyl)-5-fluoropyrimidin-4-yl)piperidin-4-yl)methyl)-3-(cyclopropylmethoxy)-5-methoxybenzamide

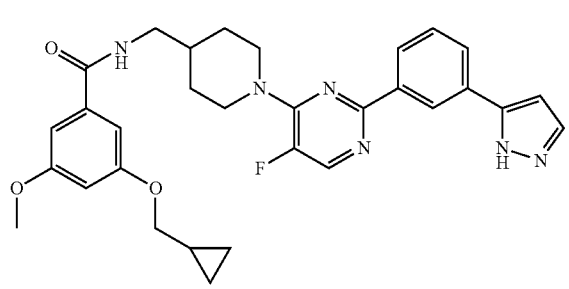 [SMILES: COc1cc(OCC2CC2)cc(C(=O)NCC2CCN(c3nc(-c4cccc(-c5ccn[nH]5)c4)ncc3F)CC2)c1]

$^1$H NMR (CDCl$_3$): δ 8.66 (s, 1H), 8.28 (dt, 1H), 8.16 (d, 1H), 7.83 (d, 1H), 7.65 (d, 1H), 7.50 (t, 1H), 6.88 (m, 2H), 6.71 (d, 1H), 6.59 (t, 1H), 6.23 (t, NH), 4.72 (d, 2H), 3.82 (m, 2H), 3.82 (s, 3H), 3.39 (t, 2H), 3.10-3.00 (t, 2H), 2.00 (m, 1H), 1.90 (m, 2H), 1.40 (m, 2H)

19D: 3-(4-(4-((3-(cyclopropyl methoxy)-5-methoxybenzamido)methyl)piperidin-1-yl)pyrimidin-2-yl)benzoic acid

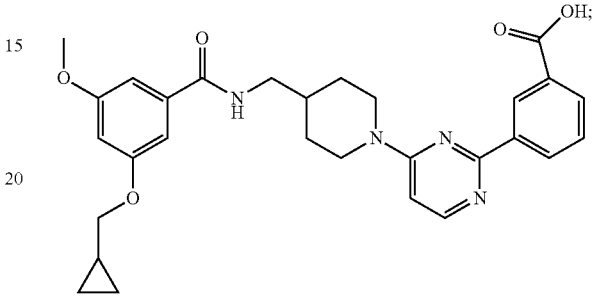

MS (ESI) me: 517.3 (M+H)+.

19E: N-((1-(2-(1H-indazol-5-yl)pyrimidin-4-yl)piperidin-4-yl)methyl)-3-(cyclopropylmethoxy)-5-methoxybenzamide

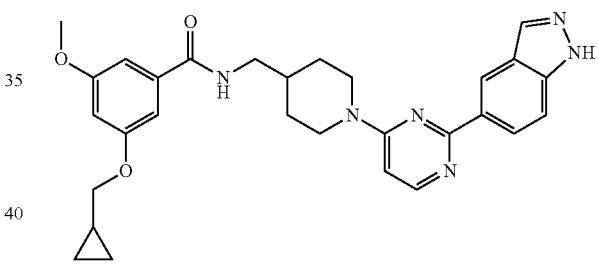

NMR (CDCl$_3$): δ 8.78 (m, 1H), 8.48 (t, 1H), 8.37 (m, 1H), 8.27 (d, 1H), 8.19 (s, 1H), 7.57 (m, 1H), 6.89 (m, 2H), 6.74 (d, 1H), 6.63 (t, 1H), 4.55 (m, 2H), 3.54 (d, 2H), 3.76 (s, 3H), 3.18 (t, 2H), 2.95 (t, 2H), 1.95 (m, 1H), 1.79 (m, 2H), 1.16 (m, 3H), 0.58 (m, 2H), 0.33 (m, 2H)

19F: 3-(cyclopropyl methoxy)-5-methoxy-N-((1-(2-(1-methyl-1H-indazol-6-yl)pyrimidin-4-yl)piperidin-4-yl)methyl)benzamide

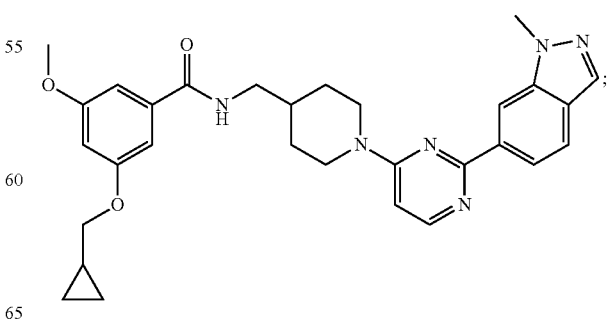

MS (ESI) me: 527.3 (M+H)+.

19G: 3-(cyclopropyl methoxy)-5-methoxy-N-((1-(2-(1-methyl-1H-indazol-4-yl)pyrimidin-4-yl)piperidin-4-yl)methyl)benzamide

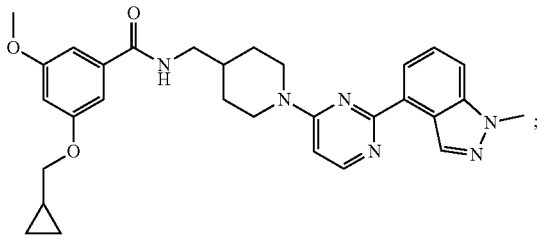 [SMILES: COc1cc(OCC2CC2)cc(C(=O)NCC2CCN(c3ccnc(-c4cccc5c4cnn5C)n3)CC2)c1]

MS (ESI) me: 527.3 (M+H)+

Example 20

Following a procedure analogous to that described in Example 18, using the appropriate phenylboronic acid and piperidin-4-ylmethanamine analogous, the following compounds were prepared.

20A: methyl 2-(1-(2-(3-(1H-pyrazol-1-yl)phenyl)pyrimidin-4-yl)piperidin-4-yl)-2-(3,5-dimethoxybenzamido)acetate

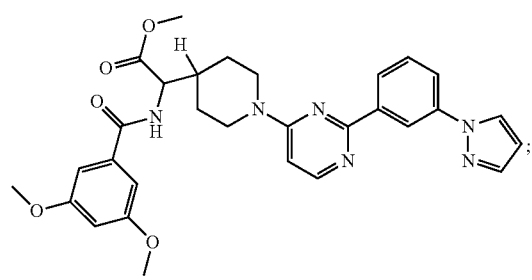 [SMILES: COC(=O)C(NC(=O)c1cc(OC)cc(OC)c1)C1CCN(c2ccnc(-c3cccc(-n4cccn4)c3)n2)CC1]

MS (ESI) me: 557.3 (M+H)+

20B: N-(7-(2-(3-(1H-pyrazol-1-yl)phenyl)pyrimidin-4-yl)-7-azaspiro[3.5]nonan-1-yl)-3,5-dimethoxybenzamide

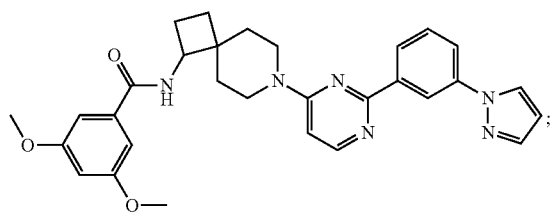 [SMILES: COc1cc(OC)cc(C(=O)NC2CCC23CCN(c2ccnc(-c4cccc(-n5cccn5)c4)n2)CC3)c1]

MS (ESI) me: 525.3 (M+H)+.

20C: N-((1-(2-(3-(1H-pyrazol-1-yl)phenyl)pyrimidin-4-yl)-4-methylpiperidin-4-yl)methyl)-3,5-dimethoxybenzamide

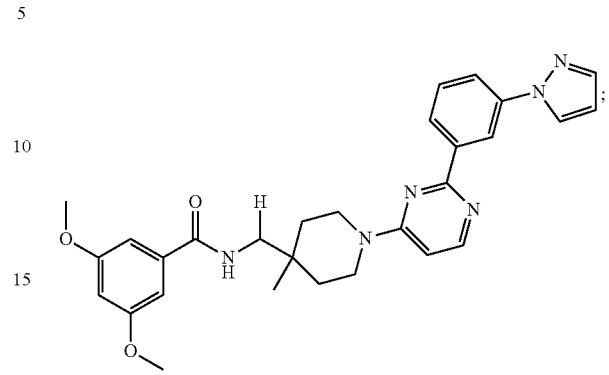

MS (ESI) me: 513.3 (M+H)+.

20D: N-((1-(2-(3-(1H-pyrazol-1-yl)phenyl)pyrimidin-4-yl)-4-fluoropiperidin-4-yl)methyl)-3,5-dimethoxybenzamide

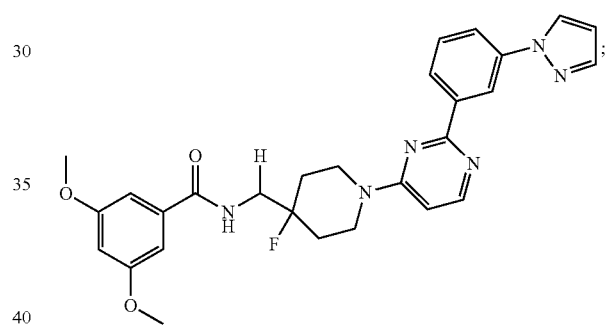

MS (ESI) me: 517.2 (M+H)+.

Example 21

Following a procedure analogous to that described in Example 18, using the appropriate phenylboronic acid and 2,4-dichloropyrimidine, the following compounds were prepared.

21A: N-((1-(2-(3-(1H-pyrazol-1-yl)phenyl)-5-cyanopyrimidine-4-yl)piperidin-4-yl)methyl)-3,5-dimethoxybenzamide

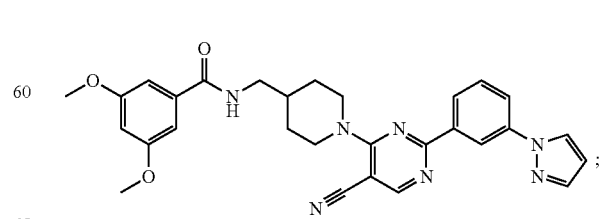

MS (ESI) me: 524.3 (M+H)+.

21B: methyl 2-(3-(1H-pyrazol-1-yl)phenyl)-4-(4-((3,5-dimethoxybenzamido)methyl)piperidin-1-yl)pyrimidine-5-carboxylate

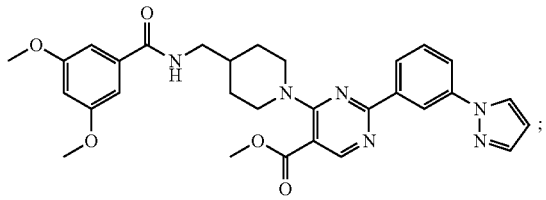 [SMILES: COC(=O)c1cnc(-c2cccc(-n3cccn3)c2)nc1N1CCC(CNC(=O)c2cc(OC)cc(OC)c2)CC1]

MS (ESI) me: 557.8 (M+H)+.

21C: N-((1-(2-(3,5-dichlorophenyl)pyrimidin-4-yl)piperidin-4-yl)methyl)-3,5-dimethoxybenzamide

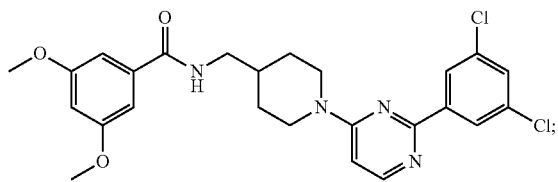 [SMILES: COc1cc(OC)cc(C(=O)NCC2CCN(c3ccnc(-c4cc(Cl)cc(Cl)c4)n3)CC2)c1]

MS (ESI) me: 501.1, 503.2 (M+H)+.

21D: N-((1-(2-(1H-indol-6-yl)pyrimidin-4-yl)piperidin-4-yl)methyl)-3,5-dimethoxybenzamide

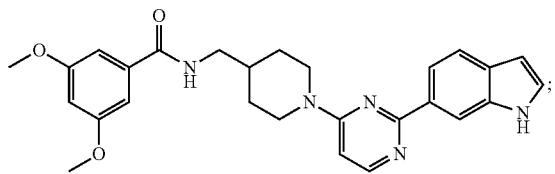 [SMILES: COc1cc(OC)cc(C(=O)NCC2CCN(c3ccnc(-c4ccc5cc[nH]c5c4)n3)CC2)c1]

MS (ESI) me: 472.6 (M+H)+.

Example 22

N-((1-(2-(3-(1H-pyrazol-3-yl)phenyl)-5-fluoropyrimidin-4-yl)piperidin-4-yl)methyl)-3-(2-hydroxyethoxy)-5-methoxybenzamide

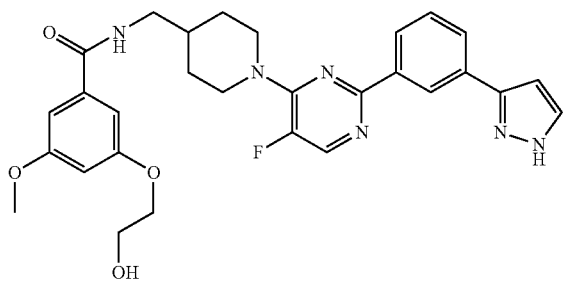 [SMILES: COc1cc(OCCO)cc(C(=O)NCC2CCN(c3nc(-c4cccc(-c5cc[nH]n5)c4)ncc3F)CC2)c1]

i) A solution of 4-N-Boc-aminomethylpiperidine (10 g, 47 mmol), 2,4-dichloropyrimidine (7.8 g, 47 mmol) and triethyl amine (10 g, 100 mmol) in ethanol (100 ml) was stirred at room temperature for 2 hours. The solvent was removed under reduced pressure to give a crude residue that was purified using normal phase chromatography, eluting with petroleum ether with 10% of ethyl acetate to give tert-butyl (1-(2-chloro-5-fluoropyrimidin-4-yl)piperidin-4-yl)methylcarbamate as an off white solid (16 g).

ii) To a suspension of the product obtained in the previous step (1 g, 2.9 mmol), 3-(3-(4,4,5,5-tetramethyl-1,3,2-dioxaborolan-2-yl)phenyl)-1H-pyrazole (0.8 g, 3.0 mmol) in $CH_3CN$ (6 ml) and a 2N aqueous solution of $Na_2CO_3$ (4 ml, 8 mmol) was added $Pd(dppf)_2Cl_2$ under a nitrogen atmosphere. After purging with $N_2$ for 15 minutes, the reaction mixture was heated to 135° C. for 10 minutes in a microwave reactor. After cooling to ambient temperature, the solvents were removed under reduced pressure and the obtained residue was purified using normal phase chromatography eluting with petroleum ether with 25% of ethyl acetate to give tert-butyl (1-(2-(3-(1H-pyrazol-3-yl)phenyl)-5-fluoropyrimidin-4-yl)piperidin-4-yl)methylcarbamate as a off white solid (0.3 g).

iii) To a solution of the product obtained in the previous step (0.3 g, 0.66 mmol) in ethyl acetate (2 ml) was added a 6N solution of HCl in ethyl acetate (1 ml). The reaction mixture was stirred at room temperature for 30 minutes and the solvents were removed under reduced pressure to give (1-(2-(3-(1H-pyrazol-3-yl)phenyl)-5-fluoropyrimidin-4-yl)piperidin-4-yl)methanamine hydrochloride as a white solid (0.18 g). The crude product was used in the next step without further purification.

iv) To a solution of the product obtained in the previous step (54 mg, 0.14 mmol), 3-(2-hydroxyethoxy)-5-methoxybenzoic acid (Example 6H, 30 mg, 0.14 mmol), triethyl amine (30 mg, 0.3 mmol) in DMF (2 ml) was added HATU (54 mg, 0.14 mmol) and the reaction mixture was stirred for 2 hours at room temperature. The solvent was removed under reduced pressure and the product was purified by reverse phase preparative HPLC to give the title compound N-((1-(2-(3-(1H-pyrazol-3-yl)phenyl)-5-fluoropyrimidin-4-yl)piperidin-4-yl)methyl)-3-(2-hydroxyethoxy)-5-methoxybenzamide as a white solid (10 mg).

$^1H$ NMR ($CD_3OD$): δ 8.54 (s, 1H), 8.31 (d, 1H, J=8.0 Hz), 8.08 (d, 1H, J=8.0 Hz), 7.99 (d, 1H, J=8.0 Hz), 7.72 (d, 1H, J=2.4 Hz), 7.60 (t, 1H, J=8.0 Hz), 6.97-6.98 (m, 2H), 6.76 (d, 1H, J=2.4 Hz), 6.66 (t, 1H, J=2.0 Hz), 4.85-4.91 (m, 2H), 4.05 (t, 2H, J=4.4 Hz), 3.85 (t, 2H, J=4.8 Hz), 3.80 (s, 3H), 3.26-3.32 (m, 4H), 2.07-2.12 (m, 1H), 1.97-2.01 (m, 2H), 1.40-1.50 (m, 2H).

Following a procedure analogous to that described in Example 22, the following compounds were prepared.

Example 23

23A: N-((1-(2-(3-(1H-pyrazol-3-yl)phenyl)-5-fluoro-pyrimidin-4-yl)piperidin-4-yl)methyl)-3-methoxy-5-(3-methoxypropoxy)benzamide

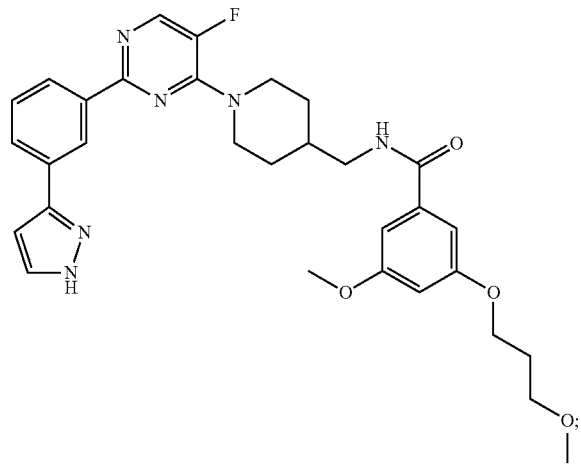 [SMILES: COCCCOc1cc(OC)cc(C(=O)NCC2CCN(c3nc(-c4cccc(-c5cc[nH]n5)c4)ncc3F)CC2)c1]

MS (ESI) me: 575.6 (M+H)+.

23B: N-((1-(2-(3-(1H-pyrazol-3-yl)phenyl)-5-fluoro-pyrimidin-4-yl)piperidin-4-yl)methyl)-3-methoxy-5-propoxybenzamide

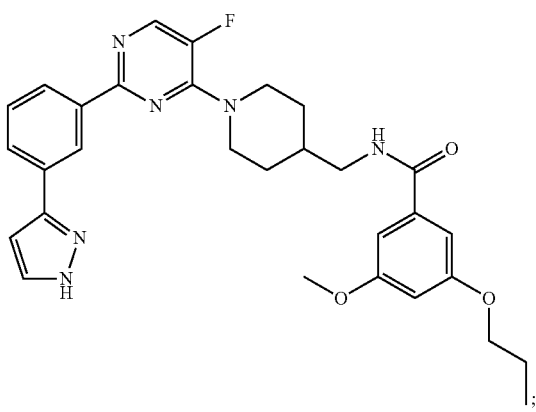 [SMILES: CCCOc1cc(OC)cc(C(=O)NCC2CCN(c3nc(-c4cccc(-c5cc[nH]n5)c4)ncc3F)CC2)c1]

MS (ESI) me: 545.6 (M+H)+.

23C: N-((1-(2-(3-(1H-pyrazol-3-yl)phenyl)-5-fluoro-pyrimidin-4-yl)piperidin-4-yl)methyl)-3-methoxy-5-(prop-2-ynoxy)benzamide

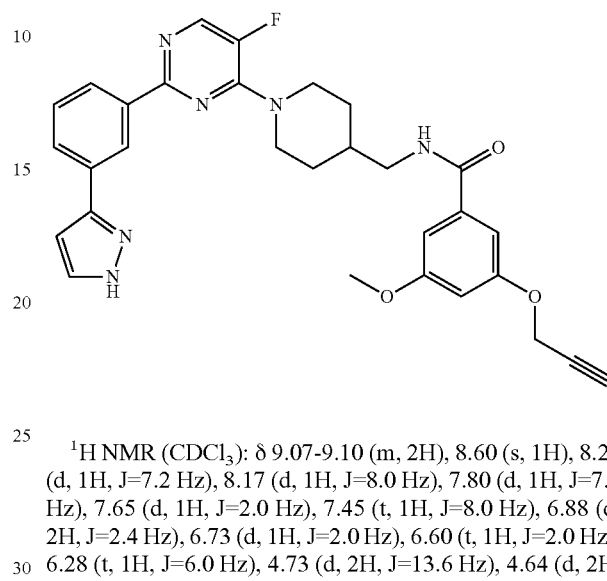

$^1$H NMR (CDCl$_3$): δ 9.07-9.10 (m, 2H), 8.60 (s, 1H), 8.24 (d, 1H, J=7.2 Hz), 8.17 (d, 1H, J=8.0 Hz), 7.80 (d, 1H, J=7.6 Hz), 7.65 (d, 1H, J=2.0 Hz), 7.45 (t, 1H, J=8.0 Hz), 6.88 (d, 2H, J=2.4 Hz), 6.73 (d, 1H, J=2.0 Hz), 6.60 (t, 1H, J=2.0 Hz), 6.28 (t, 1H, J=6.0 Hz), 4.73 (d, 2H, J=13.6 Hz), 4.64 (d, 2H, J=2.4 Hz), 3.76 (s, 3H), 3.33 (t, 2H, J=6.4 Hz), 3.07 (t, 2H, J=12.0 Hz), 2.47 (t, 1H, J=2.4 Hz), 1.98-1.99 (m, 1H), 1.89 (d, 2H, J=13.2 Hz), 1.32-1.41 (m, 2H).

23D: N-((1-(2-(3-(1H-pyrazol-3-yl)phenyl)-5-fluoro-pyrimidin-4-yl)piperidin-4-yl)methyl)-3-(2-aminoethoxy)-5-methoxybenzamide hydrochloride

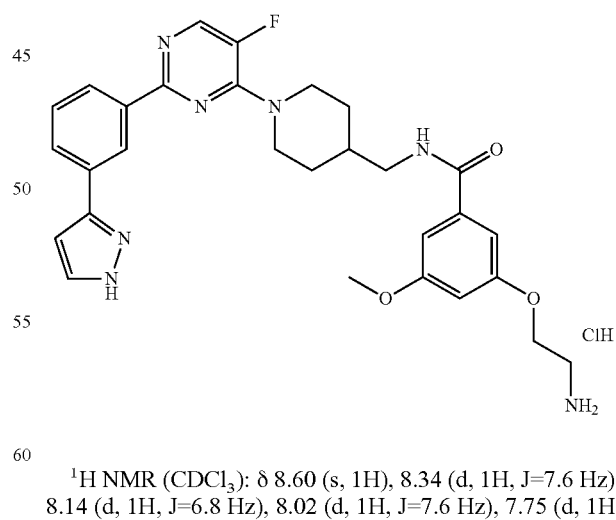

$^1$H NMR (CDCl$_3$): δ 8.60 (s, 1H), 8.34 (d, 1H, J=7.6 Hz), 8.14 (d, 1H, J=6.8 Hz), 8.02 (d, 1H, J=7.6 Hz), 7.75 (d, 1H, J=2.4 Hz), 7.62 (t, 1H, J=7.6 Hz), 7.08 (d, 2H, J=2.0 Hz), 6.76-6.80 (m, 2H), 4.90-4.91 (m, 2H), 4.32 (t, 2H, J=4.8 Hz), 3.86 (s, 3H), 3.48 (t, 2H, J=5.2 Hz), 3.28-3.37 (m, 4H), 2.82 (s, 3H), 2.12-2.15 (m, 1H), 2.02 (d, 2H, J=12.0 Hz), 1.45-1.54 (m, 2H).

23E: N-((1-(2-(3-(1H-pyrazol-3-yl)phenyl)-5-fluoro-pyrimidin-4-yl)piperidin-4-yl)methyl)-3-(2-amino-2-oxoethoxy)-5-methoxybenzamide

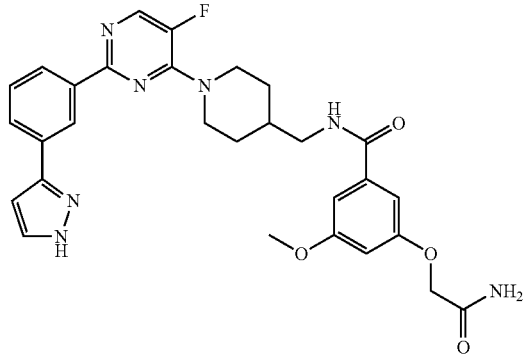 [SMILES: COc1cc(OCC(N)=O)cc(C(=O)NCC2CCN(c3nc(-c4cccc(-c5cc[nH]n5)c4)ncc3F)CC2)c1]

¹H NMR (CDCl₃): δ 8.65 (s, 1H), 8.48 (t, 1H, J=5.6 Hz), 8.34 (d, 1H, J=6.8 Hz), 8.14 (d, 1H, J=7.6 Hz), 7.86 (d, 1H, J=8.0 Hz), 7.72 (d, 1H, J=2.0 Hz), 7.46-7.50 (m, 2H), 7.37 (s, 1H), 7.00 (d, 2H, J=2.0 Hz), 6.71 (d, 1H, J=2.0 Hz), 6.65 (t, 1H, J=2.0 Hz), 4.54 (d, 2H, J=12.8 Hz), 4.42 (s, 2H), 3.74 (s, 3H), 3.06-3.16 (m, 4H), 1.79-1.94 (m, 3H), 1.22-1.30 (m, 2H).

23F: (S)—N-((1-(2-(3-(1H-pyrazol-3-yl)phenyl)-5-fluoropyrimidin-4-yl)piperidin-4-yl)methyl)-3-(2-hydroxypropoxy)-5-methoxybenzamide

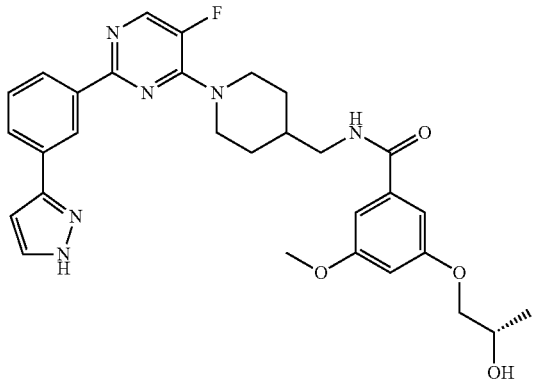 [SMILES: COc1cc(OC[C@H](C)O)cc(C(=O)NCC2CCN(c3nc(-c4cccc(-c5cc[nH]n5)c4)ncc3F)CC2)c1]

¹H NMR (CD₃OD): δ 8.57 (s, 1H), 8.35 (d, 1H, J=8.0 Hz), 8.11 (d, 1H, J=8.0 Hz), 8.03 (d, 1H, J=8.0 Hz), 7.75 (d, 1H, J=2.4 Hz), 7.62 (t, 1H, J=8.0 Hz), 7.00 (d, 2H, J=2.0 Hz), 6.79 (d, 1H, J=2.0 Hz), 6.69 (t, 1H, J=2.0 Hz), 4.89-4.95 (m, 2H), 4.09-4.14 (m, 1H), 3.88-3.94 (m, 2H), 3.83 (s, 3H), 3.31-3.35 (m, 4H), 2.12-2.15 (m, 1H), 2.02 (d, 2H, J=13.2 Hz), 1.44-1.54 (m, 2H), 1.28 (d, 3H, J=6.4 Hz).

23G: N-((1-(2-(3-(1H-pyrazol-3-yl)phenyl)-5-fluoro-pyrimidin-4-yl)piperidin-4-yl)methyl)-3-(2-hydroxy-2-methylpropoxy)-5-methoxybenzamide

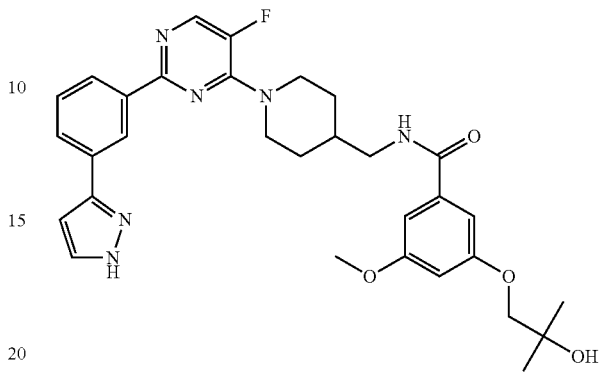

¹H NMR (CD₃OD): δ 8.54 (s, 1H), 8.33 (d, 1H, J=8.0 Hz), 8.07 (d, 1H, J=7.6 Hz), 8.01 (d, 1H, J=7.6 Hz), 7.72 (d, 1H, J=2.4 Hz), 7.60 (t, 1H, J=8.0 Hz), 6.97-6.99 (m, 2H), 6.76 (d, 1H, J=2.4 Hz), 6.67 (t, 1H, J=2.0 Hz), 4.88-4.92 (m, 2H), 3.80 (s, 3H), 3.79 (s, 2H), 3.28-3.32 (m, 4H), 2.07-2.10 (m, 1H), 1.98-2.01 (m, 2H), 1.41-1.50 (m, 2H), 1.30 (s, 6H).

Example 24

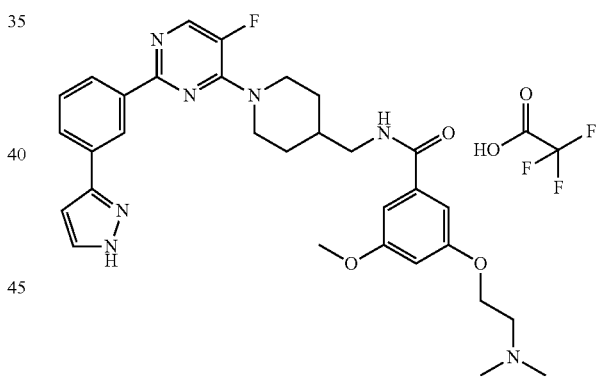

N-((1-(2-(3-(1H-pyrazol-3-yl)phenyl)-5-fluoropyri-midin-4-yl)piperidin-4-yl)methyl)-3-(2-(dimethy-lamino)ethoxy)-5-methoxybenzamide 2,2,2-trifluoroacetate i) To a solution of methyl 3-hydroxy-5-methoxybenzoate (1.82 g, 10 mmol) and 2-bromoethanol (2.5 g, 20 mmol) in CH₃CN (20 ml) was added K₂CO₃ (4.2 g, 0.03 mol) and the reaction mixture was heated to 80° C. overnight. After to cooling to room temperature, the reaction mixture was filtered and the filtrate was concentrated under reduced pressure. The obtained residue was purified using normal phase chromatography eluting with petroleum ether and increasing amounts of ethyl acetate to give compound methyl 3-(2-hydroxyethoxy)-5-methoxybenzoate (1.0 g).

ii) To a solution of the product obtained in the previous step (0.46 g, 2.0 mmol) and triethyl amine (0.5 g, 5.0 mmol) in CH$_2$Cl$_2$ (10 ml) was added methanesulfonyl chloride (360 mg, 3.0 mmol) and the reaction mixture was stirred at room temperature for 2 hours. After completion, the solution was washed with water, brine, dried over Na$_2$SO$_4$ and the solvent was removed under reduced pressure to give methyl 3-methoxy-5-(2-(methylsulfonoxy)ethoxy)benzoate (600 mg) as a clear oil. The crude product was used in the next step without further purification.

iii) To a solution of the product obtained in the previous step (500 mg, 1.64 mmol) in CH$_3$OH (10 ml) was added a 2N aqueous solution of NaOH (5 ml) and the reaction mixture was stirred at room temperature overnight. The reaction mixture was poured into 50 ml of water and the pH was adjusted to pH=4 by addition of an aqueous solution of HCl. The product was extracted into ethyl acetate and the combined organic layers were concentrated under reduced pressure to give 3-methoxy-5-(2-(methylsulfonoxy)ethoxy)benzoic acid (300 mg). The crude product was used in the next step without further purification.

iv) To a solution of the product obtained in the previous step (300 mg, 1.03 mmol), (1-(2-(3-(1H-pyrazol-3-yl)phenyl)-5-fluoropyrimidin-4-yl)piperidin-4-yl)methanamine hydrochloride (Example 22, step iii, 400 mg, 1.03 mmol) and triethyl amine (300 mg, 3 mmol) in DMF (5 ml) was added HATU (400 mg, 1.03 mmol) and the reaction mixture was stirred at room temperature for 2 hours. The solvent was removed in under reduced pressure and the obtained residue was purified using normal phase chromatography eluting with ethyl acetate to give 2-(3-((1-(2-(3-(1H-pyrazol-3-yl)phenyl)-5-fluoropyrimidin-4-yl)piperidin-4-yl)methylcarbamoyl)-5-methoxyphenoxy)ethyl methanesulfonate (200 mg) as an off white solid.

v) To a solution of the product obtained in the previous step (50 mg, 0.08 mmol) in THF (2 ml) was added dimethyl amine (200 mg, 4.4 mmol) and the reaction mixture was heated to 60° C. for 2 hours. After cooling to room temperature the solvent was removed under reduced pressure and the residue was purified by prep-HPLC to give N-((1-(2-(3-(1H-pyrazol-3-yl)phenyl)-5-fluoropyrimidin-4-yl)piperidin-4-yl)methyl)-3-(2-(dimethylamino)ethoxy)-5-methoxybenzamide (10 mg, 22% yield) as a white solid.

$^1$H NMR (CD$_3$OD): δ 8.58 (s, 1H), 8.27 (d, 1H, J=7.6 Hz), 8.12 (d, 1H, J=7.6 Hz), 7.94 (d, 1H, J=7.2 Hz), 7.70 (d, 1H, J=2.0 Hz), 7.55 (t, 1H, J=7.6 Hz), 7.05 (d, 2H, J=2.0 Hz), 6.74 (d, 2H, J=2.4 Hz), 4.83-4.88 (m, 2H), 4.36 (t, 2H, J=4.8 Hz), 3.82 (s, 3H), 3.58 (t, 2H, J=4.8 Hz), 3.20-3.33 (m, 4H), 2.97 (s, 6H), 2.06-2.07 (m, 1H), 1.94-1.97 (m, 2H), 1.39-1.48 (m, 2H).

Example 25

N-((1-(2-(3-(1H-pyrazol-3-yl)phenyl)-5-fluoropyrimidin-4-yl)piperidin-4-yl)methyl)-3-(cyanomethoxy)-5-methoxybenzamide

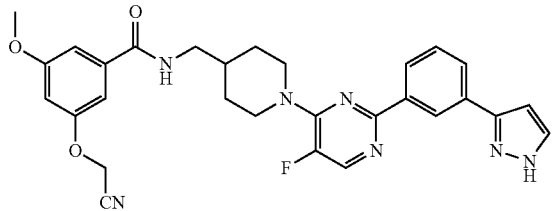 [SMILES: COc1cc(OCC#N)cc(C(=O)NCC2CCN(c3nc(-c4cccc(-c5cc[nH]n5)c4)ncc3F)CC2)c1]

i) Following a procedure analogous to that described in Example 24, step iv using 3-hydroxy-5-methoxybenzoate (34 mg, 0.2 mmol) as the starting material, N-((1-(2-(3-(1H-pyrazol-3-yl)phenyl)-5-fluoropyrimidin-4-yl)piperidin-4-yl)methyl)-3-hydroxy-5-methoxybenzamide (50 mg) was prepared as a white solid.

ii) To a solution of the product obtained in the previous step (50 mg, 0.1 mmol) and bromoacetonitrile (24 mg, 0.2 mmol) in DMF (2 ml) was added at room temperature K$_2$CO$_3$ (70 mg, 0.5 mmol) and the reaction mixture was heated to 100° C. for 2 hours. After cooling to room temperature the mixture was filtered and the filtrate was concentrated under reduced pressure. The residue was purified by prep HPLC to give the title compound N-((1-(2-(3-(1H-pyrazol-3-yl)phenyl)-5-fluoropyrimidin-4-yl)piperidin-4-yl)methyl)-3-(cyanomethoxy)-5-methoxybenzamide (10 mg, 18% yield) as a white solid.

$^1$H NMR (CD$_3$OD): δ 8.48 (s, 1H), 8.22 (d, 1H, J=7.6 Hz), 8.02 (d, 1H, J=7.6 Hz), 7.90 (d, 1H, J=8.0 Hz), 7.63 (d, 1H, J=2.4 Hz), 7.50 (t, 1H, J=8.0 Hz), 7.02 (s, 1H), 6.99 (s, 1H), 6.67-6.70 (m, 2H), 4.92 (s, 2H), 4.78-4.79 (m, 2H), 3.75 (s, 3H), 3.21-3.22 (m, 4H), 1.89-2.06 (m, 3H), 1.31-1.42 (m, 2H).

Example 26

Intermediate Compound

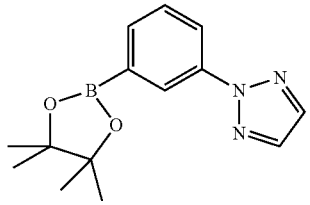 [SMILES: CC1(C)OB(c2cccc(-n3nccn3)c2)OC1(C)C]

i) To solution of 1,3-dibromobenzene (84 g, 356 mmol) in DMF (700 ml) was added 1,2,3-1H-triazole (30 g, 427 mmol), CuI (6.8 g, 35.6 mmol), Iron(III) acetylacetonate (38 g, 107 mmol) and cesium carbonate (231 g, 712 mmol). The resulting mixture was heated to 120° C. under a nitrogen atmosphere overnight. After cooling to room temperature the reaction mixture was filtered and the filtrate was concentrated under reduced pressure. The obtained residue was purified using normal phase chromatography eluting with petroleum ether containing 20% ethyl acetate to give 2-(3-bromophenyl)-2H-1,2,3-triazole (28 g) and 1-(3-bromophenyl)-1H-1,2,3-triazole (11 g) as the pure isomers.

ii) To a solution of 2-(3-bromophenyl)-2H-1,2,3-triazole (Example 11, step 1, 23 g, 103 mmol) in dioxane (330 ml) was added at room temperature bis(pinacolato)diboron (31.5 g, 124 mmol) and potassium acetate (20.2 g, 206 mmol). After purging with nitrogen for 10 minutes, Pd(dppf)Cl$_2$ (3.8 g, 5.2 mmol) was added and the reaction mixture was stirred overnight at 110° C. under a nitrogen atmosphere. After cooling to room temperature the mixture was filtered and the filtrate was concentrated under reduced pressure. The crude product was purified using normal phase chromatography eluting with petroleum ether containing 5% ethyl acetate to give 2-(3-(4,4,5,5-tetramethyl-1,3,2-dioxaborolan-2-yl)phenyl)-2H-1,2,3-triazole (19 g) as a yellow solid.

¹HNMR (CDCl₃): δ 8.50 (d, 1H, J=0.8 Hz), 8.16-8.13 (m, 1H), 7.8 (s, 2H), 7.77 (d, 1H, J=4.0 Hz), 7.48 (t, 1H, J=8.0 Hz), 1.34 (s, 12H).

Example 27

Intermediate Compound

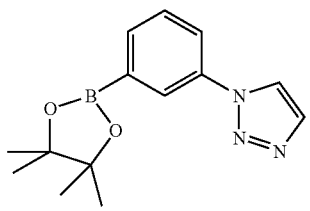 [SMILES: CC1(C)OB(c2cccc(-n3ccnn3)c2)OC1(C)C]

Following a procedure analogous to that described in Example 26, the following compound was prepared.

1-(3-(4,4,5,5-tetramethyl-1,3,2-dioxaborolan-2-yl)phenyl)-1H-1,2,3-triazole

¹HNMR (CDCl₃): δ 8.057 (d, 1H, J=0.6 Hz), 8.039 (d, 1H, J=0.4 Hz), 7.929-7.900 (m, 1H), 7.871-7.832 (m, 2H), 7.532 (t, 1H, J=7.6 Hz), 1.351 (s, 12H).

Example 28

Following a procedure analogous to that described in Example 25, the following compounds were prepared.

28A: N-((1-(2-(3-(2H-1,2,3-triazol-2-yl)phenyl)-5-fluoropyrimidin-4-yl)piperidin-4-yl)methyl)-3-(cyclopropylmethoxy)-5-methoxybenzamide

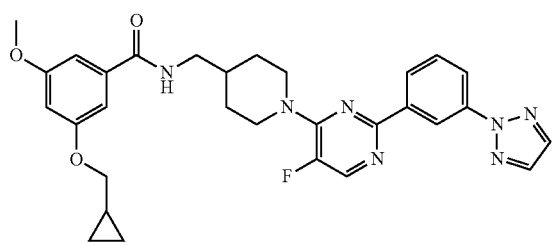 [SMILES: COc1cc(OCC2CC2)cc(C(=O)NCC2CCN(c3nc(-c4cccc(-n5nccn5)c4)ncc3F)CC2)c1]

¹HNMR (CDCl₃): δ 8.91 (s, 1H), 8.49 (d, 1H, J=4.0 Hz), 8.30 (dd, 1H, J₁=8.0 Hz, J₂=8.0 Hz), 8.25 (d, 1H, J=4.0 Hz), 7.85 (s, 2H), 7.671 (t, 1H, J=8.0 Hz), 6.87 (s, 2H), 6.60 (t, 1H, J=2.0 Hz), 6.31 (d, 1H, J=2.8 Hz), 4.94 (d, 2H, J=6.4 Hz), 3.83 (s, 3H), 3.81 (d, 2H, J=2.4 Hz), 3.42 (t, 2H, J=6.4 Hz), 3.27 (t, 2H, J=12.0 Hz), 2.15-2.03 (m, 3H), 1.52-1.46 (m, 2H), 1.28-1.25 (m, 1H), 0.68-0.63 (m, 2H), 0.35-0.34 (m, 2H).

28B: N-((1-(2-(3-(2H-1,2,3-triazol-2-yl)phenyl)-5-fluoropyrimidin-4-yl)piperidin-4-yl)methyl)-3-methoxy-5-(2-methoxyethoxy)benzamide

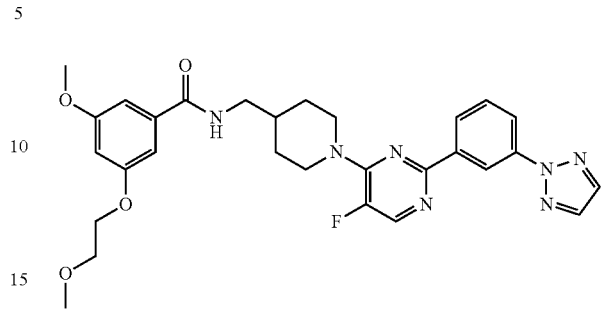

¹HNMR (CDCl₃): δ 8.91 (s, 1H), 8.47 (d, 1H, J=4.0 Hz), 8.28 (t, 2H, J=8.0 Hz), 7.85 (s, 2H), 7.66 (t, 1H, J=8.0 Hz), 6.89 (s, 2H), 6.62 (t, 1H, J=2.4 Hz), 6.33 (t, 1H, J=2.4 Hz), 4.92 (d, 2H, J=6.4 Hz), 4.13 (t, 2H, J=4.8 Hz), 3.8 (s, 3H), 3.74 (t, 2H, J=4.4 Hz), 3.46 (s, 3H), 3.43 (t, 2H, J=6.8 Hz), 3.41-3.39 (m, 2H), 3.24 (t, 2H, J=12.4 Hz), 2.14-2.01 (m, 3H), 1.51-1.42 (m, 2H).

28C: N-((1-(2-(3-(1H-1,2,3-triazol-1-yl)phenyl)-5-fluoropyrimidin-4-yl)piperidin-4-yl)methyl)-3-(cyclopropylmethoxy)-5-methoxybenzamide

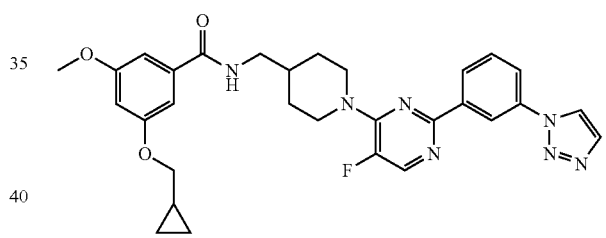

¹HNMR (CD₃OD): δ 8.70 (s, 1H), 8.64 (s, 1H), 8.34-8.31 (m, 2H), 8.05 (t, 1H, J=1.2 Hz), 7.95 (s, 1H), 7.75 (t, 1H, J=8.0 Hz), 6.96 (s, 2H), 6.62 (t, 1H, J=2.0 Hz), 4.85 (d, 2H, J=6.4 Hz), 3.84 (d, 2H, J=3.6 Hz), 3.81 (s, 3H), 3.33-3.31 (m, 2H), 3.31-3.23 (m, 2H), 2.11-1.96 (m, 3H), 1.50-1.40 (m, 2H) 1.29-1.22 (m, 1H), 0.67-0.63 (m, 2H), 0.35-0.33 (m, 2H).

Example 29

N-((1-(4-(3-cyanophenyl)-1,3,5-triazin-2-yl)piperidin-4-yl)methyl)-3-ethoxy-5-methoxybenzamide

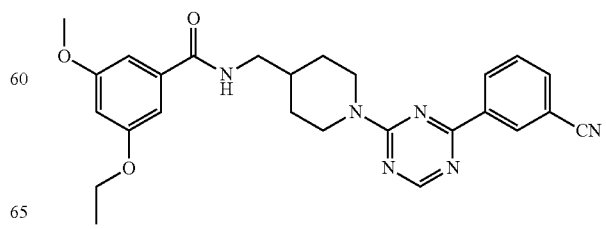

i) A solution of 4-N-Boc-aminomethylpiperidine (25 g, 120 mmol), 2,4-Dichloro-1,3,5-Triazine (20 g, 140 mmol) and DIPEA (77.4 g, 600 mmol) in CH$_3$CN (300 ml) was stirred at room temperature for 2 hours. Water was added and the product was extracted into ethyl acetate. The combined organic layers were washed with brine, dried over Na$_2$SO$_4$ and concentrated under reduced pressure. The crude residue that was purified using normal phase chromatography, eluting with petroleum ether containing 30% ethyl acetate to give tert-butyl (1-(4-chloro-1,3,5-triazin-2-yl)piperidin-4-yl)methylcarbamate as an off white solid (30.0 g).

ii) The product obtained in the previous step (15 g, 45.8 mmol), 3-Cyanophenylboronicacid (8.07 mg, 54.9 mmol), sodium carbonate (9.89 mg, 91.6 mmol) and Pd(PPh$_3$)$_2$Cl$_2$ (1.61 mg, 2.3 mmol) in acetonitrile:water (120 ml, 3:1). After purging with N$_2$ for 15 minutes, the reaction mixture was heated to 150° C. for 1 hour in a microwave reactor. After cooling the solution was poured into water and the product was extracted into ethyl acetate. The combined organic phases were washed with water, brine, dried over Na$_2$SO$_4$ concentrated under reduced pressure giving a dark solid. The crude solid was purified using normal phase chromatography eluting with petroleum ether containing 30% ethyl acetate to give tert-butyl (1-(4-(3-cyanophenyl)-1,3,5-triazin-2-yl)piperidin-4-yl)methylcarbamate as an off white solid (2.2 g).

iii) To a solution of the product obtained in the previous step (2.2 g, 5.58 mmol) in ethyl acetate (20 ml) was added a 6N solution of HCl in ethyl acetate (50 ml). The reaction mixture was stirred at room temperature for 15 minutes and the solvents were removed under reduced pressure to give 3-(4-(4-(aminomethyl)piperidin-1-yl)-1,3,5-triazin-2-yl) benzonitrile hydrochloride as a white solid (1.4 g). The crude product was used in the next step without further purification.

iv) To a solution of the product obtained in the previous step (500 mg, 1.52 mmol), 3-hydroxy-5-methoxybenzoic acid (310 mg, 1.82 mmol), DIPEA (590 mg, 4.56 mmol) in CH$_2$Cl$_2$ (20 ml) was added TBTU (580 mg, 1.82 mmol) and the reaction mixture was stirred for 1 hour at room temperature. After full conversion the solution was poured into water and the product was extracted into ethyl acetate. The combined organic layers were washed with water, brine and dried over Na$_2$SO$_4$. The solvent was removed under reduced pressure and the product was purified using normal phase chromatography eluting with petroleum ether containing 50% ethyl acetate to give the title compound N-((1-(4-(3-cyanophenyl)-1,3,5-triazin-2-yl)piperidin-4-yl)methyl)-3-hydroxy-5-methoxybenzamide as a white solid (481 mg).

v) To a solution of the product obtained in the previous step (40 mg, 0.088 mmol) in DMF (5 ml) were added at room temperature ethyl iodine (20 mg, 0.22 mmol) and K$_2$CO$_3$ (35 mg, 0.27 mmol). The reaction mixture was stirred at 150° C. for 4 hours until full conversion. After cooling to room temperature the solution was concentrated under reduced pressure and the resulting residue was purified using prep HPLC to give the title compound N-((1-(4-(3-cyanophenyl)-1,3,5-triazin-2-yl)piperidin-4-yl)methyl)-3-ethoxy-5-methoxybenzamide (20 mg) as a white solid.

$^1$HNMR (CDCl$_3$): δ 8.78 (s, 1H), 8.63 (s, 1H), 8.58 (d, 1H, J=6.4 Hz), 7.86 (d, 1H, J=7.6 Hz), 7.67 (t, 1H, J=7.2 Hz), 6.86 (s, 2H), 6.59 (s, 1H), 6.35 (s, 1H), 5.08 (d, 1H, J=11.2 Hz), 4.98 (d, 1H, J=0.8 Hz), 4.06 (dd, 2H, J$_1$=J$_2$=6.8 Hz), 3.82 (s, 3H), 3.43 (s, 2H), 3.12-3.04 (m, 2H), 2.10-1.91 (m, 2H), 1.43-1.36 (m, 5H).

Example 30

Following a procedure analogous to that described in Example 29, the following compounds were prepared.

30A: N-((1-(4-(3-cyanophenyl)-1,3,5-triazin-2-yl) piperidin-4-yl)methyl)-3-isobutoxy-5-methoxybenzamide

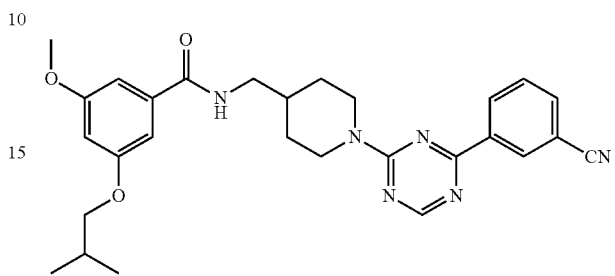

$^1$HNMR (CDCl$_3$): δ 8.71 (s, 1H), 8.69 (s, 1H), 8.64 (d, 1H, J=8.0 Hz), 7.84 (d, 1H, J=7.6 Hz), 7.64 (t, 1H, J=8.0 Hz), 6.86 (d, 2H, J=2.0 Hz), 6.59 (t, 1H, J=2.0 Hz), 6.34-6.23 (m, 1H), 5.08 (d, 1H, J=12.4 Hz), 4.95 (d, 1H, J=14.0 Hz), 3.83 (s, 3H), 3.74 (d, 2H, J=6.8 Hz), 3.45-3.37 (m, 2H), 3.12-2.98 (m, 2H), 2.14-1.93 (m, 4H), 1.40-1.25 (m, 2H), 1.07-1.01 (m, 6H).

30B: 3-sec-butoxy-N-((1-(4-(3-cyanophenyl)-1,3,5-triazin-2-yl)piperidin-4-yl)methyl)-5-methoxybenzamide

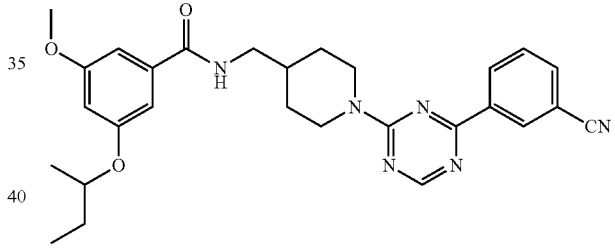

$^1$HNMR (CDCl$_3$): δ 8.77 (s, 1H), 8.62 (s, 1H), 8.56 (d, 1H, J=8.4 Hz), 7.86 (d, 1H, J=7.6 Hz), 7.66 (t, 1H, J=8.0 Hz), 6.83 (d, 2H, J=2.0 Hz), 6.58 (t, 1H, J=2.4 Hz), 6.33 (s, 1H), 5.07 (d, 1H, J=12.8 Hz), 4.95 (d, 1H, J=13.6 Hz), 4.33 (dd, 1H, J$_1$=J$_2$=6.0 Hz), 3.81 (s, 3H), 3.42 (dd, 2H, J$_1$=6.4 Hz, J$_2$=6.0 Hz), 3.08-2.942 (m, 2H), 2.13-1.96 (m, 3H), 1.76-1.60 (m, 2H), 1.58-1.33 (m, 2H), 1.10-0.99 (m, 3H).

30C: N-((1-(4-(3-cyanophenyl)-1,3,5-triazin-2-yl) piperidin-4-yl)methyl)-3-methoxy-5-(2,2,2-trifluoroethoxy)benzamide

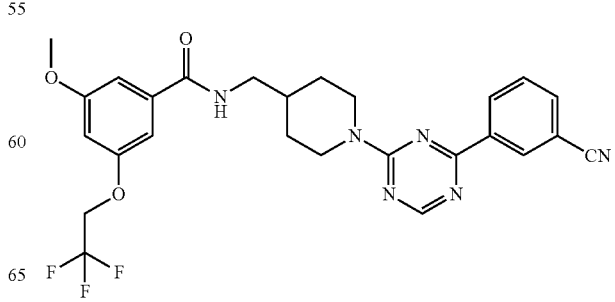

¹HNMR (CDCl₃): δ 8.78 (s, 1H), 8.64 (s, 1H), 8.60 (d, 1H, J=8.0 Hz), 7.89 (d, 1H, J=7.6 Hz), 7.49 (s, 1H), 7.69 (t, 1H, J=8.0 Hz), 6.97 (s, 1H), 6.94 (s, 1H), 6.66 (s, 1H), 3.36 (s, 1H), 5.16 (d, 1H, J=8.8 Hz), 5.03-4.91 (m, 1H), 4.43-4.33 (m, 2H), 3.86 (s, 3H), 3.46-3.42 (m, 2H), 3.15-3.04 (m, 2H), 2.21-1.91 (m, 3H) 1.43-1.37 (m, 2H).

30D: N-((1-(4-(3-cyanophenyl)-1,3,5-triazin-2-yl)piperidin-4-yl)methyl)-3-methoxy-5-(2,2,2-trifluoroethoxy)benzamide

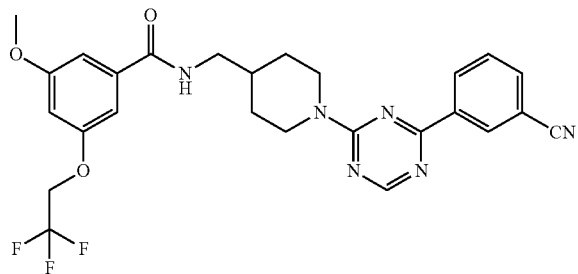 [SMILES: COc1cc(OCC(F)(F)F)cc(C(=O)NCC2CCN(c3ncnc(-c4cccc(C#N)c4)n3)CC2)c1]

MS (ESI) me: 499.59 (M+H)+.

Example 31

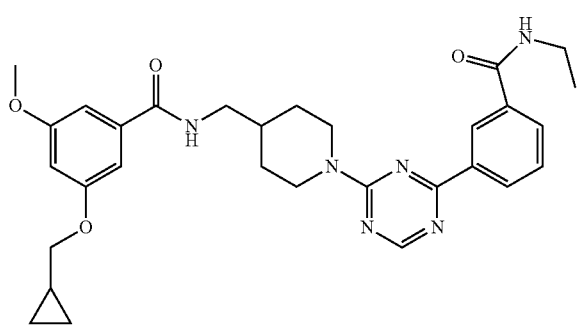 [SMILES: CCNC(=O)c1cccc(-c2ncnc(N3CCC(CNC(=O)c4cc(OC)cc(OCC5CC5)c4)CC3)n2)c1]

3-(cyclopropylmethoxy)-N-((1-(2-(3-(ethylcarbamoyl)phenyl)pyrimidin-4-yl)piperidin-4-yl)methyl)-5-methoxybenzamide i) A suspension of methyl 3,5-dihydroxybenzoate (89 mmol, 15 g), potassium carbonate (107 mmol, 14.79 g) and iodomethane (89 mmol, 5.55 ml, 12.66 g) in acetone (300 ml) was stirred at 60° C. for 4 hours. TLC showed a mixture of 3 compounds which were starting material, mono methylated product and demethylated product. After cooling to room temperature, acetone was removed under reduced pressure and the oily residue was partitioned between ethyl acetate and water. The organic layer was washed with brine, dried over Na₂SO₄, filtered and evaporated under reduced pressure. The crude product was purified using normal phase chromatography was purified using normal phase chromatography eluting with ethyl acetate and increasing amounts of heptane to give methyl 3-hydroxy-5-methoxybenzoate (6.25 g) as a clear oil.

ii) A slurry of the compound obtained in the previous step (2.55 g, 14.0 mmol), (bromomethyl)cyclopropane (1.643 ml, 16.80 mmol) and cesium carbonate (5.47 g, 16.8 mmol) in DMF (2 ml) was stirred at 50° C. overnight. After cooling to room temperature, the mixture was partitioned between ethyl acetate and water. The combined organic layers were washed with brine, dried over Na₂SO₄ and concentrated under reduced pressure.

The obtained residue was dissolved in ethanol (10 ml) and a 2N aqueous solution of sodium hydroxide (5 ml) was added. The reaction mixture was stirred at 50° C. for 1.5 hours. After cooling to room temperature water was added and the pH was adjusted to pH=1 by addition of a 1N aqueous solution of HCl. The formed crystals were removed by filtration, washed with water and dried to give 3-(cyclopropylmethoxy)-5-methoxybenzoic acid (2.97 g).

iii) A suspension of the product obtained in the previous step (2.99 g, 13.44 mmol), tert-butyl 4-(aminomethyl)piperidine-1-carboxylate (2.4 g, 11.20 mmol) and DIPEA (5.55 ml, 33.6 mmol) in CH₂Cl₂ (5 ml) was stirred for 15 minutes before HATU (13.44 mmol, 5.11 g) was added. After the reaction mixture was stirred at room temperature for 2 hours, a saturated aqueous solution of NaHCO3 was added and the product was extracted into CH₂Cl₂CH₃OH (91). The organic layer was dried over Na₂SO₄ and concentrated under reduced pressure. The crude product was purified using normal phase chromatography eluting with ethyl acetate and increasing amounts of heptane to give tert-butyl 4-((3-(cyclopropylmethoxy)-5-methoxybenzamido)methyl)piperidine-1-carboxylate (6.5 g).

iv) To a solution of the product obtained in the previous step (5.12 g, 12.23 mmol) in CH₂Cl₂ (75 ml) was added at room temperature trifluoroacetic acid (10.90 ml, 147 mmol). After stirring for 2 hours at room temperature the reaction mixture was concentrated under reduced pressure. The obtained residue was dissolved CH₂Cl₂ and silica bound CARBONATE (147 mmol) was added and stirred for 15 min. The mixture was filtered and the filtrate concentrated to afford 3-(cyclopropylmethoxy)-5-methoxy-N-(piperidin-4-ylmethyl)benzamide 2,2,2-trifluoroacetate (5.23 g) as a white solid.

v) To a solution of the product obtained in the previous step (1 g, 2.31 mmol) in ethanol (25 ml) were added at -78° C. DIPEA (0.764 ml, 4.62 mmol) and 2,4-dichloropyrimidine (0.45 g, 3.01 mmol). The reaction mixture was stirred at -78° C. and was allowed to warm to rt. The reaction mixture was concentrated under reduced pressure and the obtained residue was dissolved in CH₂Cl₂. The organic layer was washed with water, dried over Na₂SO₄ and concentrated under reduced pressure. The crude product was purified using normal phase chromatography eluting with ethyl acetate and increasing amounts of heptane to give N-((1-(2-chloropyrimidin-4-yl)piperidin-4-yl)methyl)-3-(cyclopropylmethoxy)-5-methoxybenzamide (480 mg) as an of white solid.

vi) To a solution of the product obtained in the previous step (480 mg, 1.12 mmol) in dioxane (3 ml) were added 3-(methoxycarbonyl)phenylboronic acid (300 mg, 1.66 mmol) and potassium carbonate (460 mg, 3. mmol). After purging with nitrogen for 15 minutes, tetrakis(triphenylphosphine)palladium(0) (128 mg, 0.11 mmol) was added and the reaction mixture was heated to 150° C. for 20 minutes in a microwave reactor. After cooling to room temperature the reaction mixture was diluted with CH₂Cl₂ and the organic layer was washed with brine and dried over Na₂SO₄. The solvents were removed under reduced pressure and the obtained residue was purified using normal phase chromatography eluting with ethyl acetate and increasing amounts of heptane to give methyl 3-(4-(4-((3-(cyclopropylmethoxy)-5-methoxybenzamido)methyl)piperidin-1-yl)pyrimidin-2-yl)benzoate (400 mg) as a white solid. vii) To a solution of the product obtained in the previous step (278 mg, 0.523 mmol) in methanol (2 ml) was added dropwise a 1N aqueous solution of NaOH (1 ml). After stirring for 2 hours at room temperature the reaction mixture was acidified by the addition of a 2N aqueous solution of HCl. The product was extracted into CH$_2$Cl$_2$ and the organic layer was washed with brine, dried over Na$_2$SO$_4$ and concentrated under reduced pressure to give 3-(4-(4-((3-(cyclopropylmethoxy)-5-methoxybenzamido) methyl)piperidin-1-yl)pyrimidin-2-yl)benzoic acid (214 mg) as a clear oil. The crude product was used in the next step without further purification.

viii) The product obtained in the previous step (40.0 mg, 0.077 mmol), ethanamine (10.5 mg, 0.232 mmol), DIPEA (29.8 mg, 0.231 mmol) were suspended in CH$_2$Cl$_2$ (5 ml). After stirring for 15 minutes at room temperature, HATU (32.3 mg, 0.085 mmol) was added and the reaction mixture was stirred for 2 hours at room temperature. A saturated aqueous solution of NaHCO$_3$ was added and the aqueous layer was extracted with CH$_2$Cl$_2$CH$_3$OH 91. The organic layer was dried over Na$_2$SO$_4$ and concentrated under reduced pressure. The obtained residue was purified using normal phase chromatography eluting with ethyl acetate and increasing amounts of heptane to give the title compound 3-(cyclopropylmethoxy)-N-((1-(2-(3-(ethylcarbamoyl)phenyl)pyrimidin-4-yl)piperidin-4-yl)methyl)-5-methoxybenzamide (23 mg) as a white solid. $^1$H NMR (CDC$_{13}$): δ 8.63 (s, 1H), 8.48 (t, 1H), 8.23 (m, 1H), 7.54 (m, 1H), 6.88 (m, 2H), 6.59 (t, 1H), 6.30 (m, NH), 6.20 (m, NH), 5.05-4.90 (dd, 2H), 3.82 (s, 3H), 3.82 (d, 2H), 3.40 (m, 2H), 3.07 (d, 3H), 2.98 (m, 2H), 2.02 (t, 1H), 1.92 (m, 2H), 1.27 (m, 4H), 0.88 (t, 1H), 0.66 (m, 2H), 0.35 (m, 2H).

Following a procedure analogous to that described in Example 31, the following compounds were prepared.

Example 32

32A: 3-(cyclopropylmethoxy)-N-((1-(2-(3-(ethylcarbamoyl)phenyl)pyrimidin-4-yl)piperidin-4-yl)methyl)-5-methoxybenzamide

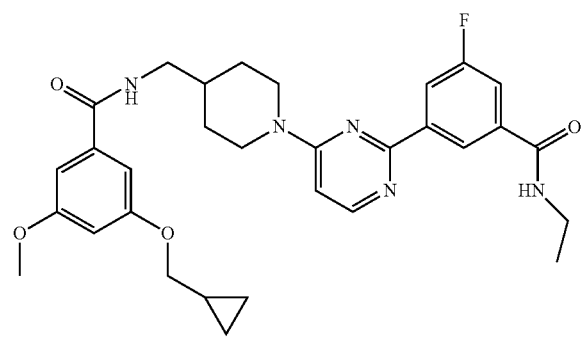 [SMILES: CCNC(=O)c1cc(F)cc(-c2nccc(N3CCC(CNC(=O)c4cc(OC)cc(OCC5CC5)c4)CC3)n2)c1]

$^1$HNMR (CDCl$_3$ DMSO d$^6$): δ 8.78 (s, 1H), 7.76 (m, 1H), 8.48 (m, 1H), 8.43 (m, 1H), 8.30 (d, 1H), 7.92 (m, 1H), 7.57 (t, 1H), 7.00 (m, 2H), 6.81 (t, 1H), 6.63 (t, 1H), 4.58 (m, 2H), 4.45 (q, 2H), 3.74 (d, 2H), 3.75 (s, 3H), 3.17 (t, 2H), 2.99 (t, 2H), 2.23 (m, 2H), 2.10 (m, 2H), 1.94 (m, 1H), 1.70 (m, 2H), 1.68 (m, 2H), 1.18 (m, 3H), 0.59 (m, 2H), 0.33 (m, 2H).

32B: N-((1-(4-(3-carbamoylphenyl)-1,3,5-triazin-2-yl)piperidin-4-yl)methyl)-3-(cyclopropylmethoxy)-5-methoxybenzamide

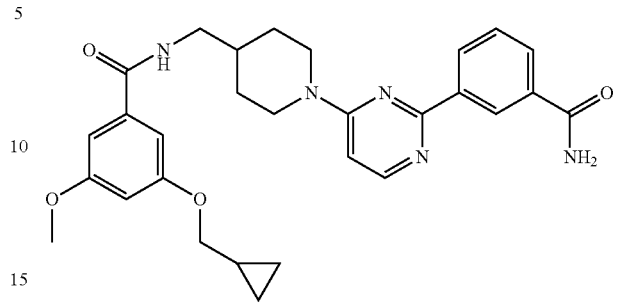

$^1$H NMR (CDCl$_3$): δ 8.78 (t, 1H), 8.63 (s, 1H), 8.58 (d, 1H), 8.05 (d, 1H), 7.58 (t, 1H), 6.88 (m, 2H), 6.59 (t, 1H), 6.2 (t, NH), 5.10 (d, 1H), 4.91 (d, 1H), 3.82 (s, 3H) 3.82 (d, 2H), 3.40 (m, 2H), 2.98 (m, 2H), 1.92 (m, 2H), 1.30 (m, 1H), 1.27 (m, 2H), 0.65 (m, 2H), 0.25 (m, 2H).

32C: 3-(cyclopropylmethoxy)-5-methoxy-N-((1-(2-(3-(1-methyl-1H-pyrazol-3-ylcarbamoyl)phenyl)pyrimidin-4-yl)piperidin-4-yl)methyl)benzamide

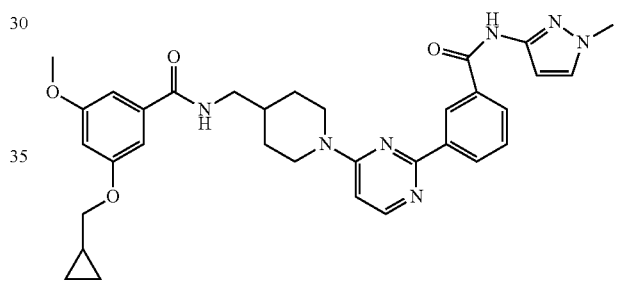

$^1$H NMR (DMSO d$^6$): δ 10.95 (s, 1H), 8.87 (t, 1H), 8.49 (m, 2H), 8.31 (d, 1H) 8.08 (m, 1H), 7.62 (d, 1H), 7.58 (t, 1H), 6.99 (m, 2H), 6.82 (d, 1H), 6.63 (m, 2H), 3.83 d (2H), 3.79 (s, 3H), 3.77 (s, 3H), 3.18 (m, 2H), 2.98 (m, 2H), 1.97 (m, 1H), 1.81 (m, 2H), 1.21 (m, 3H) 0.60 (m, 2H), 0.44 (m, 2H)

32D: 3-(cyclopropylmethoxy)-5-methoxy-N-((1-(4-(3-(pyrrolidine-1-carbonyl)phenyl)-1,3,5-triazin-2-yl)piperidin-4-yl)methyl)benzamide

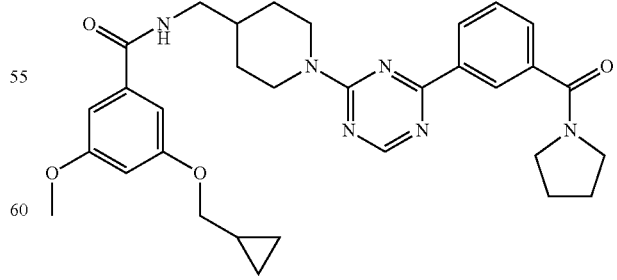

$^1$H NMR (DMSO): δ 8.62 (s, 1H), 8.56 (t, 1H), 8.46 (m, 1H), 7.68 (m, 1H), 7.52 (t, 1H), 6.89 (m, 2H), 6.60 (t, 1H), 6.20 (t, NH), 5.08 (m, 1H), 4.90 (m, 1H), 3.82 (d, 2H), 3.82 (s,

3H), 3.68 (t, 2H), 3.46 (t, 2H), 3.39 (m, 2H), 2.95 (m, 2H), 1.98 (m, 3H), 1.90 (m, 4H), 1.28 (m, 2H), 0.98 (t, 1H), 0.66 (m, 2H), 0.36 (m, 2H)

32E: methyl 2-(3-(4-(4-((3-(cyclopropylmethoxy)-5-methoxybenzamido)methyl)piperidin-1-yl)-1,3,5-triazin-2-yl)benzamido)acetate

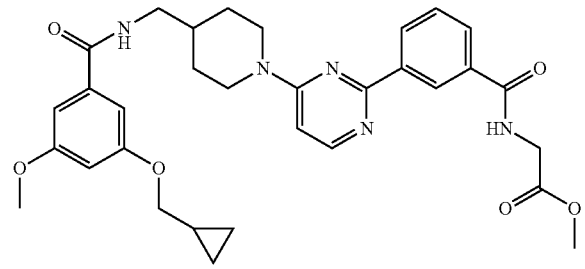 [SMILES: COC(=O)CNC(=O)c1cccc(-c2nccc(N3CCC(CNC(=O)c4cc(OC)cc(OCC5CC5)c4)CC3)n2)c1]

MS (ESI) me: 588.9 (M+H)+.

32F: N-((1-(2-(3-(tert-butylcarbamoyl)phenyl)pyrimidin-4-yl)piperidin-4-yl)methyl)-3-(cyclopropylmethoxy)-5-methoxybenzamide

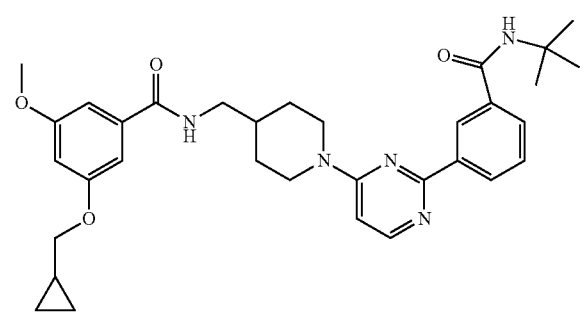 [SMILES: COc1cc(OCC2CC2)cc(C(=O)NCC2CCN(c3ccnc(-c4cccc(C(=O)NC(C)(C)C)c4)n3)CC2)c1]

MS (ESI) me: 572.721 (M+H)+.

32G: 3-(cyclopropylmethoxy)-N-((1-(4-(3-(2,2-difluoroethylcarbamoyl)phenyl)-1,3,5-triazin-2-yl)piperidin-4-yl)methyl)-5-methoxybenzamide

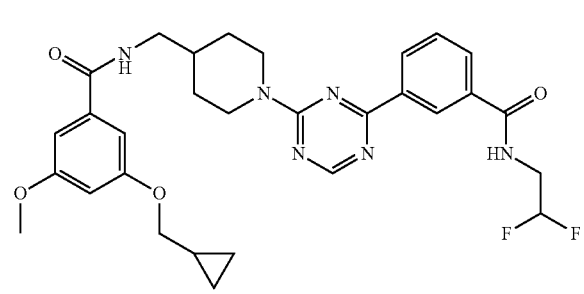 [SMILES: COc1cc(OCC2CC2)cc(C(=O)NCC2CCN(c3ncnc(-c4cccc(C(=O)NCC(F)F)c4)n3)CC2)c1]

MS (ESI) me: 581.64 (M+H)+.

32H: 3-(cyclopropylmethoxy)-N-((1-(4-(3-(2-hydroxyethylcarbamoyl)phenyl)-1,3,5-triazin-2-yl)piperidin-4-yl)methyl)-5-methoxybenzamide

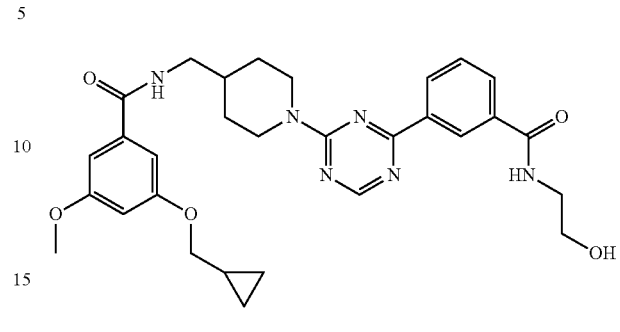

MS (ESI) me: 561.65 (M+H)+.

32I: 3-(cyclopropylmethoxy)-5-methoxy-N-((1-(4-(3-(thiazol-2-ylcarbamoyl)phenyl)-1,3,5-triazin-2-yl)piperidin-4-yl)methyl)benzamide

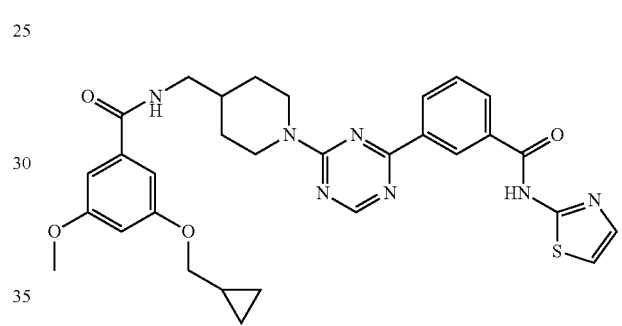

MS (ESI) me: 600.71 (M+H)+.

Example 33

Following a procedure analogous to that described in Example 31, step vi, using the appropriate phenylboronic acid, the following compounds were prepared.

33A: 3-(cyclopropylmethoxy)-5-methoxy-N-((1-(2-(3-(4-methyl-1H-pyrazol-1-yl)phenyl)pyrimidin-4-yl)piperidin-4-yl)methyl)benzamide

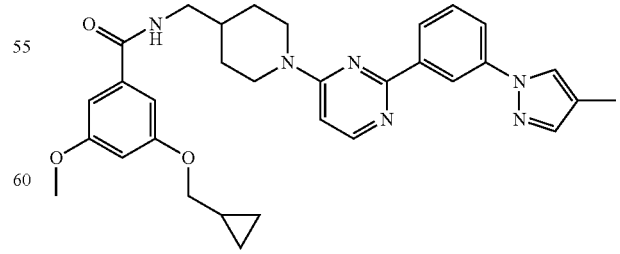

$^1$H NMR DMSO d$^6$): δ 8.50 (t, 1H), 8.48 (m, 1H), 8.32 (m, 2H), 8.22 (m, 1H), 7.86 (m, 1H), 7.60 (s, 1H), 7.57 (t, 1H), 7.0 (m, 2H), 6.83 (d, 1H), 6.64 (t, 1H), 4.55 (m, 2H), 3.85, (d, 2H, 3.77 (s, 3H), 3.20 (t, 2H), 2.97 (t, 2H), 2.12 (s, 3H), 1.93 (m, 1H), 1.80 (m, 2H), 1.20 (m, 3H), 0.57 (m, 2H), 0.33 (m, 2H).

33B: N-((1-(2-(benzo[d]isoxazol-5-yl)pyrimidin-4-yl)piperidin-4-yl)methyl)-3-(cyclopropylmethoxy)-5-methoxybenzamide

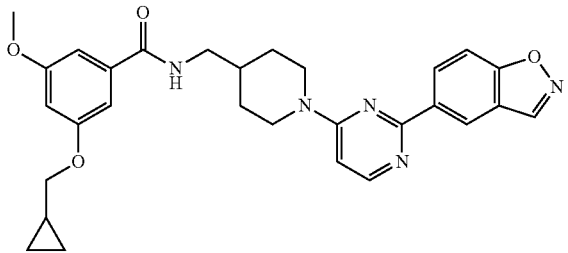 [SMILES: COc1cc(OCC2CC2)cc(C(=O)NCC2CCN(c3ccnc(-c4ccc5oncc5c4)n3)CC2)c1]

$^1$H NMR (DMSO d$^6$): δ 8.48 (m, 2H), 8.42 (m, 2H), 8.24 (d, 1H), 7.07 (m, 1H), 6.97 (m, 2H) 6.54 d (1H), 6.63 (t, 1H), 4.53 (m, 2H), 3.84 (d, 2H), 3.77 (s, 3H), 3.16 (m, 2H), 2.94 (m, 2H), 1.90 (m, 1H), 1.77 (m, 2H), 1.18 (m, 3H), 0.59 (m, 2H), 0.33 (m, 2H)

33C: N-((1-(2-(3-cyano-4-fluorophenyl)pyrimidin-4-yl)piperidin-4-yl)methyl)-3-(cyclopropylmethoxy)-5-methoxybenzamide

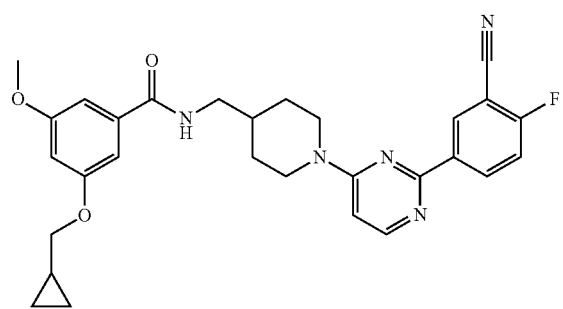 [SMILES: COc1cc(OCC2CC2)cc(C(=O)NCC2CCN(c3ccnc(-c4ccc(F)c(C#N)c4)n3)CC2)c1]

$^1$H NMR (DMSO d$^6$): δ 8.68 (m, 2H), 8.47 (t, 1H), 8.28 (d, 1H), 7.63 (t, 1H), 6.98 (m, 2H), 6.84 (d, 1H), 6.62 (t, 1H), 3.84 (d, 2H), 3.78 (s, 3H), 3.17 (m, 2H), 2.96 (m, 2H), 1.92 (m, 1H), 1.77 (m, 2H), 1.18 (m, 3H), 0.56 (m, 2H), 0.37 (m, 2H)

33D: 1-(3-(4-(4-((3-(cyclopropylmethoxy)-5-methoxybenzamido)methyl)piperidin-1-yl)pyrimidin-2-yl)phenyl)-5-methyl-1H-pyrazole-4-carboxylic acid

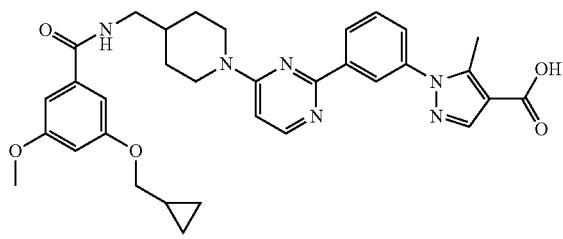 [SMILES: COc1cc(OCC2CC2)cc(C(=O)NCC2CCN(c3ccnc(-c4cccc(-n5ncc(C(=O)O)c5C)c4)n3)CC2)c1]

$^1$H NMR (CDCl$_3$): δ 12.31 (bs, 1H), 8.56 (d, 1H), 8.47 (m, 1H), 8.36 (m, 1H), 8.10 (s, 1H), 7.68 (m, 2H), 6.89 (m, 2H), 6.62 (d, 1H), 6.59 (t, 1H), 4.79 (m, 2H), 3.82 (d, 2H), 3.81 (s, 3H), 3.40 (t, 2H), 3.12 (m, 2H), 2.63 (s, 3H), 2.10 (m, 1H), 2.00 (d, 2H), 1.32 (m, 3H), 0.66 (m, 2H), 0.36 (m, 2H)

33E: N-((1-(2-(6-(1H-pyrazol-1-yl)pyridin-2-yl)pyrimidin-4-yl)piperidin-4-yl)methyl)-3-(cyclopropylmethoxy)-5-methoxybenzamide

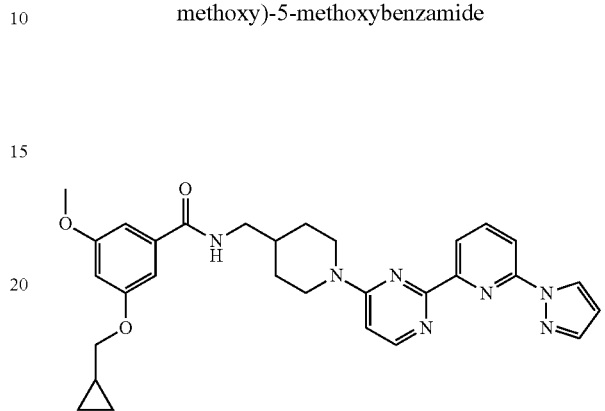

$^1$H NMR (DMSO d$^6$): δ 9.27 (d, 1H), 8.52 (t, 1H), 8.44, (m, 2H) 8.26 (m, 2H), 7.93 (m, 1H), 7.26 (d, 1H) 6.99 (m, 2H), 6.72 (m, 1H), 6.63 (t, 1H), 4.20 (m, 1H), 3.84 (d, 2H), 3.78 (s, 3H), 3.43 (m, 4H), 3.22 (m, 2H), 2.03 (m, 1H), 1.89 (m, 2H), 1.25 (m, 3H), 0.58 (m, 2H), 0.34 (m, 2H)

Example 34

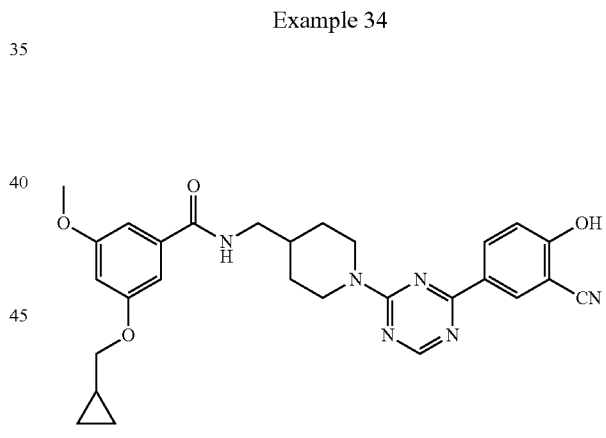

N-((1-(4-(3-cyano-4-hydroxyphenyl)-1,3,5-triazin-2-yl)piperidin-4-yl)methyl)-3-(cyclopropylmethoxy)-5-methoxybenzamide Following a procedure analogous to that described in Example 31, step vi, using benzo[d]isoxazol-5-ylboronic acid, the following compound was prepared. After purification by using HPLC in the presence of trifluoroacetic acid, N-((1-(4-(benzo[d]isoxazol-5-yl)-1,3,5-triazin-2-yl)piperidin-4-yl)methyl)-3-(cyclopropylmethoxy)-5-methoxybenzamide rearranged to N-((1-(4-(3-cyano-4-hydroxyphenyl)-1,3,5-triazin-2-yl)piperidin-4-yl)methyl)-3-(cyclopropylmethoxy)-5-methoxybenzamide MS (ESI) me: 415.6 (M+H)+.

Example 35

N-(6-(2-(3-(1H-pyrazol-1-yl)phenyl)pyrimidin-4-yl)-6-azaspiro[2.5]octan-1-yl)-3-(cyclopropylmethoxy)-5-methoxybenzamide

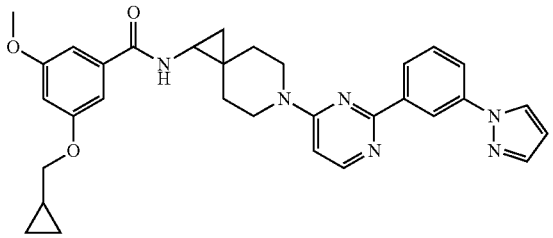 [SMILES: COc1cc(OCC2CC2)cc(C(=O)NC2CC23CCN(c2ccnc(-c4cccc(-n5cccn5)c4)n2)CC3)c1]

i) To solution of compound benzyl 4-oxopiperidine-1-carboxylate (3 g, 0.013 mol) in toluene (50 ml) was added $PPh_3CH_2COOCH_3$ (5.37 g, 16.1 mmol) and the reaction mixture was heated to reflux overnight. After cooling to room temperature, the reaction mixture was concentrated under reduced pressure and the obtained residue was purified using normal phase chromatography to give benzyl 4-(2-methoxy-2-oxoethylidene)piperidine-1-carboxylate (3.8 g) as a yellow oil.

ii) To a solution of $(Me)_3SOI$ (3.39 g, 15.4 mmol) in DMSO (20 ml) was added t-ButOK (1.73 g, 15.4 mmol) in portions and the reaction mixture was stirred at room temperature for 3 h. Then a solution of the product obtained in the previous step (2.5 g, 8.6 mmol) in DMSO (5 ml) was added drop wise and the reaction mixture was stirred at room temperature overnight. After full conversion brine (200 ml) was added and the product was extracted into ethyl acetate. The combined organic phases were washed with brine, dried over $Na_2SO_4$ and concentrate under reduced pressure. The obtained residue was purified by using normal phase chromatography to give compound 6-benzyl 1-methyl 6-azaspiro[2.5]octane-1,6-dicarboxylate (1.7 g) as a colorless oil.

iii) To a solution of the product obtained in the previous step (1.7 g, 5.6 mmol) in THF $H_2O$ (20 ml, 11) was added lithium hydroxide (1.18 g, 28 mmol) and the reaction mixture was stirred at room temperature. After full conversion, the reaction mixture was concentrated under reduced pressure. The residue was treated with $H_2O$ (20 ml) and extracted with ethyl acetate. The aqueous layer was acidified to pH=3 and extracted with ethyl acetate. The combined organic layers were washed with brine, dried over $Na_2SO_4$ and concentrated under reduced pressure to give 6-(benzoxycarbonyl)-6-azaspiro[2.5]octane-1-carboxylic acid (1.5 g) as a colorless oil. The crude product was used in the next step without further purification.

iv) To a solution of the product obtained in the previous step (19 g, 65.5 mmol) in toluene (200 ml) was added DPPA (27 g, 98.2 mmol) and TEA (19.8 g, 196.5 mmol). The reaction mixture was stirred at reflux temperature for 6 h. After cooling to room temperature t-BuOH (14.3 g, 196.5 mmol) was added and the reaction mixture was stirred at reflux temperature overnight. After cooling to room temperature, the reaction mixture was concentrated under reduced pressure and the obtained residue was purified by using normal phase chromatography to give benzyl 1-(tert-butoxycarbonylamino)-6-azaspiro[2.5]octane-6-carboxylate (15 g) as a colorless oil.

v) To a solution of the product obtained in the previous step (8 g, 22 mmol) in $CH_2Cl_2$ (10 ml) was added drop wise an 4N solution of HCl in ethyl acetate (22 ml). After stirring for 1 hour at room temperature, the reaction mixture was concentrated under reduced pressure to give benzyl 1-amino-6-azaspiro[2.5]octane-6-carboxylate hydrochloride (5.7 g, 87%) as a white solid.

vi) To a solution of 3-Cyclopropylmethoxy-5-methoxybenzoic acid (3 g, 13.5 mmol) in $CH_2Cl_2$ (30 ml) were added TEA (4.09 g, 40.5 mmol) and TBTU (4.59 g, 14.1 mmol). After stirring for 5 minutes, the product obtained in the previous step (4.4 g, 14.9 mmol) was added and the reaction mixture was stirred at room temperature 2 hours. The reaction mixture was concentrated under reduced pressure and the residue was purified by using normal phase chromatography to give benzyl 1-(3-(cyclopropylmethoxy)-5-methoxybenzamido)-6-azaspiro[2.5]octane-6-carboxylate as a mixture of both enantiomers. Separation by SFC gave the 2 enantiomers (2.2 g and 2.1 g) as colorless oils.

vii) To a solution the product obtained in the previous step (1 g, 2 mmol) in ethanol (30 ml) was added 10% PdC (0.3 g) under a nitrogen atmosphere. After stirring for 5 minutes, the reaction mixture was stirred under a hydrogen atmosphere overnight. The reaction mixture was filtered through celite and the residue was washed with ethyl acetate. The filtrate was concentrated under reduced pressure to give 3-(cyclopropylmethoxy)-5-methoxy-N-(6-azaspiro[2.5]octan-1-yl)benzamide (0.65 g) as a colorless oil. The crude product was used in the next step without further purification.

viii) To a solution the product obtained in the previous step (100 mg, 0.30 mmol) in $CH_3CN$ were added TEA (91 mg, 0.909 mmol) and 2,4-dichloro-pyrimidine (68 mg, 0.454 mmol). The reaction mixture was stirred at room temperature for 2 hours. The reaction mixture was concentrated under reduced pressure and the obtained residue was purified by using normal phase chromatography to give (R)—N-(6-(2-chloropyrimidin-4-yl)-6-azaspiro[2.5]octan-1-yl)-3-(cyclopropylmethoxy)-5-methoxybenzamide (125 mg) as a white solid.

ix) Analogous to a procedure described in Example 11, step ii, the title compound N-(6-(2-(3-(1H-pyrazol-1-yl)phenyl)pyrimidin-4-yl)-6-azaspiro[2.5]octan-1-yl)-3-(cyclopropylmethoxy)-5-methoxybenzamide was prepared.

$^1$H NMR (CDCl$_3$): δ 8.61 (d, 1H, J=8.0 Hz), 8.54 (s, H), 8.45 (d, 1H, J=6.4 Hz), 7.90 (d, 1H, J=7.2 Hz), 7.66 (d, 1H, J=8.8 Hz), 7.31 (d, 1H, J=15.2 Hz), 6.82-6.89 (m, 2H), 6.73 (s, 1H), 6.53-6.61 (m, 2H), 4.60-4.90 (m, 1H), 3.94-4.07 (m, 1H), 3.65-3.83 (m, 7H), 2.81-2.90 (m, 1H), 1.80-1.92 (m, 2H), 1.53-1.62 (m, 1H), 1.42-1.51 (m, 1H), 1.18-1.30 (m, 1H), 1.01-1.09 (m, 1H), 0.56-0.72 (m, 1H), 0.50-0.56 (m, 2H), 0.31-0.42 (m, 2H).

Example 36

N-(1-(1-(4-(3-cyanophenyl)-1,3,5-triazin-2-yl)piperidin-4-yl)ethyl)-3-(cyclopropylmethoxy)-5-methoxybenzamide

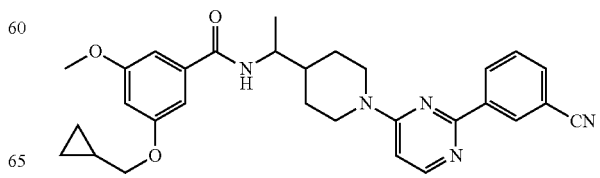

i) To a solution of 3-(2-cyclopropylethyl)-5-methoxybenzoic acid (2.4 g, 10.7 mmol) and tert-butyl 4-(1-aminoethyl)piperidine-1-carboxylate (2.4 g, 10.7 mmol) in DMF (40 ml), was added triethyl amine (4.47 ml). After stirring for 10 minutes at room temperature TBTU (5.15 g, 16.1 mmol) was added in portions. The reaction mixture was stirred at room temperature for 2 hours. 100 ml H$_2$O was added and the product was extracted into ethyla acetate. The combined organic layers were washed with brine, dried over Na$_2$SO$_4$ and concentrated under reduced pressure. The obtained residue was purified by using normal phase chromatography eluting with petroleum ether containing 10% ethyl acetate to give tert-butyl 4-(1-(3-(cyclopropylmethoxy)-5-methoxybenzamido)ethyl)piperidine-1-carboxylate (3.0 g).

ii) To a stirred solution of the product obtained in the previous step (900 mg, 2.1 mmol) in CH$_2$Cl$_2$ (12 ml), was added TFA (3 ml). The reaction mixture was stirred at room temperature for 30 minutes and after completion, the reaction mixture was concentrated under reduced pressure to afford 3-(cyclopropylmethoxy)-5-methoxy-N-(1-(piperidin-4-yl)ethyl)benzamide 2,2,2-trifluoroacetate (900 mg). The crude product was used in the next step without further purification.

iii) A solution of the product obtained in the previous step (900 mg) and diethyl amine in CH$_3$CN (40 ml) was stirred for 10 minutes at room temperature. 2,4-dichloro-1,3,5-triazine (733 mg, 4.89 mmol) was added and the reaction mixture was stirred for 1 hour at room temperature. 100 ml H$_2$O was added and a white solid precipitated which was filtered off and dried under reduced pressure to give N-(1-(1-(4-chloro-1,3,5-triazin-2-yl)piperidin-4-yl)ethyl)-3-(cyclopropylmethoxy)-5-methoxybenzamide (980 mg).

iv) To a solution of the product obtained in the previous step (150 mg, 0.34 mmol) in CH$_3$CN H$_2$O (4 ml, 31), were added 3-cyanophenylboronicacid (60 mg, 0.41 mmol), Na$_2$CO$_3$ (73 mg, 0.68 mmol) and Pd (PPh$_3$)$_2$Cl$_2$ (12 mg, 0.017 mmol) under a nitrogen atmosphere. The reaction mixture was heated to 150° C. for 10 minutes in a microwave reactor. The mixture was filtered and the filtrate was dried over Na$_2$SO$_4$ and concentrated under reduced pressure. The residue was purified by using preparative-HPLC to give the title compound N-(1-(1-(4-(3-cyanophenyl)-1,3,5-triazin-2-yl)piperidin-4-yl)ethyl)-3-(cyclopropylmethoxy)-5-methoxybenzamide (25 mg).

$^1$H NMR (CD$_3$OD): δ 8.331-8.277 (m, 3H), 7.584 (d, 1H, J=3.8 Hz), 7.355 (t, 1H, J=3.2 Hz), 6.606 (t, 2H, J=2.0 Hz), 6.277 (t, 1H, J=2.4 Hz), 4.782-4.757 (m, 1H), 3.663 (t, 1H, J=6.8 Hz), 3.525 (d, 2H, J=13.2 Hz), 3.467 (s, 3H), 2.679 (t, 2H, J=12.4 Hz), 1.653-1.574 (m, 2H), 1.547-1.520 (m, 1H), 1.009-0.944 (m, 2H), 0.914 (d, 3H, J=3.2 Hz), 0.270 (d, 2H, J=3.6 Hz), 0.005 (d, 2H, J=1.8 Hz).

Example 37

Following a procedure analogous to that described in Example 36, the following compound was prepared.

N-(1-(1-(4-(3-(1H-pyrazol-3-yl)phenyl)-1,3,5-triazin-2-yl)piperidin-4-yl)ethyl)-3-(cyclopropylmethoxy)-5-methoxybenzamide

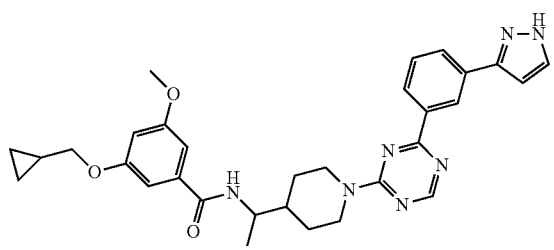 [SMILES: COc1cc(OCC2CC2)cc(C(=O)NC(C)C2CCN(c3ncnc(-c4cccc(-c5cc[nH]n5)c4)n3)CC2)c1]

$^1$H NMR (CD$_3$OD): δ 8.88 (s, 1H), 8.58 (d, 1H, J=8.0 Hz), 8.21 (d, 1H, J=8.4 Hz), 7.98 (d, 1H, J=7.6 Hz), 7.69 (s, 1H), 7.60 (t, 1H, J=8.0 Hz), 6.85 (t, 3H, J=6.8 Hz), 6.61 (t, 2H, J=7.6 Hz), 5.91 (dd, 1H, J$_1$=2.4 Hz, J$_2$=2.0 Hz), 4.22 (dd, 1H, J$_1$=8.8 Hz, J$_2$=12.8 Hz), 3.82-3.80 (m, 5H), 3.19-3.13 (m, 2H), 2.12-1.94 (m, 3H), 1.49-1.46 (m, 2H), 1.27-1.26 (m, 5H), 0.65 (d, 2H, J=7.2 Hz), 0.36-0.34 (m, 2H).

Example 38

N-(1-(1-(2-(3-cyanophenyl)pyrimidin-4-yl)piperidin-4-yl)ethyl)-3-(cyclopropylmethoxy)-5-methoxybenzamide

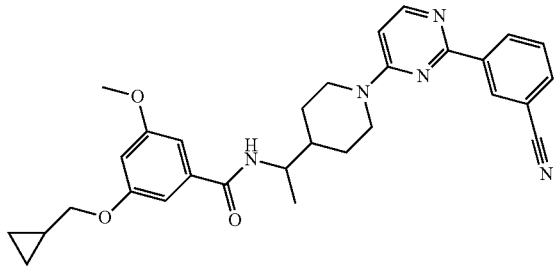 [SMILES: COc1cc(OCC2CC2)cc(C(=O)NC(C)C2CCN(c3ccnc(-c4cccc(C#N)c4)n3)CC2)c1]

i) A solution of 3-(cyclopropylmethoxy)-5-methoxy-N-(1-(piperidin-4-yl)ethyl)benzamide 2,2,2-trifluoroacetate (Example 36, step ii, 2.0 g), diethyl amine (3 ml) and 2,4-dichloro-pyrimidine (550 mg) in CH$_3$CN (80 ml) was stirred at room temperature for 30 minutes. 30 mL H$_2$O was added and the product was extracted into ethyl acetate. The combined organic layers were washed with brine, dried over Na$_2$SO$_4$ and concentrated under reduced pressure. The residue was purified by using normal phase chromatography eluting with petroleum ether containing 15% ethyl acetate to give N-(1-(1-(2-chloropyrimidin-4-yl)piperidin-4-yl)ethyl)-3-(cyclopropylmethoxy)-5-methoxybenzamide (740 mg) as a white solid.

ii) Analogous to a procedure described in Example 33, step iv, the title compound N-(1-(1-(2-(3-cyanophenyl)pyrimidin-4-yl)piperidin-4-yl)ethyl)-3-(cyclopropylmethoxy)-5-methoxybenzamide was prepared.

$^1$H NMR (CDCl$_3$): δ 8.62 (d, 1H, J=8.0 Hz), 8.55 (s, 1H), 7.89 (d, 1H, J=8.0 Hz), 7.73 (t, 1H, J=8.0 Hz), 6.86 (dd, 2H, J$_1$=J$_2$=2.0 Hz), 6.68 (d, 1H, J=7.2 Hz), 6.59 (t, 1H, J=2.0 Hz), 5.91 (d, 1H, J=8.8 Hz), 4.23 (dd, 2H, J$_1$=J$_2$=7.2 Hz), 3.82 (s, 5H), 3.20-3.15 (m, 2H), 2.08-1.96 (m, 3H), 1.49 (dd, 2H, J$_1$=11.6 Hz, J$_2$=10.0 Hz), 1.28 (d, 4H, J=6.8 Hz), 0.66 (d, 2H, J=6.8 Hz), 0.35 (d, 2H, J=5.6 Hz).

Example 39

Following a procedure analogous to that described in Example 38, the following compound was prepared.

N-(1-(1-(2-(3-(1H-pyrazol-1-yl)phenyl)pyrimidin-4-yl)piperidin-4-yl)ethyl)-3-(cyclopropylmethoxy)-5-methoxybenzamide

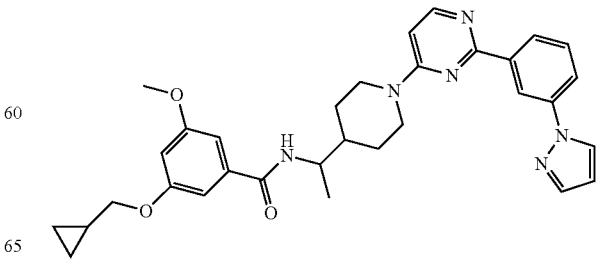

$^1$H NMR (CDCl$_3$): δ 8.69-8.95 (m, 2H), 8.39 (d, 1H, J=2.4 Hz), 8.19-8.13 (m, 2H), 7.75 (d, 1H, J=1.2 Hz), 7.64 (t, 1H, J$_1$=J$_2$=8.0 Hz), 6.86 (dd, 2H, J$_1$=2.0 Hz, J$_2$=2.4 Hz), 6.66 (s, 1H), 6.58 (s, 1H), 6.53 (t, 1H, J$_1$=1.6 Hz), 5.91 (d, 1H, J=8.8 Hz), 4.24-4.13 (m, 1H), 3.82 (s, 5H), 3.25-3.06 (m, 2H), 2.07-1.96 (m, 3H), 1.49 (dd, 2H, J$_1$=12.8 Hz, J$_2$=8.8 Hz), 1.27 (d, 4H, J=6.8 Hz), 0.65-0.63 (m, 2H), 0.35-0.34 (m, 2H).

Example 40

N-((1-(4-(3-(1H-imidazol-2-yl)phenyl)-1,3,5-triazin-2-yl)piperidin-4-yl)methyl)-3-(cyclopropylmethoxy)-5-methoxybenzamide 2,2,2-trifluoroacetate

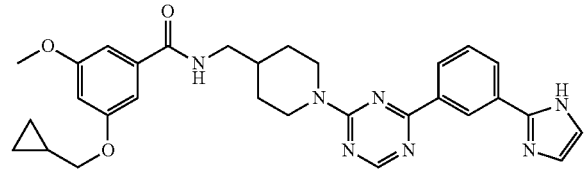 [SMILES: COc1cc(OCC2CC2)cc(C(=O)NCC2CCN(c3ncnc(-c4cccc(-c5ncc[nH]5)c4)n3)CC2)c1]

i) To a solution of N-((1-(4-chloro-1,3,5-triazin-2-yl)piperidin-4-yl)methyl)-3-(cyclopropylmethoxy)-5-methoxybenzamide (Example 31, step v, 150 mg, 0.35 mmol) in CH$_3$CN H$_2$O (4 ml, 3/1) were added 2-(3-(4,4,5,5-tetramethyl-1,3,2-dioxaborolan-2-yl)phenyl)-1-((2-(trimethylsilyl)ethoxy)methyl)-1H-imidazole (Example 9, 140 mg, 0.35 mmol), Na$_2$CO$_3$ (73 mg, 0.70 mmol) and Pd(PPh$_3$)$_2$Cl$_2$ (12 mg, 0.018 mmol) under a nitrogen atmosphere. The reaction mixture was stirred at 150° C. for 10 minutes in a microwave reactor. After cooling to room temperature the mixture was filtered, the filtrate dried over Na$_2$SO$_4$ and the solvents were removed under reduced pressure. The residue was purified by using prep HPLC to give 3-(cyclopropylmethoxy)-5-methoxy-N-((1-(4-(3-(1-((2-(trimethylsilyl)ethoxy)methyl)-1H-imidazol-2-yl)phenyl)-1,3,5-triazin-2-yl)piperidin-4-yl)methyl)benzamide (35 mg) as a solid.

ii) To a solution of the product obtained in the previous step (35 mg, 0.052 mmol) in EtOH (2 ml), was added concentrated HCl (2 ml) and the reaction mixture was stirred at room temperature overnight. The pH was adjusted to ph=4 by adding solid KOH. The resulting mixture was filtered and the filtrate was concentrated under reduced pressure. The residue was purified by using prep HPLC to give the title compound N-((1-(4-(3-(1H-imidazol-2-yl)phenyl)-1,3,5-triazin-2-yl)piperidin-4-yl)methyl)-3-(cyclopropylmethoxy)-5-methoxybenzamide trifluoro acetate (10 mg) as a white solid.

$^1$H NMR (CDCl$_3$): δ 8.96 (s, 1H), 8.63 (s, 1H), 8.46 (d, 1H, J=3.6 Hz), 8.36 (d, 1H, J=3.8 Hz), 7.57 (s, 1H), 7.35 (s, 2H), 6.90 (s, 2H), 6.59 (s, 1H), 6.57 (s, 1H), 5.08 (d, 1H, J=6.0 Hz), 4.97 (d, 1H, J=6.2 Hz), 3.81 (s, 5H), 3.42 (s, 2H), 3.21-3.16 (m, 2H), 2.11-2.00 (m, 3H), 1.38 (d, 2H, J=6.2 Hz), 1.26 (d, 2H, J=1.6 Hz), 0.67-0.63 (m, 2H), 0.36-0.34 (m, 2H).

Example 41

Following a procedure analogous to that described in Example 40, the following compound was prepared.

N-((1-(2-(3-(1H-imidazol-2-yl)phenyl)-5-fluoropyrimidin-4-yl)piperidin-4-yl)methyl)-3-(cyclopropylmethoxy)-5-methoxybenzamide 2,2,2-trifluoroacetate

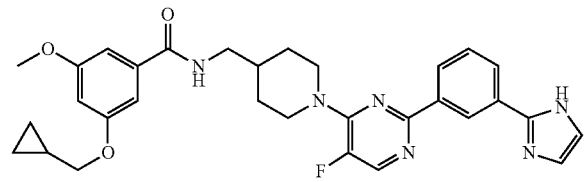 [SMILES: COc1cc(OCC2CC2)cc(C(=O)NCC2CCN(c3nc(-c4cccc(-c5ncc[nH]5)c4)ncc3F)CC2)c1]

$^1$H NMR (CDCl$_3$): δ 8.99 (s, 1H), 8.55 (d, 1H, J=3.6 Hz), 8.24 (d, 1H, J=3.6 Hz), 8.16 (d, 1H, J=3.6 Hz), 7.67 (t, 1H, J=8.0 Hz), 7.25 (s, 2H), 6.88 (s, 1H), 6.58 (s, 1H), 6.49 (s, 1H), 4.94 (d, 2H, J=5.4 Hz), 3.80 (s, 5H), 3.42 (t, 2H, J=6.4 Hz), 3.33 (t, 2H, J=11.4 Hz), 2.17 (d, 1H, J=2.1 Hz), 2.08 (d, 2H, J=6.6 Hz), 1.51 (d, 2H, J=5.6 Hz), 1.25 (m, 1H), 0.65-0.63 (m, 2H), 0.34-0.32 (m, 2H).

Example 42

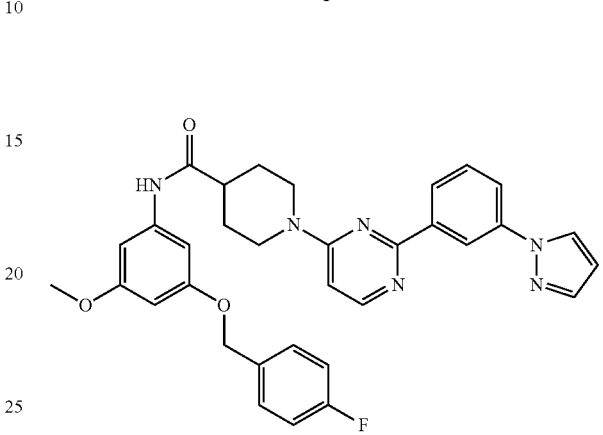

1-(2-(3-(1H-pyrazol-1-yl)phenyl)pyrimidin-4-yl)-N-(3-(4-fluorobenzoxy)-5-methoxyphenyl)piperidine-4-carboxamide i) Ethyl-isonipecotinate (2.94 g, 18.7 mmol) was added to a solution of 4-chloro-2-methylthiopyrimidine (2.5 g, 15.6 mmol) and triethyl amine (2.6 ml, 18.7 mmol) in dioxane (20 ml) and the mixture was heated to 80° C. for 4 hours. After cooling to ambient temperature, the solvents were removed under reduced pressure. The residue was dissolved in diethyl ether and washed with 0.1 N HCl, brine and dried over MgSO$_4$. The solvent was removed under reduced pressure to give ethyl 1-(2-(methylthio)pyrimidin-4-yl)piperidine-4-carboxylate, as an off white oil (3.9 g).

ii) A solution of the product obtained in the previous step (250 mg, 0.89 mmol), copper(I)-thiophene-2-carboxylate (252 mg, 1.3 mmol) and 3-(1H-pyrazol-1-yl)phenylboronic acid (318 mg, 1.3 mmol) in THF (5 ml) was purged with nitrogen gas for 10 minutes. Tetrakis(triphenylphosphine) palladium(0) (51 mg, 0.044 mmol) was added and the mixture was heated to 85° C. for 75 minutes by microwave irradiation. Ethyl acetate was added and the mixture was filtered through celite. The organic phase was washed with a saturated aqueous sodium bicarbonate solution and then dried by passing through a hydrophobic frit. The solution was concentrated under reduced pressure to give a crude residue that was purified by normal phase chromatography, eluting with CH$_2$Cl$_2$ containing an increasing amount of ethyl acetate to give ethyl 1-(2-(3-(1H-pyrazol-1-yl)phenyl)pyrimidin-4-yl)piperidine-4-carboxylate, as an off white solid (249 mg).

iii) To a solution of the product obtained in the previous step (1.37 g, 3.63 mmol) in ethanol (20 ml) was added a 1 N solution of sodium hydroxide (9 ml, 9 mmol) and the mixture was stirred at room temperature for 4 hours. After completion the reaction mixture was concentrated under reduced pres sure and the residue obtained was dissolved in water, cooled and acidified to pH 5 with 1 N HCl to give a white precipitate. The solid was collected by filtration, washed with water and diethyl ether before drying under reduced pressure to give 1-(2-(3-(1H-pyrazol-1-yl)phenyl)pyrimidin-4-yl)piperidine-4-carboxylic acid, as an off white solid (855 mg).

iv) A mixture of the product obtained in the previous step (495 mg, 1.42 mmol), HATU (650 mg, 1.70 mmol) and diisopropylethyl amine (620 ul, 3.54 mmol) in $CH_2Cl_2$ (10 ml) was stirred at room temperature for 20 minutes. 3-(tert-butyldimethylsiloxy)-5-methoxyaniline (Example 20, 366 mg, 1.45 mmol) was added and the mixture was stirred for 24 hours. The reaction mixture was diluted with $CH_2Cl_2$, washed with a saturated solution of sodium bicarbonate and the combined organic phases were passed through a hydrophobic frit. The solvent was removed under reduced pressure, to give a crude residue that was purified by normal phase chromatography, eluting with iso-hexane and increasing amounts of ethyl acetate to give 1-(2-(3-(1H-pyrazol-1-yl)phenyl)pyrimidin-4-yl)-N-(3-(tert-butyldimethylsiloxy)-5-methoxyphenyl)piperidine-4-carboxamide, as a white foam (970 mg).

v) To a solution of the product obtained in the previous step (970 mg, 1.66 mmol) in $CH_2Cl_2$ (20 ml) was added a 4 M solution of HCl in dioxane (5 ml, 20 mmol) and the mixture was stirred at room temperature for 36 hours. The solvents were removed under reduced pressure and the residue obtained was dissolved in a mixture of $CH_2Cl_2$ and diisopropylethyl amine (5:1). The organic phase were washed with water and then dried by passing through a hydrophobic frit. The solvents were removed under reduced pressure to give a yellow solid (130 mg). A precipitate was formed in the aqueous phase which was filtered, washed with water and diethyl ether before drying under reduced pressure. The solids obtained were combined to give 1-(2-(3-(1H-pyrazol-1-yl)phenyl)pyrimidin-4-yl)-N-(3-hydroxy-5-methoxyphenyl)piperidine-4-carboxamide, as a pale yellow solid (512 mg).

vi) An aliquot (2 ml, 0.11 mmol) was taken from a stock solution of the product obtained in the previous step in DMF and dispensed into a reaction tube containing cesium carbonate (70 mg, 0.22 mmol). 4-Fluorobenzyl chloride (14 ul, 0.1171 mmol) was added and the mixture was heated to 40° C. for 18 hours. The solvent was removed under reduced pressure and the residue obtained was partitioned between $CH_2Cl_2$ and water. The organic phase was filtered through a hydrophobic frit and the solvents were removed under reduced pressure. The crude residue was purified by normal phase chromatography, eluting with iso-hexane and increasing amounts of ethyl acetate to give target compound 1-(2-(3-(1H-pyrazol-1-yl)phenyl)pyrimidin-4-yl)-N-(3-(4-fluorobenzoxy)-5-methoxyphenyl)piperidine-4-carboxamide, as a white solid (10.4 mg).

$^1$H NMR (DMSO-d): δ 9.95 (1H, s), 9.09 (1H, s), 8.75 (1H, d, J=4.75 Hz), 8.46-8.36 (2H, m), 8.20 (1H, d, J=7.80 Hz), 8.05 (1H, d, J=7.99 Hz), 7.95 (1H, td, J=7.69, 1.82 Hz), 7.64 (1H, t, J=7.76 Hz), 7.49-7.32 (6H, m), 7.00 (1H, s), 6.93-6.86 (2H, m), 6.32 (1H, t, J=2.22 Hz), 5.08 (2H, s), 4.65 (2H, bs), 3.73 (3H, s), 3.10 (2H, t, J=12.63 Hz), 2.75-2.66 (1H, m), 1.97 (2H, d, J=12.94 Hz), 1.73-1.60 (2H, m).

Example 43

Following a procedure analogous to that described in Example 42, the following compound was prepared.

1-(2-(3-(1H-pyrazol-1-yl)phenyl)pyrimidin-4-yl)-N-(3-methoxy-5-((5-methylisoxazol-3-yl)methoxy)phenyl)piperidine-4-carboxamide

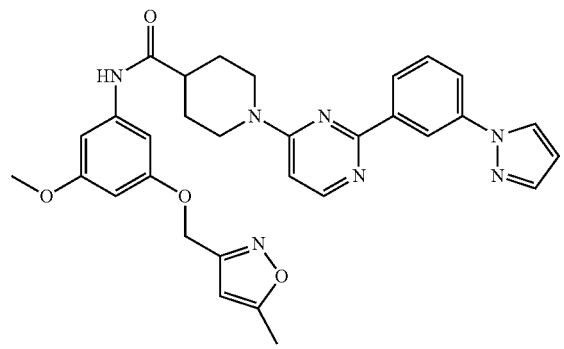 [SMILES: COc1cc(NC(=O)C2CCN(c3ccnc(-c4cccc(-n5cccn5)c4)n3)CC2)cc(OCc2cc(C)on2)c1]

$^1$H NMR (DMSO-d): δ 9.97 (1H, s), 8.79 (1H, t, J=1.86 Hz), 8.60 (1H, d, J=2.54 Hz), 8.37 (1H, dd, J=11.09, 6.16 Hz), 8.31 (1H, d, J=7.88 Hz), 7.96 (1H, dd, J=8.04, 2.27 Hz), 7.82 (1H, d, J=1.73 Hz), 7.66-7.60 (1H, m), 6.99-6.89 (3H, m), 6.61 (1H, t, J=2.09 Hz), 6.35-6.32 (2H, m), 5.11 (2H, s), 4.86-4.58 (2H, m), 3.74 (3H, s), 3.09 (2H, t, J=12.60 Hz), 2.77-2.67 (1H, m), 2.46-2.38 (3H, m), 1.96 (2H, d, J=12.98 Hz), 1.73-1.60 (2H, m).

Example 44

1-(2-(3-(1H-pyrazol-1-yl)phenyl)pyrimidin-4-yl)-N-(3-isopropoxy-5-methoxyphenyl)piperidine-4-carboxamide

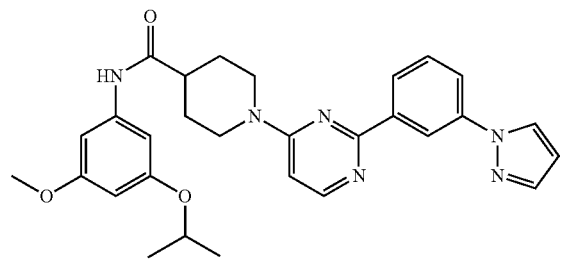 [SMILES: COc1cc(NC(=O)C2CCN(c3ccnc(-c4cccc(-n5cccn5)c4)n3)CC2)cc(OC(C)C)c1]

i) To a solution of 3-amino-5-methoxyphenol (Example 20, step i, 140 mg, 1.0 mmol), triphenylphosphine (390 mg, 1.5 mmol) and propan-2-ol (90 ul, 1.2 mmol) in THF (3 ml) was added portion wise di-tert-butyl diazocarboxylate (345 mg, 1.5 mmol) at room temperature. After stirring for 3 hours the reaction mixture was diluted with ethyl acetate and extracted with a 1N aqueous solution of HCl. The combined aqueous phases were brought to pH=10 with a aqueous solution of 1N NaOH and then extracted with ethyl acetate. The combined organics were filtered through a hydrophobic frit and the solvents were removed under reduced pressure to give 3-isopropoxy-5-methoxyaniline as a light brown oil (169 mg).

ii) A mixture of the product obtained in the previous step (56 mg, 0.16 mmol), HATU (72 mg, 0.19 mmol) and diisopropylethyl amine (70 ul, 0.39 mmol) in CH$_2$Cl$_2$ (5 ml) was stirred at ambient temperature for 15 minutes. 1-(2-(3-(1H-pyrazol-1-yl)phenyl)pyrimidin-4-yl)piperidine-4-carboxylic acid (Example 20, step iii, 34 mg, 0.19 mmol) was added and the mixture was stirred at ambient temperature for 3 hours. The reaction mixture was diluted with CH$_2$Cl$_2$ (3 ml) and washed with a saturated solution of sodium bicarbonate (5 ml). The aqueous phase was re-extracted with CH$_2$Cl$_2$ (5 ml) and the combined organics were passed through a hydrophobic frit and then concentrated to dryness under reduced pressure. The crude residue obtained was purified by normal phase chromatography, eluting with iso-hexane and increasing amounts of ethyl acetate to give an off white solid. The solid was triturated with diethyl ether to give the title compound 1-(2-(3-(1H-pyrazol-1-yl)phenyl)pyrimidin-4-yl)-N-(3-isopropoxy-5-methoxyphenyl)piperidine-4-carboxamide as an off white solid (27.6 mg).

Following a procedure analogous to that described in Example 44, the following compound was prepared.

Example 45

1-(2-(3-(1H-pyrazol-1-yl)phenyl)pyrimidin-4-yl)-N-(3-(cyclohexylmethoxy)-5-methoxyphenyl)piperidine-4-carboxamide

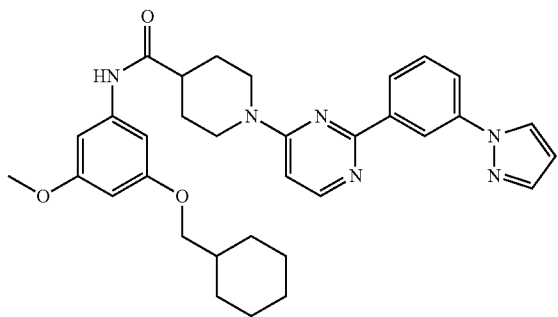 [SMILES: COc1cc(NC(=O)C2CCN(c3ccnc(-c4cccc(-n5cccn5)c4)n3)CC2)cc(OCC2CCCCC2)c1]

$^1$H NMR (CDCl$_3$): δ 8.65 (1H, s), 8.34 (2H, t, J=7.71 Hz), 8.06 (1H, d, J=2.47 Hz), 7.86 (1H, d, J=8.19 Hz), 7.75 (1H, d, J=1.71 Hz), 7.54 (1H, t, J=7.95 Hz), 7.15 (1H, s), 6.80 (1H, s), 6.72 (1H, s), 6.51-6.47 (2H, m), 6.24 (1H, s), 4.61 (2H, bd, J=12.95 Hz), 3.78-3.69 (5H, m), 3.09 (2H, t, J=12.53 Hz), 2.55 (1H, s), 2.07 (2H, d, J=13.02 Hz), 1.95-1.80 (4H, m), 1.75 (4H, d, J=13.54 Hz), 1.31-1.18 (3H, m), 1.04 (2H, t, J=11.88 Hz).

Example 46

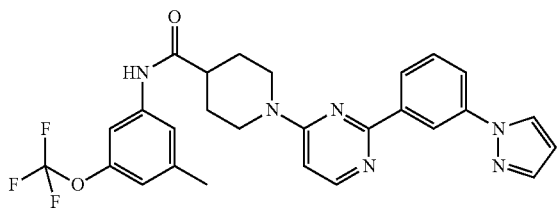 [SMILES: Cc1cc(NC(=O)C2CCN(c3ccnc(-c4cccc(-n5cccn5)c4)n3)CC2)cc(OC(F)(F)F)c1]

1-(2-(3-(1H-pyrazol-1-yl)phenyl)pyrimidin-4-yl)-N-(3-methyl-5-(trifluoromethoxy)phenyl)piperidine-4-carboxamide i) To a solution of ethyl piperidine-4-carboxylate (13.0 g, 82.69 mmol,) in ethanol (130 ml) were added Et$_3$N (17.29 ml, 124 mmol) and 2,4-dichloropyrimidine (13.55 g, 90.96 mmol). After stirring for 8 minutes at 80° C., the solvent was removed under reduced pressure and purified by normal phase chromatography, eluting with Heptane with 50% ethyl acetate to give compound ethyl 1-(2-chloropyrimidin-4-yl)piperidine-4-carboxylate (19.45 g, 76%) as a colourless oil.

ii) To a mixture of the compound obtained in the previous step (1.0 g, 3.707 mmol) and 1-(3-(4,4,5,5-tetramethyl-1,3,2-dioxaborolan-2-yl)phenyl)-1H-pyrazole (1.84 g, 6.811 mmol) in dioxane (25 ml) were added DMF (2.0 ml), Pd(PPh$_3$)$_4$ (216 mg, 0.190 mmol), H$_2$O (2.0 ml) and K$_2$CO$_3$ (1.53 g, 11.12 mmol). After purging the reaction mixture with N$_2$ for 10 minutes, the reaction mixture was heated at reflux temperature for 18 h. After cooling to ambient temperature, the mixture was concentrated under reduced pressure. The residue was extracted into dichloromethane, dried over Na$_2$SO$_4$ and concentrated under reduced pressure. The resulting crude residue was purified by normal phase chromatography, eluting with heptane containing increasing amounts of ethyl acetate to give compound ethyl 1-(2-(3-(1H-pyrazol-1-yl)phenyl)pyrimidin-4-yl)piperidine-4-carboxylate (0.84 g) as a colourless oil.

iii) To a solution of the compound obtained in the previous step (0.84 g, 2.26 mmol) in MeOH (20 ml) was added 1N NaOH (2.45 ml) and the reaction mixture was stirred at room temperature for 4 h. The reaction mixture was concentrated under reduced pressure and acidified by the addition of 2M aqueous solution of HCl. The precipitated white solids were collected by filtration and washed with diethyl ether and dried under reduced pressure to give 1-(2-(3-(1H-pyrazol-1-yl)phenyl)pyrimidin-4-yl)piperidine-4-carboxylic acid (0.712 g) as a white solid.

iv) To a suspension of the product obtained in the previous step (50 mg, 0.1432 mmol) in CH$_2$Cl$_2$ (15 ml) were added DIPEA (55 mg, 0.4296 mmol), TBTU (138 mg, 0.4296 mmol), 3-methyl-5-(trifluoromethoxy)aniline (82 mg, 0.4296 mmol) and 5 drops of DMF. The reaction mixture was stirred overnight at room temperature. The mixture was concentrated under reduced pressure and saturated aqueous NaHCO$_3$ was added. The product was extracted into CH$_2$Cl$_2$ and the organic phase was dried over Na$_2$SO$_4$ and concentrated under reduced pressure. The resulting crude residue was purified by normal phase chromatography, eluting with CH$_2$Cl$_2$ containing increasing amounts of MeOH to give the title compound 1-(2-(3-(1H-pyrazol-1-yl)phenyl)pyrimidin-4-yl)-N-(3-methyl-5-(trifluoromethoxy)phenyl)piperidine-4-carboxamide as a as a white solid (22 mg).

$^1$H NMR (CDCl$_3$): δ 8.68 (s, 1H), 8.34 (d, 2H), 8.08 (s, 1H), 7.86 (d, 1H), 7.88 (s, 1H), 7.64 (s, 1H), 7.56 (t, 1H), 7.37 (s, 1H), 7.28 (d, 1H), 6.80 (s, 1H), 6.48 (m, 2H), 4.58 (d, 2H), 3.02 (t, 2H), 2.46 (m, 1H), 2.37 (s, 3H), 2.00 (m, 2H), 1.90 (m, 2H).

Example 47

Following a procedure analogous to that described in Example 46, the following compounds were prepared.

47A: 1-(2-(3-(1H-pyrazol-1-yl)phenyl)pyrimidin-4-yl)-N-(3-(2,2-difluoroethoxy)phenyl)piperidine-4-carboxamide

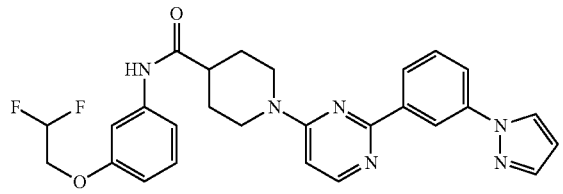 [SMILES: O=C(Nc1cccc(OCC(F)F)c1)C1CCN(c2ccnc(-c3cccc(-n4cccn4)c3)n2)CC1]

¹H NMR (CDCl₃): δ 8.72 (s, 1H), 8.37 (t, 2H), 8.15 (s, 1H), 7.92 (d, 2H), 7.78 (s, 1H), 7.58 (t, 1H), 7.24 (s, 1H), 7.15 (t, 1H), 7.00 (d, 1H), 6.72 (d, 1H), 6.54 (m, 2H), 6.32-5.88 (m, 2H), 4.62 (d, 2H), 4.12 (t, 2H), 3.16 (t, 2H), 2.60 (m, 1H), 2.10 (m, 2H), 1.94 (m, 2H).

47B: 1-(2-(3-(1H-pyrazol-1-yl)phenyl)pyrimidin-4-yl)-N-(3-fluoro-5-methoxyphenyl)piperidine-4-carboxamide

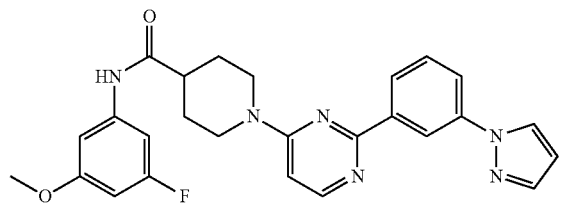 [SMILES: COc1cc(F)cc(NC(=O)C2CCN(c3ccnc(-c4cccc(-n5cccn5)c4)n3)CC2)c1]

¹H NMR (CDCl₃): δ 8.70 (s, 1H), 8.32 (t, 2H), 8.10 (s, 1H), 7.90 (d, 1H), 7.80 (s, 1H), 7.58 (t, 1H), 7.38 (s, 1H), 6.98 (m, 2H), 6.50 (m, 2H), 6.42 (d, 2H), 4.62 (m, 2H), 3.80 (s, 3H), 3.10 (t, 2H), 2.58 (t, 1H), 2.06 (m, 2H), 1.88 (m, 2H).

47C: 1-(2-(3-(1H-pyrazol-1-yl)phenylpyrimidin-4-yl)-N-(3-methoxy-5-(5-methyl-2H-tetrazol-2-yl)phenyl)piperidine-4-carboxamide

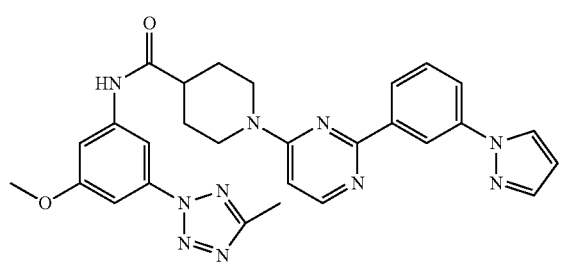 [SMILES: COc1cc(NC(=O)C2CCN(c3ccnc(-c4cccc(-n5cccn5)c4)n3)CC2)cc(-n2nnc(C)n2)c1]

¹H NMR (CDCl₃): δ 9.24 (s, 1H), 8.78 (s, 1H), 8.32 (s, 1H), 8.24 (m 2H), 8.00 (d, 2H), 7.74 (s, 1H), 7.64 (s, 1H), 7.58 (t, 1H), 7.24 (s, 1H), 6.70 (s, 1H), 6.64 (d, 2H), 6.44 (s, 1H), 4.60 (d, 2H), 3.82 (s, 3H), 3.28 (t, 2H), 2.92 (m, 1H), 2.62 (s, 3H), 2.18 (m, 2H), 2.02 (t, 2H).

47D: 1-(2-(3-(1H-pyrazol-1-yl)phenyl)pyrimidin-4-yl)-N-(3,5-dimethylphenyl)piperidine-4-carboxamide

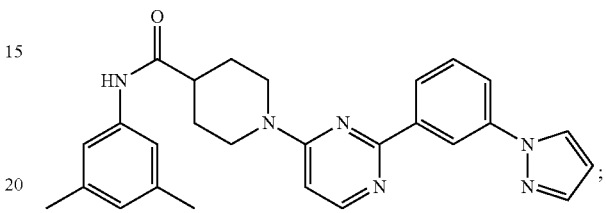

MS (ESI) me: 453.1 (M+H)+.

47E: 1-(2-(3-(1H-pyrazol-1-yl)phenyl)pyrimidin-4-yl)-N-(3-methoxy-5-(trifluoromethyl)phenyl) piperidine-4-carboxamide

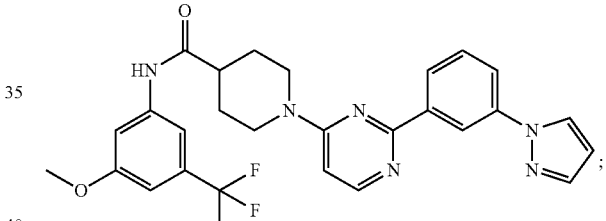

MS (ESI) me: 523.52 (M+H)+.

Example 48

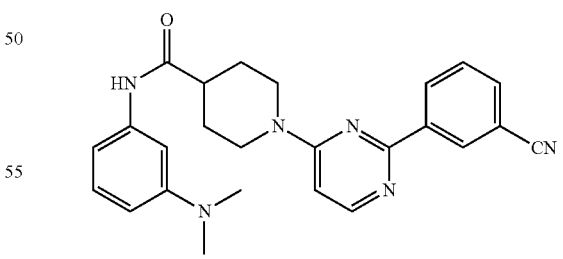

1-(2-(3-cyanophenyl)pyrimidin-4-yl)-N-(3-(dimethylamino)phenyl)piperidine-4-carboxamide i) Following a procedure analogous to that described in Example 46, using 3-cyanophenylboronic acid and N1,N1-dimethylbenzene-1,3-diamine, the title compound 1-(2-(3- cyanophenyl)pyrimidin-4-yl)-N-(3-(dimethylamino)phenyl)piperidine-4-carboxamide was prepared. MS (ESI) me: 427.3 (M+H)+.

Example 49

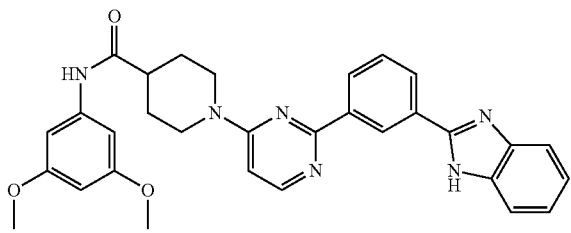 [SMILES: COc1cc(NC(=O)C2CCN(c3ccnc(-c4cccc(-c5nc6ccccc6[nH]5)c4)n3)CC2)cc(OC)c1]

1-(2-(3-(1H-benzo[d]imidazol-2-yl)phenyl)pyrimidin-4-yl)-N-(3,5-dimethoxyphenyl)piperidine-4-carboxamide i) To a solution of ethyl piperidine-4-carboxylate (13.0 g, 82.69 mmol,) in ethanol (130 ml) were added $Et_3N$ (17.29 ml, 124 mmol) and 2,4-dichloropyrimidine (13.55 g, 90.96 mmol). After stirring for 8 minutes at 80° C., the solvent was removed under reduced pressure and the crude product was purified by normal phase chromatography, eluting with Heptane with 50% ethyl acetate to give compound ethyl 1-(2-chloropyrimidin-4-yl)piperidine-4-carboxylate (19.45 g) as a colourless oil.

ii) To a solution of the compound obtained in the previous step (10 g, 37.07 mmol) in MeOH (70 ml) was added a 1N aqueous solution of NaOH (35 ml) and the reaction mixture was stirred at room temperature for 4 h. The reaction mixture was concentrated under reduced pressure and acidified by the addition of a 2M aqueous solution of HCl. The aqueous mixture was extracted with $CH_2Cl_2$:MeOH (9:1). The combined organic layers were dried over $Na_2SO_4$ and concentrated under reduced pressure to give 1-(2-chloropyrimidin-4-yl)piperidine-4-carboxylic acid (8.87 g) as a white solid.

iii) To a suspension of the compound obtained in the previous step (8.87 g, 36.7 mmol) in dichloromethane (300 ml) were added N,N-diisopropylethyl amine (14.23 g, 110.1 mmol), 3,5-dimethoxyaniline (16.87 g, 110.1 mmol) and TBTU (17.68 g, 55.1 mmol). After stirring for 17 h at room temperature the reaction mixture quenched by the addition of a saturated aqueous solution of sodiumbicarbonate and extracted with dichloromethane. The combined organic layers were dried over Na2SO4 and evaporated under reduced pressure. The crude product was purified by normal phase chromatography, eluting with Heptane with 50% ethyl acetate to give 1-(2-chloropyrimidin-4-yl)-N-(3,5-dimethoxyphenyl)piperidine-4-carboxamide (6.99 g) as a white solid.

iv) 2-bromo-1H-benzo[d]imidazole (177 mg, 0.9 mmol), bispinacolato diboron (250 mg, 0.99 mmol) and KOAc (265 mg, 2.7 mmol) were dissolved in dioxane (9 ml). After purging with $N_2$, $Pd(dppf)Cl_2$ (37 mg, 0.045 mmol) was added. After stirring overnight at reflux temperature the reaction was cooled to room temperature the reaction mixture was diluted with some ethyl acetate (20 ml). The mixture was filtrated through a pad of celite and the solvent was evaporated under reduced pressure to give 2-(4,4,5,5-tetramethyl-1,3,2-dioxaborolan-2-yl)-1H-benzo[d]imidazole as a black oil. The crude product was used in the next step without further purification.

v) A solution of the crude boronic ester obtained in the previous step in dioxane (8 ml) and water (800 μL) was added to a flask containing 1-(2-chloropyrimidin-4-yl)-N-(3,5-dimethoxyphenyl)piperidine-4-carboxamide (Example 49, step iii, 100 mg, 0.52 mmol), $BF_4.P(t-Bu_4)$ (18 mg, 0.06 mmol) and $Cs_2CO_3$ (260 mg, 0.78 mmol). After purging with $N_2$, $Pd(dba)_2$ (24 mg, 0.04 mmol) was added and the reaction mixture was heated for 15 minutes to 140° C. in a microwave reactor. After cooling down to room temperature the reaction mixture was diluted with ethyl acetate (20 ml). The mixture was filtrated through a pad of celite and the solvent was evaporated under reduced pressure. The product was purified by prep-HPLC to give the title compound 1-(2-(3-(1H-benzo[d]imidazol-2-yl)phenyl)pyrimidin-4-yl)-N-(3,5-dimethoxyphenyl)piperidine-4-carboxamide (5 mg) as a white solid (20 mg).

$^1$H NMR (DMSO): δ 9.35 (t, NH), 8.57 (s, 1H), 8.44 (m, 1H), 8.31 (d, 1H), 8.20 (d, 1H), 7.68 (s, 1H), 7.65 (m, 2H), 7.29 (m, 2H), 6.84 (d, 2H), 6.80 (d, 1H), 6.26 (t, 1H), 4.86 (m, 2H), 3.76 (s, 6H), 3.16 (m, 2H), 2.76 (m, 1H), 2.04 (m, 2H), 1.86 (m, 2H).

Example 50

Following a procedure analogous to that described in Example 49, the following compound was prepared.

50A: N-(3,5-dimethoxyphenyl)-1-(2-(3-(oxazol-2-yl)phenyl)pyrimidin-4-yl)piperidine-4-carboxamide

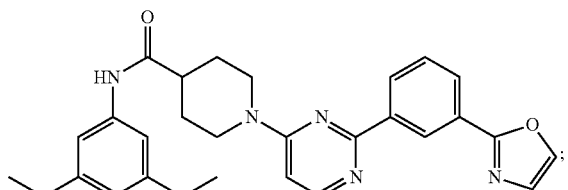

MS (ESI) mz: 486.3 (M+H$^+$).

50B: N-(3,5-dimethoxyphenyl)-1-(2-(2-methylpyridin-4-yl)pyrimidin-4-yl)piperidine-4-carboxamide

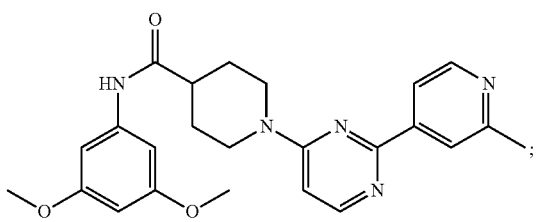

MS (ESI) mz: 434.6 (M+H$^+$).

Example 51

Following a procedure analogous to that described in Example 46, the following compound was prepared.

51: 1-(2-(3-(1H-pyrazol-1-yl)phenyl)pyrimidin-4-yl)-N-(3,5-dimethoxyphenyl) piperidine-4-carboxamide

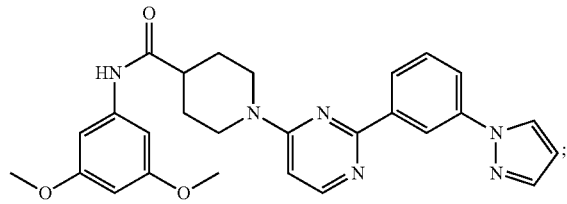 [SMILES: COc1cc(NC(=O)C2CCN(c3ccnc(-c4cccc(-n5cccn5)c4)n3)CC2)cc(OC)c1]

MS (ESI) mz: 448.2 (M+H+).

Example 52

Antagonistic Activity of Compounds at the Human FSH Receptor Expressed in Cho Cells Antagonistic activity of the compounds at the human FSH receptor was determined in Chinese Hamster Ovary (CHO) cells stably transfected with the human FSH receptor and cotransfected with a cAMP responsive element (CRE)/promotor directing the expression of a firefly luciferase reporter gene. Binding of the compounds to the Gs protein-coupled FSH receptor will result in an increase of cAMP, which in turn will induce an increased transactivation of the luciferase reporter. The cells (7,500 cells/well of a 384 well plate) were incubated in Dulbecco' minimal essential F12 modified medium (Invitrogen), supplemented with 1 µg/ml bovine insulin, 5 µg/ml human apo-transferrin, 100 U/ml penicillin G and 100 µg/ml streptomycin with the test compounds (concentration between 0.316 nM and 10.0 µM) in duplicate together with 49 µM recFSH (which, at this concentration in the absence of test compound, induces 80% of the maximal luciferase stimulation) in a humidified atmosphere (95%) at 5-7% $CO_2$ and 37° C. The final concentration of DMSO was 1%. After 4 hours of incubation, plates were allowed to adjust to room temperature for 1 hour. Then, SteadyLite (Perkin Elmer) solution was added to the wells and cells were allowed to lyse for at least 1 hour at room temperature. Subsequently, luciferase activity was measured in a luminescence counter. The signal is expressed as counts per second (cps). The IC50 (concentration of test compound causing half-maximal (50%) inhibition of the maximally attainable inhibition of the luciferase stimulation by the compound) and efficacy of the compounds were determined using the software program MathIQ (version 2.3, ID Business Solutions Limited).

All the N-piperidin-4-yl derivatives of the invention according to general Formula I and specifically disclosed in examples 11-25 and 28-51 are characterized by a pIC50 (negative logarithm of the IC50 value) of higher than 6.0. The N-piperidin-4-yl derivatives of examples 11, 12B, 14, 15C, 15D, 17B, 17C, 17D, 18, 19B, 19E, 21B, 22, 23A, 23C, 28C, 30C, 31, 32F, 32G, 32H, 32I, 33A, 33B, 33C, 33D, 33E, 34, 35, 42, 44, 45 and 46 showed a pIC50 between 7.0 and 8.0.

The N-piperidin-4-yl derivatives of examples 15A, 15B, 17A, 19C, 30D, 32C, 33A, 37, 38, 39, 40, 41, 43 and 51 have a pIC50 higher than 8.0.

Example 53

Functional Assay for Assessing hFSHR Antagonistic Activity of Test Compounds in Human Granulosa Cell Cultures Human granulosa cells were obtained in the course of follicular aspiration for retrieval of matured oocytes during routine IVF procedures approximately 36 hours after hCG administration to the patient. Follicular fluid was collected as one batch per patient and after oocyte removal centrifuged for 5 minutes at 350 g at room temperature (RT). The pellet was resuspended in 5 ml collagenase (0.1%) containing isolation medium, layered on 5 ml of Histopaque-1077 and centrifuged (450 g for 20 minutes, RT) to separate the granulosa cells from the erythrocytes. The granulosa cells and other mononuclear cells (e.g. lymphocytes) were obtained from the interface and washed once with isolation medium (450 g, 20 minutes). After aspiration of the supernatant, the pellet was resuspended in isolation medium and transported from the hospital to the laboratory. The granulosa cells are pelleted by centrifugation (350 g, 5 minutes) and resuspended in a small volume of culture medium with 10% fetal calf serum (FCS). To facilitate cell dispersal the suspension was subjected to gentle mechanical dissociation.

Cell viability was determined by Trypan Blue exclusion and the granulosa cells were plated at a density of 25.000 viable cells/200 µl/well in culture medium with 10% FCS in collagen coated 96-wells plates, and cultured at 37° C. under a humidified atmosphere supplemented with 5% $CO_2$. Every 72 hours the cells are washed once with pre-warmed culture medium to remove dead cells, debris and non-adherent cells. Seven days after the start of the culture, the cells are washed again with culture medium. Medium was aspirated and 250 µL isolation medium with isobutylmethylxanthine (IBMX) with human recombinant FSH (hrecFSH: 0 and 250 mU/mL) or with hrecFSH (250 mU/mL) in combination with Example 51 was incubated for an additional 48 hours at 37° C., 5% $CO_2$. All test conditions were performed in triplicate. Subsequently, supernatant was collected in 96 well plates. Finally 25 µL supernatant was transferred to a new 96 deep-well plate and used for the determination of cAMP levels with the cAMP EIA kit (Amersham Life Sciences, cat. no RPN 225). Immediately after aspiration of the supernatant of the granulosa cells, 150 µL culture medium supplemented with 10 µM testosterone, was added to the wells. After 2 hours of incubation at 37° C., 5% $CO_2$, the supernatant was collected and used for the determination of estradiol levels with an estradiol-ELISA (DRG instruments, art. no. EIA-2693). Supernatants were diluted 1:300 in Dulbecco's phosphate buffered saline (DPBS, Hyclone Cat. No. SH30028.03) and a self-made calibration curve of estradiol in DPBS was used for the determination of estradiol levels in the supernatants. Results for 1-(2-(3-(1H-pyrazol-1-yl)phenyl)pyrimidin-4-yl)-N-(3,5-dimethoxyphenyl) piperidine-4-carboxamide (Example 51) are shown in FIG. 1.

The invention claimed is:
1. A N-piperidin-4-yl compound having the Formula I

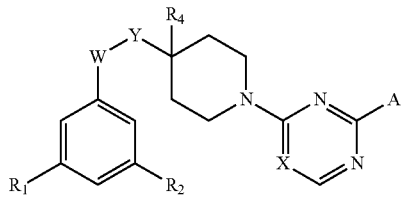

Formula I wherein
W is C(O)NH or NH(CO);
Y is CHR₃ or a bond;
X is N, CH, CF or CR₈;
A is a (hetero)aromatic group selected from

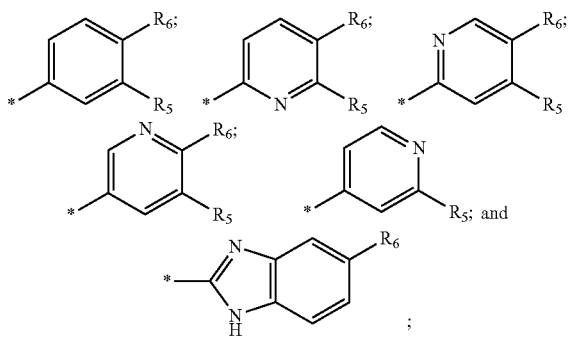

$R_1$ is H, halogen, $(C_{1-4})$alkyl, halo$(C_{1-4})$alkyl, $(C_{1-4})$alkyloxy or halo$(C_{1-4})$alkyloxy;
$R_2$ is H, halogen, di$(C_{1-4})$alkylamino, $(C_{2-4})$alkenyl, $(C_{2-4})$alkynyl, halo$(C_{1-4})$alkyl or $(C_{1-6})$alkyloxy, optionally substituted with one or more halogens, hydroxy or $(C_{1-4})$alkyloxy; or
$R_2$ is OCH₂R₇;
$R_3$ is H, $(C_{1-3})$alkyl or COOR₈;
$R_4$ is H, halogen or $(C_{1-3})$alkyl; or
$R_4$ forms together with $R_3$ and the carbon atoms to which they are bonded a $(C_{3-5})$cycloalkyl group;
$R_5$ is, halogen, $(C_{1-4})$alkyl, halo$(C_{1-4})$alkyl, hydroxy $(C_{1-4}$alkyl, CN, COOH, CONR₉, R₁₀, pyridyl or a 5-membered heteroaryl group comprising 1, 2 or 3 nitrogen atoms and optionally an oxygen or a sulfur atom;
$R_6$ is H, hydroxy or halogen; or
$R_6$ forms together with $R_5$ and the carbon atoms to which they are bonded a fused 5-membered heteroaryl group comprising 1 or 2 nitrogen atoms and optionally an oxygen or a sulfur atom;
$R_7$ is vinyl, ethynyl, cyano, $(C_{3-6})$cycloalkyl, CONR₁₁, R₁₂, CH₂NR₁₃R₁₄, phenyl or a 5 or 6-membered heteroaryl group comprising 1-3 heteroatoms selected from O, N and S;
each $R_8$ is independently $(C_{1-3})$alkyl;
$R_9$ is H or $(C_{1-6})$alkyl, optionally substituted with 1-3 halogens, hydroxyl or COOR₈;
$R_{10}$ is H, $(C_{1-3})$alkyl or a 5-membered heteroaryl group comprising 1-3 heteroatoms selected from N, S and O; or
$R_9$ and $R_{10}$ form together with the nitrogen atom to which they are bonded a saturated 5-7 membered ring;

$R_{11}$, $R_{12}$, $R_{13}$ and $R_{14}$ are independently selected from H or $(C_{1-3})$alkyl; or a pharmaceutically acceptable salt thereof.
2. The N-piperidin-4-yl compound of claim 1, wherein W is C(O)NH.
3. The N-piperidin-4-yl compound of claim 2, wherein $R_4$ is H.
4. The N-piperidin-4-yl compound of claim 3, wherein A is

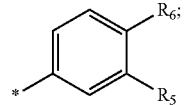

$R_5$ is CN or a 5-membered heteroaryl group comprising 2 nitrogen atoms; and $R_6$ is H.
5. The N-piperidin-4-yl compound of claim 4, wherein $R_5$ is 1H-pyrazol-1-yl, 1H-pyrazol-5-yl or 1H-imidazol-2-yl.
6. The N-piperidinyl-4-yl compound of claim 5, wherein $R_1$ is $(C_{1-4})$alkyloxy and $R_2$ is OCH₂R₇, wherein $R_7$ is $(C_{3-6})$cycloalkyl.
7. The N-piperidinyl-4-yl compound of claim 1 which is selected from
1-(2-(3-(1H-pyrazol-1-yl)phenyl)pyrimidin-4-yl)-N-(3-methoxy-5-((5-methylisoxazol-3-yl)methoxy)phenyl) piperidine-4-carboxamide;
N-((1-(2-(3-(1H-pyrazol-1-yl)phenyl)pyrimidin-4-yl)piperidin-4-yl)methyl)-3-(cyclopropylmethoxy)-5-methoxybenzamide;
N-((1-(2-(3-(1H-pyrazol-1-yl)phenyl)pyrimidin-4-yl)piperidin-4-yl)methyl)-3-methoxy-5-((5-methylisoxazol-3-yl)methoxy)benzamide;
N-((1-(4-(3-(1H-pyrazol-1-yl)phenyl)-1,3,5-triazin-2-yl)piperidin-4-yl)methyl)-3-(cyclopropylmethoxy)-5-methoxybenzamide;
N-((1-(4-(3-cyanophenyl)-1,3,5-triazin-2-yl)piperidin-4-yl)methyl)-3-methoxy-5-(2,2,2-trifluoroethoxy)benzamide;
N-((1-(2-(3-(1H-pyrazol-5-yl)phenyl)-5-fluoropyrimidin-4-yl)piperidin-4-yl)methyl)-3-(cyclopropylmethoxy)-5-methoxybenzamide;
3-(cyclopropylmethoxy)-5-methoxy-N-((1-(2-(3-(1-methyl-1H-pyrazol-3-ylcarbamoyl)phenyl)pyrimidin-4-yl)piperidin-4-yl)methyl)benzamide;
3-(cyclopropylmethoxy)-5-methoxy-N-((1-(2-(3-(4-methyl-1H-pyrazol-1-yl)phenyl)pyrimidin-4-yl)piperidin-4-yl)methyl)benzamide;
N-(1-(1-(4-(3-(1H-pyrazol-3-yl)phenyl)-1,3,5-triazin-2-yl)piperidin-4-yl)ethyl)-3-(cyclopropylmethoxy)-5-methoxybenzamide;
N-(1-(1-(2-(3-cyanophenyl)pyrimidin-4-yl)piperidin-4-yl)ethyl)-3-(cyclopropylmethoxy)-5-methoxybenzamide;
N-(1-(1-(2-(3-(1H-pyrazol-1-yl)phenyl)pyrimidin-4-yl) piperidin-4-yl)ethyl)-3-(cyclopropyl methoxy)-5-methoxybenzamide;
N-((1-(4-(3-(1H-imidazol-2-yl)phenyl)-1,3,5-triazin-2-yl)piperidin-4-yl)methyl)-3-(cyclopropylmethoxy)-5-methoxybenzamide 2,2,2-trifluoroacetate;
1-(2-(3-(1H-pyrazol-1-yl)phenyl)pyrimidin-4-yl)-N-(3,5-dimethoxyphenyl) piperidine-4-carboxamide; and
N-((1-(2-(3-(1H-imidazol-2-yl)phenyl)-5-fluoropyrimidin-4-yl)piperidin-4-yl)-methyl)-3-(cyclopropylmethoxy)-5-methoxybenzamide 2,2,2-trifluoroacetate;
or a pharmaceutically acceptable salt thereof.
8. A pharmaceutical composition comprising a N-piperidinyl-4-yl compound of claim 1 or a pharmaceutically acceptable salt thereof, in admixture with pharmaceutically acceptable auxiliaries.

* * * * *